US010422806B1

(12) United States Patent
Patel et al.

(10) Patent No.: US 10,422,806 B1
(45) Date of Patent: Sep. 24, 2019

(54) METHODS FOR IMPROVING ASSAYS OF BIOLOGICAL SAMPLES

(71) Applicant: Theranos, Inc., Palo Alto, CA (US)

(72) Inventors: Paul Patel, Palo Alto, CA (US); Ian Gibbons; Elizabeth A. Holmes, Palo Alto, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 14/341,422

(22) Filed: Jul. 25, 2014

Related U.S. Application Data

(60) Provisional application No. 61/858,589, filed on Jul. 25, 2013, provisional application No. 61/903,346, filed on Nov. 12, 2013.

(51) Int. Cl.
*G01N 33/82* (2006.01)
*G01N 33/569* (2006.01)

(52) U.S. Cl.
CPC ....... *G01N 33/82* (2013.01); *G01N 33/56972* (2013.01)

(58) Field of Classification Search
None
See application file for complete search history.

(56) References Cited

U.S. PATENT DOCUMENTS

| | | | |
|---|---|---|---|
| 4,269,604 A | 5/1981 | Snowden | |
| 4,991,433 A | 2/1991 | Warnaka et al. | |
| 5,326,445 A | 7/1994 | Lauer et al. | |
| 5,551,241 A | 9/1996 | Boeckel et al. | |
| 5,578,269 A | 11/1996 | Yaremko et al. | |
| 5,578,270 A | 11/1996 | Reichler et al. | |
| 5,602,647 A | 2/1997 | Xu et al. | |
| 5,772,962 A | 6/1998 | Uchida et al. | |
| 5,779,981 A | 7/1998 | Danssaert et al. | |
| 5,807,523 A | 9/1998 | Walls et al. | |
| 5,844,686 A | 12/1998 | Treptow et al. | |
| 5,896,297 A | 4/1999 | Valerino | |
| 5,906,795 A | 5/1999 | Nakashima et al. | |
| 5,993,417 A | 11/1999 | Yerfino et al. | |
| 6,013,528 A | 1/2000 | Jacobs et al. | |
| 6,030,582 A | 2/2000 | Levy | |
| 6,060,022 A | 5/2000 | Pang et al. | |
| 6,091,490 A | 7/2000 | Stellman et al. | |
| 6,114,122 A | 9/2000 | Besemer et al. | |
| 6,121,054 A | 9/2000 | Lebl | |
| 6,136,201 A | 10/2000 | Shah et al. | |
| 6,143,252 A | 11/2000 | Haxo, Jr. et al. | |
| 6,191,852 B1 | 2/2001 | Paffhausen et al. | |
| 6,197,572 B1 | 3/2001 | Schneebeli | |
| 6,235,534 B1 | 5/2001 | Brookes et al. | |
| 6,290,907 B1 | 9/2001 | Takahashi et al. | |
| 6,309,828 B1 | 10/2001 | Schleifer et al. | |
| 6,341,490 B1 | 1/2002 | Jones | |
| 6,348,176 B1 | 2/2002 | Hammer et al. | |
| 6,361,486 B1 | 3/2002 | Gordon | |
| 6,372,185 B1 | 4/2002 | Shumate et al. | |
| 6,379,929 B1 | 4/2002 | Burns et al. | |
| 6,468,474 B2 | 10/2002 | Bachand et al. | |
| 6,509,193 B1 | 1/2003 | Tajima | |
| 6,565,813 B1 | 5/2003 | Garyantes | |
| 6,583,879 B1 | 6/2003 | Berg et al. | |
| 6,589,789 B1 | 7/2003 | Hubert et al. | |
| 6,652,809 B1 | 11/2003 | Comley et al. | |
| 6,689,615 B1 | 2/2004 | Murto et al. | |
| 6,752,965 B2 | 6/2004 | Levy | |
| 6,825,921 B1 | 11/2004 | Modlin et al. | |
| 6,858,185 B1 | 2/2005 | Kopf-Sill et al. | |
| 6,859,830 B1 | 2/2005 | Ronneburg et al. | |
| 7,192,786 B1 | 3/2007 | Lövgren et al. | |
| 7,754,433 B2 * | 7/2010 | Babcook et al. | ............. 435/7.1 |
| 8,158,430 B1 | 4/2012 | Roy et al. | |
| 2001/0019845 A1 | 9/2001 | Bienert et al. | |
| 2002/0010145 A1 | 1/2002 | Willson et al. | |
| 2002/0059030 A1 | 5/2002 | Otworth et al. | |
| 2002/0065457 A1 | 5/2002 | Kuth | |
| 2002/0074882 A1 | 6/2002 | Werfel et al. | |

(Continued)

FOREIGN PATENT DOCUMENTS

IN WO 2009130709 * 10/2009

OTHER PUBLICATIONS

Altekar et al. (JALA Feb. 2006, p. 33-41).*
Biomek FX catalogue (2009).*
Mire-Sluis et al. (J. Immunological Methods 2004, vol. 289, p. 1-16).*
Feng et al. J. Immunoassay Immunochemistry 2009 vol. 30, p. 457-466.*
Cox et al. Assay Guidance Manuel 2012, total 39 pages.*
Dong et al. J. Sci. Food Agricuture 2010 vol. 90, p. 1106-1112.*

*Primary Examiner* — Changwa J Cheu

(57) ABSTRACT

Methods for improving assays of biological samples are provided, including assays of small volume biological samples, such as blood samples obtained from a fingerstick. The methods include steps of selecting a baseline assay; providing a first revised assay by altering an aspect, a reagent, or a step of the baseline assay; comparing the results of the baseline assay and first revised assay; and identifying the first revised assay as an improved assay if the results of the first revised assay are similar to, are substantially the same as, or are better than, the results of the baseline assay. The methods may be iterated. Alterations include reducing sample volume; setting temperature; reducing step number and duration; altering reagent composition and number; and altering detection. Improved assays may reduce the duration, cost, or complexity of the assay, may improve assay sensitivity, accuracy, or reliability, and may provide synergistic improvements.

9 Claims, 13 Drawing Sheets

(56) References Cited

U.S. PATENT DOCUMENTS

| | | |
|---|---|---|
| 2002/0085952 A1 | 7/2002 | Ellingboe et al. |
| 2002/0108857 A1 | 8/2002 | Paschetto et al. |
| 2002/0120187 A1 | 8/2002 | Eiffert et al. |
| 2002/0141904 A1 | 10/2002 | Rosen et al. |
| 2002/0149772 A1 | 10/2002 | Halg |
| 2002/0155599 A1 | 10/2002 | Vellinger et al. |
| 2002/0155616 A1 | 10/2002 | Hiramatsu et al. |
| 2002/0160353 A1 | 10/2002 | Sundaram et al. |
| 2002/0161606 A1 | 10/2002 | Bennett et al. |
| 2002/0164770 A1 | 11/2002 | Hoffmann |
| 2003/0012699 A1 | 1/2003 | Moore et al. |
| 2003/0064525 A1 | 4/2003 | Liess |
| 2003/0100822 A1 | 5/2003 | Lew et al. |
| 2003/0127609 A1 | 7/2003 | El-Hage et al. |
| 2003/0138140 A1 | 7/2003 | Marcelpoil et al. |
| 2003/0143580 A1 | 7/2003 | Straus |
| 2004/0020310 A1 | 2/2004 | Escal |
| 2004/0022677 A1 | 2/2004 | Wohlstadter et al. |
| 2004/0029266 A1 | 2/2004 | Barbera-Guillem |
| 2004/0055361 A1 | 3/2004 | Schneider et al. |
| 2004/0087426 A1 | 5/2004 | Lattanzi |
| 2004/0115720 A1 | 6/2004 | McWilliams et al. |
| 2004/0134750 A1 | 7/2004 | Luoma |
| 2004/0161368 A1 | 8/2004 | Holtlund et al. |
| 2004/0166027 A1 | 8/2004 | Wilmer et al. |
| 2004/0174821 A1 | 9/2004 | Eggeling et al. |
| 2004/0241043 A1 | 12/2004 | Sattler |
| 2004/0241048 A1 | 12/2004 | Shin et al. |
| 2005/0074873 A1 | 4/2005 | Shanler et al. |
| 2005/0100937 A1 | 5/2005 | Holmes |
| 2005/0106713 A1 | 5/2005 | Phan et al. |
| 2005/0125258 A1 | 6/2005 | Yellin et al. |
| 2005/0147559 A1 | 7/2005 | Von Alten |
| 2005/0152900 A1 | 7/2005 | Najib et al. |
| 2005/0159982 A1 | 7/2005 | Showalter et al. |
| 2005/0164204 A1 | 7/2005 | Reed |
| 2005/0176940 A1 | 8/2005 | King |
| 2005/0180885 A1 | 8/2005 | Tateishi et al. |
| 2005/0180892 A1 | 8/2005 | Davies et al. |
| 2005/0220668 A1 | 10/2005 | Coville |
| 2005/0225751 A1 | 10/2005 | Sandell et al. |
| 2005/0227370 A1 | 10/2005 | Ramel et al. |
| 2005/0231723 A1 | 10/2005 | Blasenheim et al. |
| 2005/0236317 A1 | 10/2005 | DeSilets et al. |
| 2006/0013733 A1 | 1/2006 | Meeks et al. |
| 2006/0019274 A1 | 1/2006 | Goel |
| 2006/0024841 A1 | 2/2006 | Yao et al. |
| 2006/0026040 A1 | 2/2006 | Reeves et al. |
| 2006/0034732 A1 | 2/2006 | Bargh et al. |
| 2006/0045806 A1 | 3/2006 | Winther et al. |
| 2006/0051243 A1 | 3/2006 | Chow et al. |
| 2006/0057559 A1 | 3/2006 | Xu et al. |
| 2006/0057599 A1 | 3/2006 | Dzenitis et al. |
| 2006/0062697 A1 | 3/2006 | Eberle |
| 2006/0062852 A1 | 3/2006 | Holmes |
| 2006/0073538 A1 | 4/2006 | Konrad |
| 2006/0074063 A1 | 4/2006 | Fernandez-Pol |
| 2006/0083660 A1 | 4/2006 | Schorno et al. |
| 2006/0095429 A1 | 5/2006 | Abhyankar et al. |
| 2006/0110725 A1 | 5/2006 | Lee et al. |
| 2006/0115384 A1 | 6/2006 | Wohleb |
| 2006/0121491 A1 | 6/2006 | Wolber et al. |
| 2006/0121502 A1 | 6/2006 | Cain et al. |
| 2006/0153736 A1 | 7/2006 | Kalra et al. |
| 2006/0154327 A1 | 7/2006 | Bachur et al. |
| 2006/0160170 A1 | 7/2006 | Giordano |
| 2006/0182738 A1 | 8/2006 | Holmes |
| 2006/0183217 A1 | 8/2006 | Yanagida et al. |
| 2006/0210435 A1 | 9/2006 | Alavie et al. |
| 2006/0223178 A1 | 10/2006 | Barber et al. |
| 2006/0245978 A1 | 11/2006 | Prins |
| 2006/0263263 A1 | 11/2006 | Shimizu |
| 2006/0263871 A1 | 11/2006 | Kluttz et al. |
| 2006/0264780 A1 | 11/2006 | Holmes et al. |
| 2006/0264783 A1 | 11/2006 | Holmes et al. |
| 2006/0275861 A1 | 12/2006 | Angros et al. |
| 2006/0281187 A1 | 12/2006 | Emery et al. |
| 2006/0286619 A1 | 12/2006 | Ricci et al. |
| 2006/0292039 A1 | 12/2006 | Iida |
| 2007/0004577 A1 | 1/2007 | Lederer |
| 2007/0035819 A1 | 2/2007 | Bahatt et al. |
| 2007/0048188 A1 | 3/2007 | Bigus |
| 2007/0055538 A1 | 3/2007 | Burton |
| 2007/0059196 A1 | 3/2007 | Brister et al. |
| 2007/0073113 A1 | 3/2007 | Squilla et al. |
| 2007/0077173 A1 | 4/2007 | Melet |
| 2007/0109294 A1 | 5/2007 | Gotman et al. |
| 2007/0118399 A1 | 5/2007 | Avinash et al. |
| 2007/0125677 A1 | 6/2007 | Oronsky et al. |
| 2007/0131870 A1 | 6/2007 | Pang et al. |
| 2007/0134128 A1 | 6/2007 | Korlach |
| 2007/0146873 A1 | 6/2007 | Ortyn et al. |
| 2007/0148759 A1 | 6/2007 | Amano et al. |
| 2007/0149874 A1 | 6/2007 | Say et al. |
| 2007/0154922 A1 | 7/2007 | Collier et al. |
| 2007/0177778 A1 | 8/2007 | Massaro |
| 2007/0192138 A1 | 8/2007 | Saito et al. |
| 2007/0202538 A1 | 8/2007 | Glezer et al. |
| 2007/0207161 A1 | 9/2007 | Ralph |
| 2007/0207450 A1 | 9/2007 | Rodgers et al. |
| 2007/0224084 A1 | 9/2007 | Holmes et al. |
| 2007/0264629 A1 | 11/2007 | Holmes et al. |
| 2007/0269345 A1 | 11/2007 | Schilffarth et al. |
| 2007/0292941 A1 | 12/2007 | Handique et al. |
| 2007/0295113 A1 | 12/2007 | Londo et al. |
| 2008/0001735 A1 | 1/2008 | Tran |
| 2008/0003649 A1 | 1/2008 | Maltezos et al. |
| 2008/0003668 A1 | 1/2008 | Uchiyama et al. |
| 2008/0019878 A1 | 1/2008 | Trump |
| 2008/0026483 A1 | 1/2008 | Oldenburg |
| 2008/0032416 A1 | 2/2008 | Park et al. |
| 2008/0038771 A1 | 2/2008 | Taylor et al. |
| 2008/0065420 A1 | 3/2008 | Tirinato et al. |
| 2008/0110753 A1 | 5/2008 | Fourrier et al. |
| 2008/0118988 A1 | 5/2008 | Johnson et al. |
| 2008/0144005 A1 | 6/2008 | Guiney et al. |
| 2008/0153096 A1 | 6/2008 | Witty et al. |
| 2008/0166753 A1 | 7/2008 | Storey et al. |
| 2008/0179301 A1 | 7/2008 | Garty et al. |
| 2008/0198379 A1 | 8/2008 | Coker et al. |
| 2008/0206751 A1 | 8/2008 | Squirrell et al. |
| 2008/0223841 A1 | 9/2008 | Lofy |
| 2008/0228107 A1 | 9/2008 | Reddy |
| 2008/0253927 A1 | 10/2008 | Burow et al. |
| 2008/0253933 A1 | 10/2008 | Redfern |
| 2008/0261210 A1 | 10/2008 | Frantzen et al. |
| 2008/0299652 A1 | 12/2008 | Owen et al. |
| 2008/0308404 A1 | 12/2008 | Luotola et al. |
| 2009/0004754 A1 | 1/2009 | Oldenburg |
| 2009/0021728 A1 | 1/2009 | Heinz et al. |
| 2009/0043607 A1 | 2/2009 | Nemoto et al. |
| 2009/0057259 A1 | 3/2009 | Johnson et al. |
| 2011/0093249 A1 | 4/2011 | Holmes et al. |
| 2012/0149035 A1 | 6/2012 | Burd et al. |
| 2012/0178091 A1 | 7/2012 | Glezer et al. |
| 2013/0115685 A1 | 5/2013 | Holmes et al. |
| 2015/0185234 A1 | 7/2015 | Gibbons et al. |
| 2016/0025760 A1 | 1/2016 | Holmes |

\* cited by examiner

METHODS FOR IMPROVING ASSAYS OF BIOLOGICAL SAMPLES

CROSS-REFERENCE TO RELATED APPLICATIONS

This application claims priority to, and the benefit under 35 U.S.C. § 119(e) of, U.S. Patent Application Ser. No. 61/858,589, filed Jul. 25, 2013, and U.S. Patent Application Ser. No. 61/903,346, filed Nov. 12, 2013, the entire contents of which applications are hereby incorporated by reference in their entireties.

BACKGROUND

This application is directed to methods for detecting the presence of, absence of, or amount of, a target analyte (e.g., a material of interest) in a biological sample.

Methods for detecting analytes in a sample and for determining the chemical composition of a sample are useful in many clinical and scientific applications. A method for identifying, or for quantifying the amount of, a substance or substances in a sample may be termed an "assay." Assays typically include a step, or series of steps, applied to a sample in order to identify or quantify a sample, or a substance or substances in a sample. Assays typically include steps of contacting a sample with a reagent, and of detecting a signal indicative of the presence or absence, or of the quantity of, an analyte. Some assays are performed by devices or systems designed to perform the assays with little or no human intervention; such assays may be termed automated assays, and are performed by automatic devices or automatic systems.

Clinical assays are often developed to identify target materials in samples taken from patients. For example, targets may include proteins, nucleic acids, lipids, organic molecules, inorganic molecules and ions. Such target materials may include drugs, drug metabolites, vitamins, hormones, growth factors, carrier proteins, cells, infectious agents, and other target materials that may be indicative of medical conditions or disorders.

Many different assays with different advantages (and disadvantages) may be developed that are directed to the same analytes. In addition, the properties and identifying characteristics of samples and of analytes may vary widely; for this reason, assays of various kinds and of differing complexities may be required in order to identify and quantify different targets. Some assays may be better suited for use in identifying protein targets than in identifying nucleic acid targets, for example. Some assays may be better suited for use on automated devices or systems than for performance by hand. Accordingly, some assays may be better suited to different targets, or to different applications, or different methods of performance, than other assays.

Assays for clinically relevant targets take many forms, partly for historical reasons and partly due to the many different chemical and biochemical approaches available to detect and measure the same or similar targets. Different techniques may be used to bind to or otherwise interact with a target, and different techniques may be used to signal such binding or other interactions. For example, binding interactions typically include specific and non-specific binding, which must be distinguished in an assay; in addition, different samples, and different targets, have different amounts and kinds of interfering non-specific binding interactions. Since binding to a target may be by competitive, non-competitive, or uncompetitive mechanisms, different assay strategies and conditions must be determined and used for the different kinds of interactions, or strategies and conditions must be found that are useful for multiple kinds of binding interactions. In addition, the results of any such binding interactions must be detected in order for an assay to be of any use; multiple strategies and techniques are available and may be used for detecting and quantifying binding interactions with target materials in a sample.

Thus, there may be multiple ways to perform an assay; each way may have different advantages and disadvantages. An assay method may have advantages when compared to other assay methods: for example an assay method may be faster, or may be simpler, or may be more readily quantified, than other methods. However, an assay method may have disadvantages when compared to other assay methods; for example an assay method may be more expensive, or slower, or may only provide a signal that is harder to detect or to quantify, than other methods. Typically, an assay method will have some advantages and also have some disadvantages, when compared to other assay methods, and the advantages and disadvantages of an assay may differ when it is performed by automated device or system as compared to the performance of the assay by hand.

In some instances, a sample may include multiple analytes, and multiple assays may be required to detect or quantify all of the analytes of interest in a sample. However, choosing an assay for an analyte from among the many possible alternative assays, and in particular choosing an assay for detecting or quantifying the analyte that is also suitable for use with other assays for other analytes, presents complicated choices.

Each of the different conditions and strategies which may possibly be used in an assay will have different costs, different levels of complexity and difficulty, and different levels of reliability and consistency than other conditions and strategies. For example, some strategies and some assay conditions may be less expensive than others, or may provide quicker results than others; cheaper assays and quicker results may, or may not, be of equal accuracy or reliability as results from other assays that take longer or are more expensive. In general, assays may be improved, e.g., may be altered to provide more accurate, or more reliable, or more rapid, results, or may be altered in order to reduce the costs associated with performing the assay. In general, there are a multitude of possible approaches, ways, and means for improving assays. However, it is often not clear what approach to take, or what ways or means to use, in order to improve an assay.

Accordingly, guidelines and methods for altering assays in order to provide improved assays are needed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Assays provide means to determine whether or not a chemical element or compound of interest (an analyte) is absent or present in a sample, and may provide means to quantify the amount of an analyte in a sample. There are typically many possible assay approaches, using many different steps, reagents, and detectors that may be used in assaying for any particular analyte in a sample. Automatic assay devices and systems provide useful means of analyzing samples, and of performing multiple analyses on a single sample. Where a sample may include multiple analytes of interest, multiple assays may be required that are suitable for use in analyzing the same sample, or in analyzing different aliquots taken from a single sample.

In order to improve an existing assay, changes must be made to one or more of the assay conditions, procedures, reagents, or other aspects of the assay. Adapting an existing assay for use on an automated assay device or system may require that changes be made in the sample acquisition, sample preparation, sample treatment, analyte detection, or other aspects of the assay. The number of possible changes that may be made to an existing assay is enormous, making it impractical to enumerate, and practically impossible to test, each possible change and each possible combination of changes.

Applicants disclose herein, out of all the myriad possible changes and combinations of possible changes, particular methods for improving assays which select and identify specific changes to be made in improving assays for use in an automatic device or system. In particular, Applicants disclose herein methods for improving assays for detecting the presence of, absence of, or quantifying the amount of, an analyte in a biological sample; these methods are directed to improving assays for use in an automatic device or automatic system. These methods include methods for improving assays for concurrent use with other assays in an automatic device or automatic system, where all assays use aliquots taken from the same biological sample. Improved assays disclosed herein use aliquots of diluted sample, providing the advantage that only small volumes of biological sample need be obtained from a subject for the assay, or assays, to be performed.

Accordingly, Applicants disclose herein methods for modifying assays from their initial form (termed "baseline assays"), by providing one or more revised assays that differ from the corresponding baseline assays in one or more ways, and comparing the results of revised assays with results of baseline assays, in order to provide and identify improved assays that provide advantages as compared with the baseline assays. An improved assay may provide, for example, one or more of: more rapid results as compared with a corresponding baseline assay; more reliable results as compared with a corresponding baseline assay; more precise results as compared with a corresponding baseline assay; more accurate results as compared with a corresponding baseline assay; more inexpensive results as compared with a corresponding baseline assay; further information regarding the target as compared with a corresponding baseline assay; and other advantages as compared with a corresponding baseline assay.

A baseline assay may require a baseline sample volume, and may include a baseline mixing step (using baseline reagents), or a plurality of baseline mixing steps, and a baseline detection step or steps. A revised assay is provided by altering: a step; a condition; a reagent; a plurality of steps, reagents, or conditions; a sequence of steps; or other aspect of a baseline assay. Comparison of the results of a revised assay, or of a plurality of revised assays, with the results of a baseline assay is useful in identifying an improved assay, wherein an improved assay is an assay that differs from the baseline assay in one or more ways, and which provides results having one or more advantages as compared to the baseline assay. It will be understood that not all reagents, conditions, or steps, need be altered in order to improve an assay. Advantages offered by improved assays, as compared with a baseline assay, include, for example, more rapid assays; more accurate assays; more reliable and repeatable assays; simpler assays; less expensive assays; combined assays (e.g., assays which may detect or quantify two or more analytes); assays which use a preferred detection method; and other advantages.

In embodiments, a baseline assay may be improved by altering the baseline assay, for example, by decreasing the sample volume required; by reducing the complexity of, or by eliminating, sample pretreatment steps; by reducing the number of reagents required; by reducing the number, duration, or complexity of steps; by altering the assay temperature (e.g., by setting the assay temperature to between about 30° C. and about 40° C., or between 32° C. and about 38° C., or to between 32° C. and about 37° C., or between 34° C. and about 37° C.); by simplifying the assay conditions; by shortening the time period between initiation of the assay and the analyte detection step; by reducing the cost of reagents; and combinations thereof.

In embodiments, reducing the number, duration, or complexity of assay steps may be achieved by reducing the number of mixing steps, e.g., by combining reagents used in separate mixing steps to provide a single mixing step or fewer mixing steps; by increasing reactant concentration or reaction temperature in order to reduce reaction time; by using alternative chemistry (e.g., providing a unary reaction (single reactant) or a binary reaction (two reactants) to produce a detectable signal as compared to a multi-step reaction (e.g., involving multiple reagents and reactants); and by other means.

The practice of the methods disclosed herein may provide unexpected benefits, including synergistic improvements provided by the assay alterations, in addition to the direct benefits provide by individual assay alterations. Such synergistic effects may include synergistic effects on the assay which has been altered (e.g., increased or improved assay signals, improved reliability, reduced assay time, reduced assay cost, and other advantages). For example, reducing the number of reagents required for an assay may reduce the number of steps, or the duration of steps, required to perform the assay, reducing the time between assay initiation and obtaining results, and so improve the reliability of the results where an analyte may degrade over time. Improved assays may allow a reduction in the total sample volume required to be obtained from a subject, making the assay more comfortable for a subject, or allowing assays to be performed on a wider range of patients by including infants or others for whom larger volume samples may be difficult to obtain.

Synergy may be found when an assay is improved, where the improved assay is one of a group of assays performed on a single device or system that is used to perform multiple assays on a single sample, or on aliquots of a single sample. Improvements in one assay may allow or improve the ability of a device or system to perform multiple assays on a single biological sample, or to perform multiple assays in less time or with fewer reagents or system resources. For example, reducing the sample volume required for an assay leaves more sample available for use by other assays; reducing the time required for an assay provides more time, and more sequencing or multiplexing options, for other assays performed on the same device or system; reducing the number of steps required for an assay reduces system resources required to be allocated to that assay, freeing them up for use by other assays; increasing signal intensity may reduce the time required for a detection step, thereby providing greater access to that particular—critical—shared resource (a detector) for use by other assays. For example, the direct change of increasing a reagent concentration may lead to an increase in a rate of a reaction that allows the shortening of a reaction step, and, e.g., if the altered reaction provides a signal, the direct change may further lead to the synergistic improvement of an increase in signal intensity in addition to the shortening of reaction time. For example, the direct change of combining reagents to provide a single reagent may allow combination of reaction steps, leading to the further advantages of shortening the total assay time and reducing the cost of the assay (e.g., if the single combined reagent requires less buffer and other constituents than were required for the prior two separate reagents); in addition, such a direct change and corresponding additional improvements may provide a further synergistic advantage of allowing better coordination of the assay with other assays to be performed on the same sample, in a single device or system by shortening the time required, and lessening the system resources required for that assay (e.g., since the assay has fewer reagents and fewer steps). Thus, assay alterations as disclosed herein may provide improvements beyond the direct changes made to assays. These improvements and accompanying synergistic advantages may be exploited in the individual (improved) assay and also, e.g., in devices and systems for analyzing samples which perform multiple assays in a single device or system.

In embodiments, the practice of the methods disclosed herein has provided unexpected benefits, including synergistic improvements provided by the assay alterations. For example, as disclosed herein, combination of assay steps in a cytometric assay not only provided the benefit of reduced total assay time, but also provided unexpected benefits by reducing the amount of dye required, and improving the reliability of the assay.

Accordingly, Applicants disclose novel methods for improving assays. For example, Applicants disclose a method for improving an assay for use in an automatic assay device, said assay comprising detecting the presence of, detecting the absence of, or quantifying the amount of, an analyte in a biological sample, said method comprising: Selecting a baseline assay performed at a baseline assay temperature on a baseline volume of biological sample, and comprising one or more steps selected from pre-treating, diluting, aliquotting, separating, transporting, mixing, incubating, reacting, labeling, and detecting, the duration of said steps comprising baseline step durations, the time period required to perform said baseline assay in its entirety comprising a total baseline assay duration, and the performance of said baseline assay providing baseline results; Providing a first revised assay based on said baseline assay by: Providing a first reduced volume of said biological sample, or a portion thereof, for use in the performance of said first revised assay, said first reduced volume comprising a smaller volume than said baseline volume; then Reducing the duration of, or eliminating, a pretreatment step applied to said biological sample or portion thereof, if any; then Diluting said first reduced volume of biological sample by at least 10-fold to provide diluted biological sample; then Altering the steps of said baseline assay by one or more of: i) Altering a reagent composition or reducing the number of reagents used in the performance of the assay; ii) Providing an altered assay temperature different than said baseline assay temperature; and iii) Shortening the duration of a step, eliminating a step, combining two or more steps, altering the sequence of performance of steps, or combinations thereof; then Performing said first revised assay at said altered assay temperature on an aliquot of said diluted biological sample or aliquot thereof to provide first revised results; then Determining a difference, or lack thereof, between said baseline results and said first revised results; and Identifying the first revised assay as an improved assay if the first revised results are as food as, or better than, the baseline results, Whereby the baseline assay is improved if the first revised assay is identified as an improved assay.

Applicants further disclose methods comprising the methods disclosed above, and further comprising the following steps: Providing a second revised assay based on said first revised assay by: Providing a second reduced volume of said biological sample, or a portion thereof, for use in the performance of said second revised assay, said second reduced volume comprising a smaller volume than said first reduced volume if said first reduced volume comprises a volume of more than about 250 µL, and wherein said second reduced volume comprises said first reduced volume if said first reduced volume comprises a volume of no more than about 250 µL; then Diluting said second reduced volume of biological sample, or portion thereof, by at least 10-fold to provide diluted biological sample; then Altering the steps of said first revised assay by one or more of: i) Altering a reagent composition or reducing the number of reagents used in the performance of the assay; ii) Altering the assay temperature; and iii) Shortening the duration of a step, eliminating a step, combining two or more steps, altering the sequence of performance of steps, or combinations thereof; then Performing said second revised assay on an aliquot of diluted biological sample to provide second revised results; then Determining a difference, or lack thereof, between said baseline results and said second revised results; and Identifying the second revised assay as an improved assay if the second revised results are as good as, or better than, the baseline results, Whereby the baseline assay is improved if the second revised assay is identified as an improved assay.

In embodiments, the altering performed in the practice of these methods may comprise setting assay temperature to between about 30° C. and about 40° C., or between about 32° C. and about 38° C., or to between 32° C. and about 37° C., or between about 34° C. and about 37° C.; altering the duration of a step; altering at least one step selected from the steps of treating, mixing, and incubating; altering a reagent used in a step; eliminating a reagent; combining two or more reagents to provide a single combined reagent; eliminating an ingredient from a reagent; replacing an ingredient in a reagent; adding an ingredient to a reagent; increasing the amount of an ingredient in a reagent; decreasing the amount of an ingredient in a reagent; altering the pH or osmolarity of a reagent; and combinations thereof.

In embodiments, the aliquot comprises a volume of about 10 µL or less. In embodiments, the revised assay further comprises transporting said biological sample, a reagent, or both within a housing comprising a detector.

In further embodiments, Applicants disclose methods for improving a baseline assay to provide an improved assay for use in an automatic assay device, said baseline assay comprising detecting the presence of, detecting the absence of, or quantifying the amount of, an analyte in a biological sample having a sample volume, said method comprising: Providing a revised assay by altering said baseline assay by: Reducing said sample volume to about 250 µL or less; Diluting said volume of biological sample by at least 10-fold to provide diluted biological sample; Setting the assay temperature of the revised assay to between about 30° C. and about 40° C., or between about 32° C. and about 38° C., or to between 32° C. and about 37° C., or between about 34°

C. and about 37° C.; Altering a step, altering the sequence of performance of steps, or both; Eliminating a reagent or combining two or more of said reagents to provide no more than two reagents for use in said revised assay; Reducing the duration of a step, eliminating a step, or combining two or more steps, effective that the time required to perform the revised assay is reduced as compared to the time required to perform the baseline assay; Requiring that said detection step comprises an optical detection step; Performing said revised assay on an aliquot of diluted biological sample to provide results of said revised assay; and Comparing the results of said revised assay with the results of said baseline assay, Wherein the baseline assay is improved if the results of the first revised assay are as good as, or better than, the baseline results. In embodiments, a second iteration of these steps may be performed, wherein the improved assay obtained by the performance of the first iteration of the method is used as the baseline assay for the performance of the second iteration of the method.

In embodiments, the optical detection step comprises optical detection using a photomultiplier tube (PMT), a photodiode, a photon counting device, a charge-coupled device (CCD), a camera, a microscope, and arrays and combinations thereof. Optical detection may include colorimetric detection, fluorimetric detection, luminometric detection, turbidometric detection, absorbance detection, light scattering detection, or combinations thereof.

In embodiments, the time required to perform an improved assay may be less than about one hour, or less than about 50 minutes, or less than about 40 minutes, or less than about 30 minutes, or less than about 20 minutes, or less than about 10 minutes, or less than about 5 minutes. In embodiments, the volume of an aliquot of diluted biological sample may be about 10 μL or less, may be about 5 μL or less. In embodiments, performing the improved assay comprises three or fewer assay steps. In embodiments, the cost of the reagents required for performing the improved assay is less than the cost of reagents required for performing the baseline assay; for example, the cost of the reagents required for performing the improved assay may be about 10 or less per assay.

In embodiments, Applicants disclose methods for improving a baseline assay for a first analyte, said baseline assay being for concurrent use with other assays for other analytes in an automatic assay device, said assays comprising detecting the presence of, detecting the absence of, or quantifying the amount of, analytes in the same biological sample having a sample volume, said method comprising the steps of: Selecting a first baseline assay; Setting sample volume to about 250 μL or less; Diluting the sample by at least 10-fold to provide a diluted sample; and In a first iteration, Providing a revised assay based on said first baseline assay by altering a step, or sequence of steps of said first baseline assay; Performing said revised assay on an aliquot of said diluted sample; Comparing the results of performance of the first baseline assay to the results of the performance of the revised assay, wherein, In a second iteration: a) if the results of the revised assay are not as good as the results of the first baseline assay, then: Providing a further revised assay based on said first baseline assay by altering a step, or sequence of steps of said first baseline assay, wherein said altering differs from the previously performed alteration; Performing said further revised assay on an aliquot of diluted sample; and Comparing the results of performance of the further revised assay to those of the first baseline assay, wherein if the results of the further revised assay are not as good as the results of the first baseline assay, then the further revised assay is not an improved assay, and the second iteration may be repeated by further altering a step, or sequence of steps of said first baseline assay, wherein said altering differs from the previously performed alteration; or b) if the results of the revised assay are as good as, or better than, the results of the first baseline assay, then: Selecting said revised assay as a second baseline assay; and, in a second iteration, Providing a further revised assay based on said second baseline assay by altering a step, or sequence of steps of said second baseline assay; Performing said further revised assay on an aliquot of diluted sample; and Comparing the results of performance of the baseline assay to the results of the performance of the further revised assay, wherein, the further revised assay is not an improved assay if the results of the further revised assay are not as good as the results of the baseline assay; Wherein, the further revised assay of step a) or b) is an improved assay if i) the results of the further revised assay are as good as, or better than, the results of the baseline assay, and ii) the further revised assay is more readily performed concurrently with other assays using portions of the same sample in an automatic assay device than is the baseline assay.

In embodiments, Applicants disclose methods for improving a baseline assay for a first analyte for concurrent use with other assays for other analytes in an automatic assay device, said assays comprising detecting the presence of, detecting the absence of, or quantifying the amount of, other analytes in the same biological sample, said method comprising the steps of: Selecting a baseline assay; and Providing an improved assay based on said baseline assay, wherein said providing said improved assay comprises: Reducing the volume of the biological sample if the baseline assay sample volume is greater than about 250 μL; Simplifying or eliminating pretreatment of said sample if the baseline assay includes a sample pretreatment step; Diluting the biological sample by at least 10-fold to provide a diluted sample for providing an aliquot of diluted sample for use in the performance of the improved assay; Altering the assay temperature to be greater than or equal to about 30° C. if the baseline assay temperature is less than 30° C., or to be greater than about 32° C. if the baseline assay temperature is less than 32° C., or to be greater than about 34° C. if the baseline assay temperature is less than 34° C.; Altering the composition of a reagent, eliminating a reagent or combining two reagents, or a combination thereof, to provide no more than two reagents for the improved assay; Eliminating an assay step or combining two assay steps if the baseline assay includes more than three steps; and Reducing the time required to perform the assay to 30 minutes or less by reducing the duration of a step, reducing the number of steps, combining steps, or a combination thereof if the time required to perform the baseline assay time is greater than 30 minutes; Thereby providing an improved assay for said first analyte, said improved assay being for concurrent use in an automatic assay device with other assays for other analytes in the same biological sample. In embodiments, the time to perform the assay may be reduced to less than about 20 minutes, or less than about 10 minutes, or less than about 5 minutes. In embodiments, the time required to perform the baseline assay may be more than 30 minutes; e.g., may be one hour or more; in embodiments, the time required to perform the assay may be reduced to less than about one hour, or less than about 50 minutes, or less than about 40 minutes, or less than about 30 minutes.

Applicants further disclose herein methods for improving a baseline assay for a first analyte in a biological sample, effective to provide an improved assay for concurrent use in an automatic assay device with other assays for other analytes, said assays being for detecting the presence of, absence of, or for quantifying the amount of, analytes in the same biological sample having a sample volume, wherein said improved assay meets predetermined performance criteria, said method comprising: Selecting a baseline assay to be improved; Providing a first revised assay by altering said baseline assay by: Setting the first revised sample volume to be about 250 μL or less; Simplifying or eliminating sample pretreatment step or steps, if present in the baseline assay; Diluting said biological sample by at least 10-fold to provide a diluted sample; Setting the temperature of the revised assay to between about 30° C. and about 40° C., or to between about 32° C. and about 38° C., or to between 32° C. and about 37° C., or to between about 34° C. and about 37° C.; Estimating reagent concentration and volumes required for the revised assay in view of: the dilution, the adjusted temperature, and the ratio between the sample volume of the baseline assay and the first revised sample volume; Performing the revised assay on an aliquot of the diluted biological sample; and a) comparing the results of performance of the first revised assay with the results of performance of the baseline assay; Altering one or more of reagents, steps, and step sequences of the revised assay to provide a further revised assay, and comparing the results of said further revised assay to the results of the baseline assay if the results of the first revised assay were not as good as the results of the baseline assay; or b) comparing the results of said further revised assay to the results of the first revised assay if the results of the first revised assay were as good as, or better than, the results of the baseline assay; and comparing the results of performance of said further revised assay of a) or b) to said performance criteria, wherein said further revised assay is identified as an improved assay if the results of the performance of said further revised assay meet said performance criteria.

In embodiments, a baseline assay may be selected from an immunoassay, a nucleic acid assay, a cytometric assay, and a general chemistry assay.

In embodiments, a sample volume comprises about 125 μL; or about 100 μL; or about 75 μL; or about 50 μL; or about 25 μL; or about 15 μL; or about 10 μL; or about 5 μL; in further embodiments, a sample volume comprises the volume of a finger-stick.

In embodiments, an improved assay comprises an assay that works better in conjunction with other assays when said improved assay and said other assays are all performed concurrently using the same device or system to perform each of said assays using portions of the same biological sample.

In further embodiments, Applicants provide further improved assays for use in automatic assay devices or systems. In embodiments, the improved assays comprise improvements as compared to a baseline assay, where the baseline assay comprises detecting the presence of, detecting the absence of, or quantifying the amount of, an analyte in a biological sample. The biological sample has a baseline sample volume, the duration of baseline assay steps comprise baseline step durations, and the baseline assay is performed at a baseline assay temperature on a baseline volume of biological sample; the time period required to perform the baseline assay in its entirety comprises a total baseline assay duration.

In embodiments, an improved assay comprises detecting the presence of, detecting the absence of, or quantifying the amount of, an analyte in a biological sample, and comprising one or more steps selected from pre-treating, diluting, aliquotting, separating, transporting, mixing, incubating, reacting, labeling, and detecting; such an improved assay, as compared to the baseline assay, further comprises: a reduced biological sample volume comprising a smaller volume than said baseline volume; a reduced duration or eliminated pretreatment step applied to said biological sample; a diluted biological sample comprising an at least 10-fold dilution of said biological sample; and further comprises one or more of: i) an altered reagent composition; ii) a reduced number of reagents used in the performance of the assay; iii) an altered assay temperature; iv) a shortened step duration; v) an eliminated step; vi) a combination of two or more steps; and vii) an altered step sequence.

In embodiments, the reduced biological sample volume of such an improved assay comprises a volume of no more than about 250 μL. In embodiments, the improved assay comprises an altered step selected from the steps of treating, mixing, and incubating. In embodiments, an altered step comprises a shortened step duration. An altered step may comprise an altered reagent. Such an altered reagent may comprise a reagent altered by one or more of: eliminating a reagent; combining two or more reagents to provide a single combined reagent; eliminating an ingredient from a reagent; replacing an ingredient in a reagent; adding an ingredient to a reagent; increasing the amount of an ingredient in a reagent; decreasing the amount of an ingredient in a reagent; and altering the pH or osmolarity of a reagent. In embodiments, such an improved assay comprises an assay temperature of between about 32° C. and about 37° C.

In embodiments, such an improved assay comprises an aliquotting step, wherein the aliquot has a volume comprising about 10 μL or less.

In embodiments, such an improved assay comprises transporting said biological sample, a reagent, or both within a housing comprising a detector.

In embodiments, an improved assay as disclosed herein may comprise a biological sample volume of no more than about 250 μL; the use of no more than two reagents; a reduced assay duration as compared to the time required to perform the baseline assay; and a detection step comprising an optical detection step. In embodiments, an optical detection step may comprise optical detection selected from optical detection using a photomultiplier tube (PMT), a photodiode, a charge-coupled device (CCD), a photon counting detector, a camera, a microscope, and arrays and combinations thereof. In embodiments, optical detection comprises colorimetric detection, fluorimetric detection, luminometric detection, turbidometric detection, absorbance detection, light scattering detection, or combinations thereof.

In embodiments, the improved assay duration is less than about 30 minutes; in further embodiments, the improved assay duration is less than about 20 minutes; in further embodiments, the improved assay duration is less than about 10 minutes.

In embodiments, the improved assay comprises a step of aliquotting a diluted biological sample, wherein the volume of said aliquot of diluted biological sample comprises about 10 μL or less, or comprises about 5 μL or less.

In embodiments, the improved assay comprises three or fewer assay steps.

In embodiments, the cost of the reagents required for performing the improved assay is less than the cost of reagents required for performing the baseline assay. In embodiments, the cost of the reagents required for performing the improved assay comprises about 10 or less per assay.

Applicants further disclose an improved assay for a first analyte, wherein the improved assay comprises improvements as compared to a baseline assay for said first analyte, said baseline assay comprising detecting the presence of, detecting the absence of, or quantifying the amount of, the first analyte in a biological sample having a baseline sample volume, the duration of baseline assay steps comprising baseline step durations wherein said baseline assay is performed at a baseline assay temperature on a baseline volume of biological sample, and the time period required to perform said baseline assay in its entirety comprising a total baseline assay duration, the improved assay being suitable for concurrent use with one or more other assays for one or more other analytes in an automatic assay device, wherein each of said improved assays and assays for said other analytes comprises detecting the presence of, detecting the absence of, or quantifying the amount of, said first and said other analytes in the same biological sample, the biological sample having a sample volume, the improved assay comprising the steps of: setting the sample volume to about 250 µL or less; diluting the sample by at least 10-fold to provide a diluted sample; and altering a step, or a sequence of steps, of said baseline assay.

In embodiments, such an improved assay for a first analyte comprises: using a biological sample having a volume of about 250 µL or less; diluting the biological sample by at least 10-fold to provide a diluted sample; performing the assay at a temperature of greater than or equal to 32° C.; using no more than two reagents; performing no more than three sample treatment steps; and performing the assay in period of time of about 30 minutes or less.

In embodiments, such an improved assay for a first analyte comprises: using a biological sample having a sample volume of about 250 µL or less; simplifying or eliminating sample pretreatment step or steps, if present in the baseline assay; diluting said biological sample by at least 10-fold to provide a diluted sample; setting the temperature of the revised assay to between about 32° C. and about 37° C.; altering reagent concentration and volumes required for the improved assay as compared to the baseline assay in view of: the dilution, the adjusted temperature, and the ratio between the sample volume of the baseline assay and the sample volume of about 250 µL or less; and performing the improved assay on an aliquot of the diluted biological sample. In embodiments, the sample volume comprises about 125 µL or less.

In embodiments, such an improved assay is performed concurrently using the same device or system with another assay for a second analyte, each assay using a portion of the same biological sample. In embodiments, a baseline assay for the first analyte is selected from an immunoassay, a nucleic acid assay, a cytometric assay, and a general chemistry assay.

Applicants disclose methods for determining the concentration of vitamin B12 in a biological sample, the methods comprising steps performed at a temperature of at least about 32° C., said steps comprising: mixing said biological sample with a high pH buffer containing dithiothreitol, dicyanocobinamide, and potassium cyanide, wherein the volume ratio of sample to high pH buffer comprises about 2:3, to provide a first mixture; incubating said first mixture for about 10 minutes; reducing the pH of said first mixture by addition of a reagent including an acid to provide a reduced pH mixture; adding biotinylated intrinsic factor to said reduced pH mixture to provide a second mixture; adding vitamin B12-alkaline phosphatase conjugate to said second mixture to provide a third mixture, said third mixture comprising the reduced pH mixture containing biotinylated intrinsic factor and vitamin B12-alkaline phosphatase conjugate; contacting an avidin-coated surface with said third mixture; incubating said avidin-coated surface with said third mixture for about 10 minutes; removing the third mixture from the avidin-coated surface; contacting the avidin-coated surface with a solution containing dioxetane; incubating the avidin-coated surface with said solution containing dioxetane for about 10 minutes at a temperature; and detecting chemiluminescence, whereby the concentration of vitamin B12 in the biological sample is determined.

Applicants disclose methods of identifying cells in a sample of blood comprising steps performed at a temperature of at least about 32° C., the steps comprising: mixing said blood sample with a first reagent comprising a cell nucleus stain and a fluorescently labeled anti-CD14 antibody to provide a first mixture, wherein the ratio of the volume of sample to the volume of first reagent is about 10:1; incubating said first mixture for about 2 minutes; mixing the first mixture with a second reagent comprising paraformaldehyde to provide a second mixture, wherein the ratio of the volume of said first mixture to the volume of said second reagent is about 6:1; incubating said second mixture for about 3 minutes; centrifuging the second mixture at about 1200×g for about 1.5 minutes to provide a supernatant and a pellet; removing the supernatant following said centrifuging; mixing said pellet with a third reagent comprising fluorescently labeled anti-CD16 antibodies, fluorescently labeled anti-CD45 antibodies, and fluorescently labeled anti-CD123 antibodies to provide a third mixture; loading said third mixture on a cuvette; and imaging the sample, whereby cells are identified in a sample of blood.

In embodiments of the methods disclosed herein, a biological sample may comprise a sample of blood, serum, plasma, a nasal swab, a nasopharyngeal wash, saliva, urine, gastric fluid, cerebrospinal fluid, fluid obtained from a spinal tap, tears, stool, mucus, sweat, earwax, oil, a glandular secretion, semen, vaginal fluid, interstitial fluid, ocular fluids, a throat swab, tissue, breath, hair, finger nails, skin, biopsy samples, placental fluid, amniotic fluid, cord blood, lymphatic fluid, fluid from a body cavity, sputum, pus, microbiota, meconium, breast milk and other secretions and excretions.

Accordingly, in embodiments of methods for improving assays, an improved assay may require a smaller sample volume as compared with the baseline assay. In an embodiment of a method for improving an assay, a sample, or aliquot thereof, may be diluted, or a dilution step of the baseline assay may be altered to provide a greater amount of sample dilution in the improved assay, as compared with the baseline assay. In an embodiment of a method for improving an assay, an improved assay may comprise a shorter duration mixing step as compared with the baseline assay, or fewer mixing steps as compared with the baseline assay, or both. In an embodiment of a method for improving an assay, an improved assay may comprise a reagent, or reagents, having a greater number of constituents as compared with a corresponding reagent, or corresponding reagents, used in the baseline assay; for example, such an improved assay may require fewer reagents in a mixing step, or fewer mixing steps, as compared with the baseline assay. In an embodiment of a method for improving an assay, an improved assay may comprise a shorter duration detection step, or may initiate a detection step at an earlier time, as compared with the baseline assay. In an embodiment of a method for improving an assay, an improved assay may comprise an optical detection step. In an embodiment of a method for improving an assay, an improved assay may comprise a plurality of detection steps, as compared to the baseline assay; for example, an improved assay comprising a plurality of detection steps may provide detection or quantification of two or more analytes in a sample, or of two or more characteristics of a sample, or of an analyte and a characteristic of a sample.

Methods of improving assays for use in automatic assay devices or automatic assay systems disclosed herein provide advantages of shorter time to assay results, reduced sample volume requirements, reduced assay complexity, reduced assay cost, reduced assay coefficient of variation (e.g., between assay replicates), enhanced ability to coordinate running multiple assays concurrently, enhanced assay reliability, enhanced assay precision, enhanced assay accuracy, and better overall assay performance on automatic assay devices and automatic assay systems. The methods disclosed herein provide strategies for improving existing assays. For example, the methods disclosed herein provide strategies suitable for improving existing assays used on automatic assay devices and systems including automatic assay devices, including devices and systems configured to perform multiple assays, of multiple assay types or targets, on a single sample. These methods provide strategies for reducing the amount of sample required, e.g., for the performance of such multiple assays on a single sample. The methods disclosed herein further provide strategies which can be applied to adapting a manual assay for use on an automated device or system, and which can be applied to adapting an automated assay for use on a new automated device or automated system.

Thus, assay improvements as disclosed herein provide advantages over the baseline assays, including greater speed, improved reliability, increased flexibility of operation, decreased use of reagent, decreased volume of sample, increased comfort for subjects, and increased convenience for laboratory personnel. In addition, assay improvements as disclosed herein provide further advantages, including greater flexibility in scheduling multiple assays concurrently, or partially concurrently; use of diluted samples may allow performance of assays in multiple matrices (e.g., may allow a choice of use of serum, plasma, or whole blood for the performance of improved assays); use of diluted samples may reduce interference by non-analyte sample constituents; use of diluted samples may improve the signal-to-noise ratio in some assays; and other advantages.

Methods of improving assays for use in automatic assay devices or automatic assay systems disclosed herein may be applied to assays performed at a point of service location. For example, the methods disclosed herein may be applied for use on automatic assay devices or automatic assay systems located at a doctor's office, or in a clinic, or in a hospital. For example, the methods disclosed herein may be applied for use on automatic assay devices or automatic assay systems located at a retail location, such as a drugstore, a supermarket, or other location where a subject may wish to provide a sample for analysis. For example, the methods disclosed herein may be applied for use on automatic assay devices or automatic assay systems located in a vehicle, such as, e.g., an ambulance, or fire truck, or other emergency response vehicle; or in a boat, or airplane, or other vehicle.

The challenge of improving an assay, and of adapting an assay for performance on a (new) automated device or automated system, presents innumerable options, so that a nearly limitless sequence of altered steps and conditions may be attempted. The methods disclosed herein provide a focused, directed set of actions to be taken in order to improve an assay, thereby providing limited, and therefore practical, strategies for improving and adapting assays.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
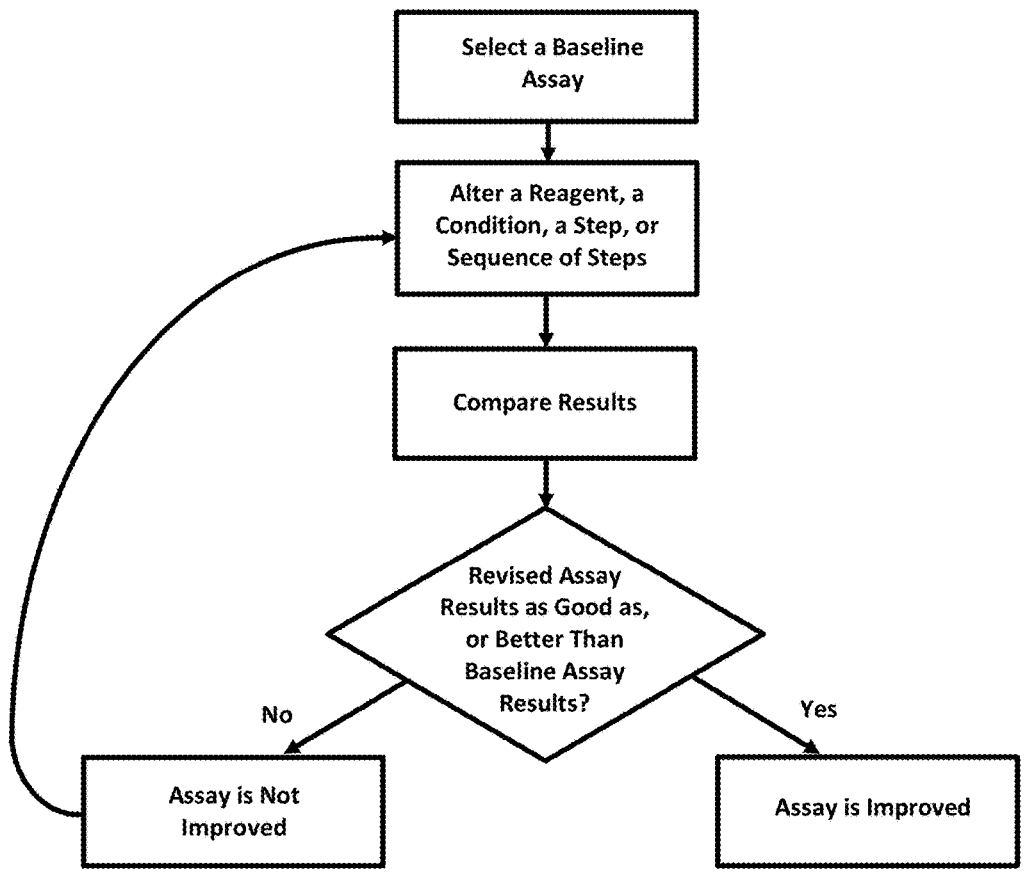
FIG. 1 illustrates an embodiment of the methods disclosed herein, in which a step of a baseline assay is altered, and the results of the performance of the revised assay (including the alteration) are compared to the results of the performance of the baseline assay (not including the alteration in the step). In this figure, and all subsequent figures, arrows indicate the sequence of steps in the embodiments illustrated, with the step at the base end of the arrow preceding the step at the arrow-head end of the arrow; rectangular and square shapes indicate steps to be performed; diamond shapes indicate decision (or "branch") points.

Description and disclosure of examples of methods, and reagents, devices, and systems which may use, or may provide examples of, methods disclosed herein may be found, for example, in U.S. Pat. No. 7,888,125; U.S. Pat. No. 8,088,593; U.S. Pat. No. 8,158,430; U.S. Pat. No. 8,380,541; U.S. Pat. No. 8,435,738; U.S. Pat. No. 8,475,739; U.S. patent application Ser. No. 13/769,798, filed Feb. 18, 2013; U.S. patent application Ser. No. 13/769,779, filed Feb. 18, 2013; U.S. patent application Ser. No. 13/769,817, filed Feb. 18, 2013; U.S. patent application Ser. No. 13/769,818, filed Feb. 18, 2013; U.S. patent application Ser. No. 13/769,820, filed Feb. 18, 2013; U.S. patent application Ser. No. 14/183,503, filed Feb. 18, 2014; PCT/US2012/57155, filed Sep. 25, 2012; U.S. application Ser. No. 13/244,946, filed Sep. 26, 2011; U.S. patent application Ser. No. 13/244,949, filed Sep. 26, 2011; U.S. Application Ser. No. 61/673,245, filed Sep. 26, 2011; U.S. Application Ser. No. 61/903,346, filed Nov. 12, 2013; and U.S. Application Ser. No. 61/858,589, filed Jul. 25, 2013, the disclosures of all of which patents and patent applications are all hereby incorporated by reference in their entireties.

The assays and methods disclosed herein may be performed on a device, or on a system, for processing a sample. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be an automatic assay device. A device may be an automatic assay device. An automatic assay device may be configured to facilitate collection of a sample, prepare a sample for a clinical test, or effect a chemical reaction with one or more reagents or other chemical or physical processing, as disclosed herein. An automatic assay device may be configured to obtain data from a sample. An automatic assay device may be configured to transmit data obtained from a sample. An automatic assay device may be configured to analyze data from a sample. An automatic assay device may be configured to communicate with another device, or a laboratory, or an individual affiliated with a laboratory, to analyze data obtained from a sample.

An automatic assay device may be configured to be placed in or on a subject. An automatic assay device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. An automatic assay device may receive a sample from the subject through a housing of the device. The sample collection may occur at a sample collection site, or elsewhere. The sample may be provided to the device at a sample collection site.

In some embodiments, an automatic assay device may be configured to accept or hold a cartridge. In some embodiments, an automatic assay device may comprise a cartridge. The cartridge may be removable from the automatic assay device. In some embodiments, a sample may be provided to the cartridge of the automatic assay device. Alternatively, a sample may be provided to another portion of an automatic assay device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, an automatic assay device, one or more components of the cartridge may be brought into fluid communication with other components of the automatic assay device. For example, if a sample is collected at a cartridge, the sample may be transferred to other portions of the automatic assay device. Similarly, if one or more reagents are provided on a cartridge, the reagents may be transferred to other portions of the automatic assay device, or other components of the automatic assay device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as an automatic assay device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the automatic assay device. The sample, reagent, or aliquot thereof can be deposited at a location on or within the automatic assay device. Sample and reagent, or multiple reagents, may be mixed using a sample handling system in a similar manner. One or more components of the cartridge may be transferred in an automated fashion to other portions of the automatic assay device, and vice versa.

A device, such as an automatic assay device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

An automatic assay device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. An automatic assay device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

An automatic assay device may be configured to run one or more assay on a sample, and to obtain data from the sample. An assay may include one or more physical or chemical treatments, and may include running one or more chemical or physical reactions. An automatic assay device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

An automatic assay device may be configured to perform a plurality of assays on a sample. In embodiments, an automatic assay device may be configured to perform a plurality of assays on a single sample. In embodiments, an automatic assay device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. An automatic assay device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

An automatic assay device may be configured to detect one or more signals relating to the sample. An automatic assay device may be configured to identify one or more properties of the sample. For instance, the automatic assay device may be configured to detect the presence or concentration of one analyte or a plurality of analytes or a disease condition in the sample (e.g., in or through a bodily fluid, secretion, tissue, or other sample). Alternatively, the automatic assay device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, an automatic assay device may be configured to transmit data obtained from a sample. In embodiments, an automatic assay device may be configured to communicate over a network. An automatic assay device may include a communication module that may interface with the network. An automatic assay device may be connected to the network via a wired connection or wirelessly. The network may be a local area network (LAN) or a wide area network (WAN) such as the Internet. In some embodiments, the network may be a personal area network. The network may include the cloud. The automatic assay device may be connected to the network without requiring an intermediary device, or an intermediary device may be required to connect an automatic assay device to a network. An automatic assay device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

An automatic assay device may provide data regarding a sample to, e.g., a health care professional, a health care professional location, such as a laboratory, or an affiliate thereof. One or more of a laboratory, health care professional, or subject may have a network device able to receive or access data provided by the automatic assay device. An automatic assay device may be configured to provide data regarding a sample to a database. An automatic assay device may be configured to provide data regarding a sample to an electronic medical records system, to a laboratory information system, to a laboratory automation system, or other system or software. An automatic assay device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by an automatic assay device, or analysis of such data, or reports, may be provided to a database, an electronic medical records system, to a laboratory information system (LIS), to a laboratory automation system (LAS), or other system or software.

Exemplary automatic assay devices, and systems including such automatic assay devices, are disclosed, for example, in U.S. Pat. No. 8,088,593; U.S. Pat. No. 8,380,541; U.S. Pat. No. 8,435,738; U.S. Pat. No. 8,475,739; U.S. patent application Ser. No. 13/769,817, filed Feb. 18, 2013; U.S. patent application Ser. No. 13/769,818, filed Feb. 18, 2013; U.S. patent application Ser. No. 13/769,820, filed Feb. 18, 2013; and U.S. patent application Ser. No. 14/183,503, filed Feb. 18, 2014, all of which are incorporated by reference herein.

DEFINITIONS

Before the present methods, devices, and systems are disclosed and described, it is to be understood that the terminology used herein is for the purpose of describing particular embodiments only and is not intended to be limiting. It is also to be understood that the present disclosure provides explanatory and exemplary descriptions and examples, so that, unless otherwise indicated, the devices, systems, and methods disclosed herein are not limited to the specific embodiments described herein. References cited herein are hereby incorporated by reference in their entirety, except to the extent that they conflict with teachings explicitly set forth in this specification.

It must be noted that, as used in the specification and the appended claims, the singular forms "a," "an" and "the" include plural referents unless the context clearly dictates otherwise. Thus, for example, reference to "a sample" refers to a single sample or multiple samples, including multiple kinds of samples.

Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

Acronyms and abbreviations, such as "min" (minute), "sec" (second), "rpm" (revolutions per minutes), and so forth, have their customary meanings. As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

The term "nucleic acid" refers to nucleotides and nucleosides which make up, for example, deoxyribonucleic acid (DNA) macromolecules and ribonucleic acid (RNA) macromolecules, including particular types of such molecules (e.g., complementary DNA (cDNA); messenger RNA (mRNA); transfer RNA (tRNA); micro RNA (miRNA); and other forms of DNA and RNA). Nucleic acids may be identified by the base attached to the sugar (e.g., deoxyribose or ribose); as used herein, the following abbreviations for these bases are used to represent nucleic acids in sequence listings identifying and describing their structures (either upper-case or lower-case may be used).

TABLE 1A

| Base (in Nucleic Acid) | Letter Code |
|---|---|
| Adenine | A |
| Thymine | T |
| Guanine | G |
| Cytosine | C |
| Uracil | U |

As used herein, a "nucleic acid" refers to any polynucleotide (i.e., any polymeric chains containing two or more nucleotides), including primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3" terminus) of the chain.

"Stringency" of hybridization reactions is readily determinable by one of ordinary skill in the art, and generally is an empirical calculation dependent upon probe, length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1. % Ficoll/0.1% polyvinylpyrrolidone/50 mM sodium phosphate buffer at pH 6.5 with 750 mM sodium chloride. 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C. with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% Formamide, 5×SSC (150 mM NaCl, 15 mM trisodium citrate). 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

A "primer" as used herein refers to a polynucleotide which is i) capable of hybridizing to nucleic acid strand containing a nucleic acid template and ii) acting as a point of initiation for the synthesis of a new nucleic acid strand, wherein the new nucleic acid strand is an extension product of the primer and is complementary to a template strand. A primer may have a free —OH group at its 3' terminus, which may serve as the origin of synthesis for the extension product.

The term "ligase" as used herein refers to an enzyme that catalyzes the formation of phosphodiester bonds between nucleotides, typically between the 5' phosphate of one nucleotide, and the 3' hydroxyl group of another nucleotide. Nucleic acid ligases include E. coli DNA ligase, Taq DNA ligase, T3 DNA ligase, T4 DNA ligase, T7 DNA ligase, Ampligase™, T4 RNA ligase 1, and T4 RNA ligase 2. In order to catalyze the ligation reaction, certain ligases require ATP (e.g. T4 DNA ligase) or NAD+(E. coli DNA ligase).

A polymerase may generate an extension product of a primer. The primer and extension product thereof may be complementary to a template nucleic acid strand. Generally, a polymerase will initiate synthesis of an extension product of a primer at the 3' end of the primer. In some embodiments, a polymerase provided herein may have strand displacement activity. Polymerases having strand displacement activity include, for example, exo-Bca DNA polymerase, phi29 DNA polymerase, Klenow Fragment of E. coli DNA Polymerase I, Vent$_R$ DNA polymerase, Deep VentR DNA polymerase, 9° N$_m$ DNA polymerase, and Large Fragment of Bst DNA Polymerase.

Restriction enzymes generally cut double-stranded nucleic acids at or near a specific nucleotide sequence (a "restriction enzyme recognition sequence"). In some embodiments, a restriction enzyme provided herein is thermostable.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol. 51:263 (1987); Erlich, ed., PCR Technology (Stockton Press, NY, 1989).

The term "transfection" refers to the uptake of foreign DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

As used herein, "complementary" sequences refer to two nucleotide sequences which, when aligned anti-parallel to each other, contain multiple individual nucleotide bases which pair with each other. Sequences may be considered "complementary" when the total lengths of the two sequences are significantly different from each other.

The terms "polypeptide" and "protein" may be used interchangeably to refer to molecules comprised of amino acids linked by peptide bonds. Individual amino acids may be termed "residues" of a polypeptide or protein. The amino acid sequences of polypeptides may be presented as a string of letters, where the letters have the following meanings:

TABLE 1B

| Amino Acid | 3-Letter Code | 1-Letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "Relative Light Units" and its abbreviation "RLU" refer to the units used to scale the output of instruments which measure light intensity (e.g., a photomultiplier tube, luminometer, or other such instrument or device). RLU values are typically proportional to photon number; reporting light intensity in RLU allows comparison between experiments and between instruments.

As used herein, the term "coefficient of variance" and its abbreviations "COV" and "CV" are used as commonly understood in the art; COV values are typically reported as a percent. The COV is calculated by dividing the standard deviation (SD) of a set of experimental values by the mean value (M) of that set of experimental values to obtain the ratio of the standard deviation to the mean, and then multiplying that ratio by 100:

$$COV = SD/M \times 100$$

The COV provides a measure of the differences between observed measurement values where multiple experiments and measurements are made; where multiple experiments give widely varying results, the COV is large; where multiple experiments give results that are all closely matched, the COV is small. A small COV for the results of an experimental procedure indicates that the experimental procedure provides consistent results; this is typically interpreted to mean that a small COV indicates better results than a larger COV.

As used herein, a "buffer" is a compound or group of compounds which, in solution, tend to maintain the pH of the solution at or near a particular value. A composition may include a buffer. For example, phosphate salts may be used as buffers in compositions where the pH is to be maintained near physiological levels. Phosphate salts include $NaH_2PO_4$, $Na_2HPO_4$, and $Na_3PO_4$. Buffers may include, without limitation, phosphate, citrate, ammonium, acetate, carbonate, tris(hydroxymethyl)aminomethane (TRIS), 3-(N-morpholino) propanesulfonic acid (MOPS), 3-morpholino-2-hydroxypropanesulfonic acid (MOPSO), 2-(N-morpholino) ethanesulfonic acid (MES), N-(2-Acetamido)-iminodiacetic acid (ADA), piperazine-N,N'-bis(2-ethanesulfonic acid) (PIPES), N-(2-Acetamido)-2-aminoethanesulfonic acid (ACES), cholamine chloride, N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 4-(2-hydroxyethyl)-1-piperazine ethanesulfonic acid (HEPES), acetamidoglycine, tricine (N-(2-Hydroxy-1,1-bis (hydroxymethyl)ethyl)glycine), glycinamide, and bicine (2-(Bis(2-hydroxyethyl)amino)acetic acid) buffers. Buffers include other organic and inorganic acid buffers in addition to the phosphate, citrate, ammonium, acetate, and carbonate buffers explicitly mentioned herein.

As used herein, the term "small molecule" refers to a compound, typically a non-polymeric organic compound, that is smaller than a typical protein. Examples of small molecules include acetylsalicylic acid (aspirin), caffeine, cholesterol, vitamin D, and other molecules. A small molecule typically has a molecular weight below about 500 Daltons. As used herein, small molecules may be small organic molecules, and may be small inorganic molecules.

"Antibodies" (Abs) are glycoproteins that exhibit binding specificity to a specific (target) antigen.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. For example, monoclonal antibodies may be made by the hybridoma method first described by Kohler et al., Nature, 256:495 (1975), or may be made by recombinant DNA methods (see, e.g., U.S. Pat. No. 4,816,567 to Cabilly et al.).

As used herein, an "antigen-binding antibody fragment" is any antibody fragment that retains the ability to bind to the specific target to which the intact antibody specifically binds. An antigen-binding antibody fragment may have different (e.g., lesser) binding affinity for the target antigen than the intact antibody. Examples of antibody fragments include Fab, Fab', Fab'-SH, F(ab')2, Fd, Fc, Fv, diabodies, and any other "Non-single-chain antigen-binding unit" as described, e.g., in U.S. Pat. No. 7,429,652. "Diabodies" are small antibody fragments with two antigen-binding sites, which fragments comprise a heavy chain variable domain connected to a light chain variable domain in the same polypeptide chain.

An antibody that "specifically binds to" or is "specific for" a particular polypeptide or, an epitope on a particular polypeptide is one that binds to that particular polypeptide or epitope on a particular polypeptide without substantially binding to any other polypeptide or polypeptide epitope.

An "epitope" is a term well understood in the art and means any chemical compound, or part thereof, that exhibits specific binding to an antibody.

An "antigen" is a material or molecule that contains an epitope, and, as such, also specifically binds to antibody. The terms "antigen", "target molecule", "target polypeptide", "target epitope", and the like are used herein to denote the molecule specifically bound by an antibody or antibody fragment.

As used herein, the terms "CDR" and "complementarity-determining region" are used interchangeably to refer to one or more of the variable regions of an antibody light chain (or fragment thereof) or of an antibody heavy chain (or fragment thereof) in which the amino acid sequence may differ between different antibodies, and which contributes greatly to the specificity of antibody binding to a specific target molecule.

As used herein, the term "general chemistry assay" refer to an assay for an element or compound which may be found in a sample (e.g., a biological sample) using chemical or physical reactions to detect the presence of, and, if desired, to quantify the amounts of, an analyte in a sample. A general chemistry assay may be directed at detecting a small molecule analyte (as defined above, and including ions and elements such as sodium and potassium), or directed at a chemical characteristic of a sample (e.g., pH, $O_2$ saturation, or other sample characteristic determined by chemical or physical means). Some general chemistry assays may include specific binding by, e.g., metal ions, or even antibodies (e.g., agglutination and hemagglutination assays), but general chemistry assays typically do not depend on antibody recognition of the target analyte.

As used herein, the term "immunoassay" refers to assays which utilize antibodies (including antibody fragments) and their binding to target molecules to label, identify, quantify, or otherwise provide information regarding the presence, amounts, and properties of target molecules and samples containing them. One useful immunoassay is an ELISA (Enzyme-Linked ImmunoSorbent Assay). Immunoassays also include, for example, competitive binding assays, sandwich assays, Western blots, and other assays utilizing antibodies and antibody fragments.

As used herein, the term "nucleic acid assay" refers to any and all assays which utilize nucleic acids or which detect nucleic acids in a sample. Nucleic acids hybridize to complementary nucleic acids, a property which is useful for identifying target nucleic acids, and for identifying samples, whether fluid, tissue, or other samples, containing target nucleic acids. Nucleic acid assays use, and include, techniques for amplifying target nucleic acids (e.g., by producing copies of target nucleic acids, or copies of nucleic acids that are complementary to target nucleic acids). Nucleic acid assays include, for example, assays using polymerase chain reaction (PCR), Southern blots, Northern blots, and other assays which may identify and allow detection of nucleic acids in a sample.

As used herein, the term "receptor-based assay" refers to an assay which utilizes, or detects, the binding of a receptor to its ligand, or the dissociation of a ligand from its receptor. Such assays may use the binding directly to detect or quantify the presence or amount of a receptor or ligand, may use competitive binding techniques to detect or quantify the presence or amount of a target molecule in a sample, or may detect or quantify the presence or amount of a target by use of other methods based on binding between a receptor and ligand or ligands.

As used herein, the term "enzymatic assay" refers to an assay which utilizes, or detects, the presence or action of an enzyme. For example, an assay which provides a substrate for a target enzyme, and detects the presence of that enzyme, or quantifies the activity of that enzyme in a sample following addition of the substrate is an enzymatic assay. An assay which utilizes the enzymatic production of a detectable substance is another example of an enzymatic assay; for example, colorimetric assays (e.g., in which a detectable product is produced by an enzyme, which may be an endogenous enzyme or which may be supplied with the assay reagents) such as assays in which horseradish peroxidase or alkaline phosphatase is used to produce a colored product as an indicator of the progress of the reaction or presence of a target, are enzymatic assays.

As used herein, the term "bound" means that two compounds are in a tight, non-covalent, interaction with one another. Each compound is bound to the other. Binding may be specific: for example, when a ligand is in contact with its receptor, the ligand is said to be bound to the receptor, and when an antigen is in contact with an antibody specific for that antigen, the antigen is said to be bound to the antibody. The term "bound" is typically used to refer to specific binding between binding partners. Compounds which bind are said to "associate" with each other, and the rate of binding is the association rate.

As used herein, the term "unbound" refers to a compound that is not in a tight, non-covalent, interaction with another compound. Typically, the term "unbound" refers to the lack of specific binding between potential binding partners. For example, where antigens and antibodies are present in a solution, an antigen molecule that is free in the solution is said to be an unbound antigen. The rate of unbinding is the dissociation rate.

It will be understood that binding between partners may be transient, so that there may be continuous binding and unbinding between compounds that bind each other; however, an equilibrium may be reached where the numbers of bound and unbound compounds remain substantially constant for a period of time.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner molecule Y can generally be represented by the equilibrium dissociation constant ($K_D$). The equilibrium dissociation constant $K_D$ is typically provided in units of moles; for a bimolecular binding reaction between molecule X and molecule Y, the $K_D$ is that concentration of molecule X where 50% of X molecules are bound to Y molecules. Affinity can be measured by common methods known in the art, including those described herein. For example, the binding affinity of an antibody can be determined by the Scatchard analysis of Munson et al., Anal. Biochem., 107:220 (1980). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. The binding affinity of the monoclonal antibody can, for example, be determined by the Scatchard analysis of Munson et al., Anal. Biochem., 107:220 (1980).

"Affinity" of an antibody for an epitope to be used in the treatment(s) described herein is a term well understood in the art and means the extent, or strength, of binding of antibody to epitope. Affinity may be measured and/or expressed in a number of ways known in the art, including, but not limited to, equilibrium dissociation constant ($K_D$) and $IC_{50}$ (amount needed to effect 50% inhibition in a competition assay). It is understood that an affinity as discussed herein is an average affinity for a given population of antibodies which bind to an epitope. Values of KD' reported herein in terms of mg IgG per mL or mg/mL indicate mg IgG per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

As used herein, the term "competitive binding" refers to situations where multiple potential binding partners are present in the same solution, where some potential binding partners bind together and others remain free in solution. The multiple binding partners may include a single population of substantially identical compounds (e.g., ligands or antigens) which may bind with a target binding partner (e.g., a receptor or antibody), or may include two or more populations of potential binding partners (e.g., ligands or antigens), each of which population may bind with a target binding partner (e.g., a receptor or antibody). For example, where multiple antigens bind a single antibody, the antigens are said to "cross-react" with the antibody, and may be termed "cross-reactants" with respect to that antibody. In some cases, one population which binds may be labeled, and another population may be unlabeled.

As used herein, the terms "competition assay", "competition methods", "competitive binding assays" and the like refer to assays and methods in which an analyte and a labeled molecule that is believed to be nearly identical to the analyte (with respect to its binding characteristics) are present in a solution with a molecule which binds both the analyte and the labeled molecule (e.g., an antibody). Competitive binding assays rely on the ability of a labeled molecule to compete with the analyte for binding with a limited amount of labeled molecules. The amount of analyte in the test sample is inversely proportional to the amount of labeled molecule that becomes bound to the molecule which binds both the analyte and the labeled molecule.

Sandwich assays involve the use of two antibodies, each capable of binding to a different immunogenic portion, or epitope, of the analyte to be detected. In a sandwich assay, the test sample analyte is bound by a first antibody which is immobilized on a solid support, and thereafter a second antibody binds to the analyte, thus forming an insoluble three part complex (see, e.g., U.S. Pat. No. 4,376,110). The second antibody may itself be labeled with a detectable moiety (direct sandwich assays), or may be measured using an anti-immunoglobulin antibody that is labeled with a detectable moiety (indirect sandwich assay). For example, one type of sandwich assay is an ELISA assay, in which case the detectable moiety is an enzyme.

As used herein, the terms "sample" and "biological sample" refer equally to any fluid, tissue, or other material collected from a subject. As used herein, regardless of the material or source of the sample, the terms "sample" and "biological sample" include aliquots, portions of a sample (including portions provided by separation, filtration, coagulation, centrifugation, or other treatments), dilutions, mixtures comprising a sample or portion of a sample, and other compositions including at least a part of the sample. A sample may be, but is not limited to, a blood sample, a urine sample, or a portion of such a sample. Examples of biological samples include but are not limited to, blood, serum, plasma, a nasal swab, a nasopharyngeal wash, saliva, urine, gastric fluid, cerebrospinal fluid, fluid obtained from a spinal tap, tears, stool, mucus, sweat, earwax, oil, a glandular secretion, semen, vaginal fluid, interstitial fluid, ocular fluids, a throat swab, tissue, breath, hair, finger nails, skin, biopsy samples, placental fluid, amniotic fluid, cord blood, lymphatic fluid, fluid from a body cavity, sputum, pus, microbiota, meconium, breast milk and other secretions and excretions. Biological samples may include nasopharyngeal wash, or other fluid obtained by washing a body cavity or surface of a subject, or by washing a swab following application of the swab to a body cavity or surface of a subject. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be provided from a human or animal. The sample may be provided from a mammal, vertebrate, such as murines, simians, humans, farm animals, sport animals, or pets. The sample may be collected from a living or dead subject. The sample may be collected fresh from a subject or may have undergone some form of pretreatment, storage, or transport.

A sample may be of any suitable size or volume, and is preferably of small size or volume. In some embodiments of the assays and methods disclosed herein, measurements may be made using a small volume sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 125 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

The terms "plasma" and "blood plasma" refer to the liquid portion of blood (e.g., a blood sample) that remains after the removal of blood cells. Red blood cells and white blood cells may be removed by centrifugation of a blood sample, leaving plasma above the pelleted cells in the bottom of the centrifuge tube. Plasma retains blood clotting factors, and is obtained from anti-coagulated blood samples.

The terms "serum" and "blood serum" refer to the liquid portion of blood that remains after blood is allowed to clot, and the clot is removed. Serum differs from plasma in that serum lacks clotting factors: since clotting requires fibrin, thrombin, and other proteins, which form and remain part of a blood clot, serum lacks these proteins while plasma contains them.

As used herein, a "finger-stick" refers to: i) the act of making a small puncture in the skin of a subject, allowing a small amount (e.g., a droplet, or one, two, or a few drops) of blood to flow and become available for collection; ii) the puncture itself; and iii) the blood collected thereby. Blood may be liberated in a finger-stick, for example, by use of a lancet or other sharp implement effective to pierce the skin of a subject. In some cases, active methods may be used to extrude more blood from the subject that would otherwise be obtained from the finger-stick (e.g., by massage or other manipulation of the area near the site of the finger-stick). Typically, only a small amount of blood is collected in this way (e.g., the amount of blood may be about 250 µL or less, or about 200 µL or less, or about 150 µL or less, or about 100 µL or less, or about 50 µL or less, or about 25 µL or less, or about 15 µL or less, or about 10 µL or less, or about 10 µL or less, or about 5 µL or less, or about 3 µL or less, or about 1 µL or less). Blood from a finger-stick may be collected, e.g., by needle, syringe, capillary tube, or other method. Blood from a finger-stick may be collected for transport to another location; for storage prior to use or analysis; for immediate use; or for a combination of the same.

When referring to a volume, e.g., a "finger-stick volume" or "the volume of a finger-stick", the term "finger-stick" refers to the volume of a few droplets of blood typically obtained from a finger-stick. A single droplet of blood may have a volume of about 20-50 µL, e.g., about 40 µL. Thus, a few droplets of blood obtained from a finger-stick provide a volume of about 75 µL to about 150 µL, or, in some instances, between about 100-150 µL. Advantages of obtaining blood from a finger-stick include minimal discomfort to the subject and ease of access, as compared to obtaining blood from a vein or artery.

As used herein, the terms "characteristic" of a sample, and "sample characteristic" refer to properties of a sample that can be detected, identified, or quantified, by an assay. Such properties include, without limitation, pH; osmolarity; ionic strength; temperature; partial pressure; hematocrit of a blood sample; optical characteristics such as absorbance, transmittance, turbidity, reflectance, optical rotation, polarization, and any other optical characteristic; specific gravity; conductivity; and other bulk and material properties. Characteristics include particular characteristics, such as the presence or absence, or abundance, of classes of molecules (e.g., IgA, IgD, IgE, IgG, and IgM molecules) or particular molecules (e.g., particular hormones, drugs, drug metabolites, metabolites of naturally occurring molecules, cell surface markers, nucleic acids having specific sequences), and other characteristics.

As used herein, the term "analyte" refers to a target in a sample that is to be detected or quantified by an assay. Equivalently, an analyte may be termed a "target" and may be termed a "target analyte." An analyte may be an atom, ion, radical, or compound, or a complex including any one or more of these. For example, analytes which may be targeted in an assay include, without limitation, organic molecules (e.g., "small molecules" such as drugs or drug metabolites, vitamins, lipids, sugars, and other molecules); inorganic targets such as, e.g., sodium, iron, iodine, phosphate, nitric oxide, and other elements and compounds; peptides and proteins, including hormones, growth factors, transport proteins, and receptors; nucleic acids; small molecules, nucleic acids and antigenic targets derived from infectious agents such as viruses and bacteria; and other analytes.

As used herein, the term "composition" refers to a substance containing at least two ingredients; for example, a composition may be a solution (e.g., an aqueous mixture comprising water and one or more ingredients); may be a dry mixture, which may have been provided by drying (e.g., lyophilizing or dessicating) a solution, or may be mixed from dry ingredients; may be an emulsion or slurry; may be a suspension; may be a mixture that is incompletely dissolved or incompletely mixed; or may include other forms or combinations of ingredients.

A composition may include one or more active ingredients and may also include one or more carrier(s); carriers include physiologically acceptable carriers. For example, a physiologically acceptable carrier may be an aqueous pH buffered solution. Examples of carriers, such as physiologically acceptable carriers, include buffers such as phosphate, citrate, and other organic acids as discussed above; antioxidants including ascorbic acid; low molecular weight (less than about 10 residues) polypeptides; proteins, such as, e.g., serum albumin, gelatin, cytochromes, and immunoglobulins; hydrophilic polymers such as polyvinylpyrrolidone; amino acids such as glycine, glutamine, asparagine, arginine or lysine; monosaccharides, disaccharides, polysaccharides, and other carbohydrates including glucose, mannose, and dextrins; chelating agents such as ethylene diamine tetraacetic acid (EDTA); sugar alcohols such as mannitol or sorbitol; salt-forming counterions such as sodium, potassium, calcium, magnesium and others; nonionic surfactants such as TWEEN™, polyethylene glycol (PEG), and PLURONICS™; and/or other compounds known in the art.

For example, a composition may include albumin, gelatin, cytochrome C, an immunoglobulin, an amino acid, agar, glycerol, ethylene glycol, a protease inhibitor, an antimicrobial agent, a metal chelating agent, a monosaccharide, a disaccharide, a polysaccharide, a reducing agent, a chelating agent, or combinations thereof.

As used herein, the term "assay" refers to a method for identifying, or for quantifying the amount of, a substance or substances in a sample. An assay may include physical or mechanical manipulation of a sample, including, e.g., dividing a sample into two or more portions; transporting a sample, or portion of a sample, from one location to another; heating or cooling a sample or portion of a sample; stirring or agitating a sample or portion of a sample; and other steps. An assay will typically include sample treatment steps, such as, e.g., one or more of dilution, centrifugation, filtration, agglutination, sedimentation, coagulation, separation, and other steps. An assay will typically include sample treatment steps which may include reactions between reactants in a reagent, or may include reactions between reactants and an analyte in a sample, or both; for example, such sample treatment steps may include nucleic acid probe hybridization to a target nucleic acid sequence; antibody binding to a target antigen or antigenic epitope; small molecule binding to a target analyte; binding between a ligand and a receptor; enzymatic action involving an enzyme and a substrate; and other reactions. An assay may include steps comprising incubating a sample under incubation conditions, or incubating a sample with a reagent, or other incubation step. An assay will typically include steps which allow the labeling of a target analyte or other constituent in a sample or reagent. An assay will typically include steps which allow the detection of a target analyte, if present in a sample; such detection steps may include optical detection, biochemical detection, electrochemical detection, enzymatic detection, and other forms of detection, and combinations thereof.

As used herein, the term "end-point assay" refers to an assay having a detection step as a final step; that is, the assay measurements are performed at the end of a period of time, and those measurements determine, e.g., the concentration of an analyte, or whether or not the analyte is indeed present or not in the sample. The period of time may be an incubation time (e.g., a period of time during which a sample let settle, or is in contact with a reagent) or a reaction time (e.g., a period of time during which a chemical or physical reaction is allowed to proceed); it will be understood that the period of time may comprise both an incubation time and a reaction time, and may comprise other times as well.

As used herein, the term "kinetic assay" refers to an assay having a plurality of detection steps (one of which may comprise a final step); that is, the assay measurements are performed at two or more times during the assay. Typically, such measurements allow the measurement and/or calculation of a difference between an initial measurement and a later measurement, which may be used to determine, for example, the difference between the value obtained in an initial measurement and the value obtained at a later time. Such differences, for example, may be used to determine a rate of change in the measurement. These measurements may be used to determine the concentration of an analyte, or whether or not the analyte is indeed present or not in the sample, or for other purposes.

Assays may utilize end point measurements alone; or may utilize kinetic measurements alone; or may utilize both end point and kinetic measurements in performance of an assay. An assay may be directed to the determination of whether or not an analyte is present in the sample, or to the determination of a concentration of an analyte in a sample. An assay may be directed to the determination of whether or not an analyte is present in a sample, and to the determination of the concentration of an analyte in a sample. An assay may be directed to determining these, or other measurements, for two or more analytes in a sample.

As used herein, the term "reacting" refers to combining two or more materials (e.g., mixing together two solutions having different compositions) so that a reaction occurs. Such reactions include chemical reactions (e.g., covalent or other bonds may be formed, or broken, or both); physical reactions (e.g., two materials may mix without altering any chemical bonds), combinations of these (e.g., a dye may label a cell), or other reactions.

As used herein, the term "reactant" refers to an ingredient that interacts with an analyte or with another ingredient in a sample or composition. Such interactions are typically covalent or hydrogen-bonding interactions; however, reactants may also interact with targets and other compounds by ionic, dipole, hydrophobic, hydrophilic, van der Waals, and other interactions, in addition to, or in conjunction with, covalent interactions and hydrogen-bond interactions.

As used herein, "reactants" include, without limitation, acids, bases, small molecules, enzymes and other catalysts, substrates, cell membrane receptors, nucleic acid probes, antibodies (including monoclonal antibodies and antisera) reactive with a specific analyte, dyes, and other ingredients. Various commercially available reactants such as a host of polyclonal and monoclonal antibodies specifically developed for specific analytes can be used. For examples, a chemical reaction may occur between a sample containing an analyte and an immobilized reactant, that may cause an analyte to bind to a surface. The unbound analytes may be washed away. In some embodiments, a reaction may cause the emission of an optical signal, light, or any other sort of signal. If unreacted reactants remain in the proximity, they may cause interfering background signal. It may be desirable to remove the unreacted reactants to reduce interfering background signal and permit the reading of the bound analytes. In some instances, the wash solution does not cause a chemical reaction to occur between the wash solution and the sample.

Reactants known in the art typically include functional groups, which include, without limitation, amino, carboxyl, thiol, aldehyde, peroxide, hydroxyl, and other groups. Reactants may include Diels-Alder reactants. It will be understood that other chemically reactive groups or reaction centers may be present in or on a reactant as well. Reactants may include crosslinking agents, such as, e.g., formaldehyde, glutaraldehyde, and others, which may link with ethylene glycol oligomers, diamines, amino acids, and other groups. For example, reactants include, but are not limited to: an antibody directed at a target compound; a nucleic acid probe complementary to a target nucleic acid sequence; a dye which interacts with a target cell or cellular marker; a compound which binds to an antibody or to a nucleic acid probe; an enzyme that catalyzes a reaction; a substrate which aids in a reaction; a compound which reacts with another compound to provide a colored or fluorescent product; a ligand recognized by a receptor; a receptor molecule which binds a ligand; a material which aids a reaction; and other compounds and materials.

As used herein, the term "reagent" refers to compositions including reactants, which may react with, bind to, or otherwise interact with an analyte in a sample, or which may aid in the detection of an analyte or in the detection of interactions between an analyte and other reagents. Reagents may further include ingredients that do not directly, or do not significantly, react with other elements in the composition or sample, but may be useful as diluents, solvents, stabilizers, preservatives, anti-oxidants, buffers, osmoticants, bulking agents, separation agents, or have other useful properties.

Reagents may include, without limitation, wash buffers, enzyme substrates, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies, or other materials necessary to run an assay on a device. An enzyme-labeled antibody conjugate may include a polyclonal antibody or a monoclonal antibody, the antibody being labeled with an enzyme that can yield a detectable signal upon reaction with an appropriate substrate. Non-limiting examples of such enzymes are alkaline phosphatase and horseradish peroxidase. In some embodiments, the reagents comprise immunoassay reagents. Reagents defining assay specificity may be provided, which may optionally include, for example, monoclonal antibodies, polyclonal antibodies, proteins, nucleic acid probes or other polymers such as affinity matrices, carbohydrates or lipids.

As used herein, the terms "diluting", "to dilute", and the like refer to the addition of one solution to another. Typically the added solution lacks one or more constituents found in the other solution, so that dilution typically results in a diminution of the concentration of that constituent in the resulting combined solution.

Thus, a reagent that is, or may be used as, a "diluent" is one which is, e.g., useful for increasing the volume of a sample, or portion of a sample, or is useful for the preparation of a liquid formulation, such as a formulation reconstituted after lyophilization, or for adding to a sample, solution, or material for any other reason. In embodiments, a diluent may be buffered (e.g., to have a pH near pH 7, or near pH 7.4, or other desired pH), and may be pharmaceutically acceptable (safe and non-toxic for administration to a human). A diluent typically does not react with, or bind to, an analyte in a sample. Water may be a diluent, as may be an aqueous saline solution, a buffered solution, a solution containing a surfactant, or any other solution. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

As used herein, the terms "pre-treating", "pre-treatment", and the like refer to the performance of assay steps on a sample or sample portion prior to contacting the sample (or portion thereof) with a reagent specific for an analyte. Thus, sample pre-treatments typically prepare a sample for one of many assays for specific target analytes, but are not themselves directed to individual analytes. Centrifugation of a sample is an example of a sample pretreatment. Separation of blood into plasma or serum, and a portion containing blood cells, is another example of pretreatment of a sample. A pre-treatment step may include contacting a sample with a reagent; for example contacting a whole blood sample with heparin or ethylene diamine tetra-acetic acid (EDTA) is a typical blood sample pre-treatment. A pre-treatment step may include contacting a sample with mechanical or other agents; for example contacting a whole blood sample with antibody-coated magnetic beads (effective to adhere red blood cells to the beads) is a typical blood sample pre-treatment. For example, reagents useful for pretreatments applied in some assays to blood samples include, without limitation, white cell lysis reagents, reagents for liberating analytes from binding factors in the sample, enzymes, and detergents. Where possible, pretreatment reagents may be added to a diluent in order to combine a pretreatment step with a dilution step, in order to 1) simplify or eliminate pretreatment steps, and 2) combine steps to reduce the number of steps in an assay.

Assay steps applied to a sample and which occur prior to detection steps may be termed "treatment steps." Thus, actions taken which affect a sample in its location, form, state, volume, composition, or other characteristic, and actions in which a reactant interacts with a sample or portion or constituent of a sample, are all treatment steps. Those treatment steps which occur prior to a step in which a reactant is added to a sample may be termed "pretreatment steps" and comprise a subset of treatment steps. For example, where a sample is divided into two portions, and one portion is centrifuged, and then an antibody is added to the supernatant obtained from the centrifuged portion of the sample, the steps of dividing the sample into portions; centrifuging a portion of the sample; and obtaining the supernatant of the centrifuged portion are "pretreatment" steps. In this example, adding an antibody which binds a target analyte to the supernatant portion effective to label the target analyte would be a treatment step.

As used herein, a "post-treatment" step is a step that occurs following a treatment step; for example, steps which follow the addition of a reactant to a portion of the sample to label a target analyte are termed post-treatment" steps as they occur after the "treatment" of labeling the target analyte. Examples of post-treatment steps include fixing a sample; removing non-target material from a sample; and disposing of all or a portion of a sample or associated reagents following measurement or use of the sample.

As used herein, the terms "aliquot", "aliquotting", and the like refer to removing a portion of a sample from a larger portion of the sample, or from the complete sample. An aliquot, once removed, is typically placed into or in contact with, a reagent, or a diluent, or other solution or material.

As used herein, the term "transporting" refers to physical or mechanical movement of an object (e.g., an aliquot of a sample) from one location to another.

As used herein, the terms "mixing", "to mix" and the like refer to contacting two or more materials (e.g., solutions, such as a sample and a reagent) effective that the materials combine to form a substantially homogeneous solution comprising some or all elements of each original material. (The result of such a combination is a mixture even if some constituents precipitate, or otherwise remain separated from the remaining combined solution.) Mixing may be aided by mechanical action, such as by stirring, agitation of a vessel containing the materials, or other action. Heating may also aid mixing in some instances.

As used herein, the terms "incubating", "to incubate" and the like refer to the step or act of allowing an action to proceed, or a sample, or mixture, to remain in contact with each other, for a period of time. The period of time is termed an "incubation period." Typically, a time-dependent action or reaction occurs and proceeds during an incubation period (e.g., a reaction will proceed during an incubation period following the combination of an enzyme and its substrate in a solution). For example, a period of time following the addition to a sample of a reagent containing a dye, during which the dye may label cells in the sample, is an incubation period. For example, a period of time during which cells in a blood sample settle to the bottom of a vessel, following the introduction of the blood sample into the vessel, is an incubation period.

As used herein, a "separation step" refers to a step in an assay which is useful for separating a sample into two or more constituent portions. Separation steps may include, for example, centrifugation steps; filtration steps; coagulation steps; extraction steps (e.g., where hydrophobic and hydrophilic portions of a sample may be separated by extraction using a solvent); chromatographic steps; electrophoretic steps; and other steps. Separation may be accomplished using magnetic beads; thus, a separation step may include application of magnetic beads to a sample, and may include applying a magnet to a sample comprising magnetic beads. A separation step may be a pretreatment step, or may be a treatment step, a post-treatment step, or other step.

As used herein, the term "separation agent" refers to an agent, which may comprise a reagent, which is useful for separating a sample into two or more constituent portions. Examples of separation agents include magnetic beads (e.g., magnetic beads coated with antibodies, nucleic acids, or other agents which recognize and bind targets), filters, coagulants, precipitants, chromatographic materials, and other materials which may bind or attract a portion of a sample, and which may be localized effective to separate one portion of a sample from another portion of the sample.

As used herein, a "marker", a "label", a "marker moiety" and a "label moiety" refer to a detectable compound or composition which is conjugated directly or indirectly to the antibody so as to generate a "labeled" antibody. A label or marker provides a detectable signal for at least the time period during which a signal is to be observed. The label or marker may be detectable by itself (e.g. radioisotope labels or fluorescent labels) or, in the case of an enzymatic label, may catalyze chemical alteration of a substrate compound or composition which is detectable.

A label or marker moiety may be, for example, a dye, an epitope tag, a fluorescent moiety, a luminescent moiety, a chemiluminescent moiety, an enzymatic label, a magnetic label, a paramagnetic label, a contrast agent, a nanoparticle, a radioisotope, biotin, streptavidin, and a quencher. A nanoparticle may be a particle of an element, such as a gold nanoparticle, or of an alloy or compound, such as a quantum dot (a particle of a semiconductor material), or other particle having a size typically in a range between about 1 nm to about 100 nm. An epitope tag may be, for example, a FLAG® epitope tag, a His tag (e.g., a series of histidine residues), a biotin-recognizable tag (e.g., a biotin acceptor peptide), and combinations of tags.

As used herein, the terms "labeling", and "to label" refer to the act of contacting a target substance (e.g., a cell, or a population of cells, or a sample) with a label effective that the label adheres to the target substance. Labeling a target is typically used to detect, or to identify, or quantify the numbers or, a target in a sample. A label may be highly specific (e.g., an antibody) or may be directed to a less specific target (e.g. a cell nucleus stain, such as hematoxylin, bisalkylaminoanthraquinone (DRAQ5), or other nuclear stain which labels DNA without regard to the nucleic acid sequence). A label may bind to its target by covalent, hydrogen bond, byrophobic, van der Waals, or other interaction or combination of interactions. A label may be detected by emission (e.g., a fluorescent, chemiluminescent, or radioactive label); by color change, absorption, reflection, or scattering of light, ultrasound, or other energy; or by any other means.

As used herein, the terms "detecting", "to detect" and the like refer to obtaining information indicative of the presence, or absence, or of the quantity of, a target substance such as an analyte in a sample. A target, such as an analyte, may be detected directly, or may be detected indirectly (e.g., may be detected by detection of a label bound to the analyte; or may be detected by the result of a chemical or other reaction indicative of the presence of the analyte; or by other indirect means).

As used herein, the terms "detector", "detection device", "detection apparatus" and the like refer to sensors, devices, or systems for obtaining information indicative of the presence, or absence, or of the quantity of, a target substance such as an analyte in a sample. In an assay, a detector is used to detect a signal indicative of the presence, or absence, or of the quantity of, a target substance such as an analyte in a sample. A detector typically includes a sensor capable of providing a signal when an event occurs; such an event may be, for example, the arrival or a photon, or other electromagnetic event, at a surface which reacts to that arrival or event. Thus, for example, a detector may be an optical detector; an acoustic detector; a chemical detector; a mechanical detector; a radiation detector; or other detector or combination of these.

An acoustic detector may be, for example, a microphone, or piezoelectric sensor, or ultrasound detector, or other acoustic detector or combinations of these.

A radiation detector may be, for example, a Geiger counter, a film radiation detector, an ionization meter, or other radiation detector, or combination of these.

A chemical detector may be, for example, a pH sensor, an ion-selective electrode, a electrochemical sensor (e.g., a voltammetric or amperometric sensor), an enzyme- or a catalyst-based sensor, or other sensor or combinations of these.

A mechanical sensor may be, for example, an accelerometer; a strain gauge; a lever; or other sensor or combinations of these.

Optical detectors include, without limitation, photomultiplier tubes (OMTs); photodiodes; charge-coupled devices (CCDs); super-cooled CCDs; cameras; microscopes; pin diodes; photon counting detectors; avalanche photo diodes; and arrays and combinations of these.

As used herein, the terms "electromagnetic energy" and "electromagnetic radiation" refer equally to electromagnetic emanations of any frequency, including, for example, visible light (typically termed "light"), microwaves, radiowaves, and other electromagnetic radiation.

As used herein, the terms "ultrasound" and "ultrasonic energy" and grammatical equivalents refer to high frequency acoustic vibrations, whether transmitted through the air, through a solid, through a gel, by direct contact, or otherwise. Ultrasonic energy is typically produced by a sonicator, and the ultrasonic energy transmitted via the tip of a sonicator. Acoustic energy may be used to agitate, stir, mix, or heat a preparation; to detect or image a target, such as a cell, tissue, or organ; to fragment or disrupt a preparation (e.g., a preparation including cells to be lysed); to move, localize, or otherwise position a material or cell, or to separate objects from each other (e.g., acoustic focusing); and in other ways.

As used herein, assays and assay steps are "compatible" when the assays or assay steps may be performed together using portions of a single biological sample; where performance together may include simultaneous, overlapping, and sequential performance of the assays or assay steps. Examples of compatible assays and assay steps include, without limitation, assays and assay steps which may be: performed using the same reagents; performed under the same conditions (e.g., temperature, pH, osmotic, and other conditions); performed with different conditions, where the different conditions do not interfere with the performance of the assays (e.g., one assay may not be temperature sensitive; performed with different reagents, where the different reagents do not interfere with the performance of the assays (e.g., one assay may use a chelator, a solvent, a surfactant, or other compound whose presence, while not required by a second assay, does not interfere with a second assay); and other assays and assay steps. Further examples of compatible assays and assay steps include, without limitation, assays and assay steps which can all be performed using an aliquot of the same biological sample, and may be performed simultaneously, e.g., may be performed in a single device or system at the same time. Further examples of compatible assays and assay steps include, without limitation, assays and assay steps which can all be performed using an aliquot of the same biological sample, and may be performed at times that overlap, at least partially; e.g., the assays may be performed in a single device or system starting at the same time, or starting at different times, but for at least some time some portion of the assays are performed concurrently. Further examples of compatible assays and assay steps include, without limitation, assays and assay steps which can all be performed using an aliquot of the same biological sample, and may be performed sequentially, e.g., may be performed in a single device or system at different times.

As used herein with respect to a comparison of assays, the phrase "as good as" refers to aspects or results of assays that are substantially equal to each other, e.g., the numerical values are substantially the same; or the coefficients of variation are substantially the same; or the precision is substantially the same; or the times taken to perform each of the assays are substantially the same; or the amount or cost of reagents required to perform the assays are substantially the same; or other aspects or results of the assays are substantially the same for both assays. It will be understood that, for numerical comparisons, "as good as" may be within about 75%, or within about 50%, or within about 25%, or within about 10%, of each other. It will be understood that, for non-numerical comparisons, "as good as" refers to results which are judged by a knowledgeable observer to be similar, or not substantially different, from each other.

As used herein with respect to a comparison of assays, the phrase "better than" refers to aspects or results of an assays that are provide more accurate, or more precise, or more reliable, results; or are obtained more rapidly, or more simply, or more cheaply; or that are obtained in a manner more compatible with other assays commonly performed on similar samples (e.g., results which aid or enable the performance of two or more assays on the same sample); or that otherwise offer advantages as compared with the other assay. For example, where the assay produces numerical results, the results are numerically superior; or the coefficients of variation are smaller; or the precision is greater. Non-numerical criteria may indicate that one assay is, or assay results are, better than another assay or other assay results; for example, an assay is better if times required to perform the assay is reduced; or the complexity of the assay is reduced; or if a preferred detection method or device may be used with the revised assay; or the amount or cost of reagents required to perform the assay is decreased; or other aspects or results of the assays are substantially the same for both assays. It will be understood that, for numerical comparisons, "better than" may be greater than about 10%, or greater than about 25%, or greater than about 50%, or greater than about 75%, or more. It will be understood that, for non-numerical comparisons, "better than" refers to results which are judged by a knowledgeable observer to be better based on their experience and familiarity with such results.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Analyte Detection

A detection unit may include one or more optical or visual sensor or sonic or magnetic or radioactivity sensor or some combination of these. For example, a detection unit may include microscopy, visual inspection, via photographic film, or may include the use of electronic detectors such as digital cameras, charge coupled devices (CCDs), super-cooled CCD arrays, photodetector or other detection device. An optical detector may further include non-limiting examples include a photodiode, photomultiplier tube (PMT), photon counting detector, or avalanche photo diode, avalanche photodiode arrays. In some embodiments a pin diode may be used. In some embodiments a pin diode can be coupled to an amplifier to create a detection device with a sensitivity comparable to a PMT. Some assays may generate luminescence as described herein. In some embodiments fluorescence or chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors. In some embodiments, fiber optic cables may be directly incorporated into assay or reagent units. For example, samples or tips as described elsewhere herein may incorporate fiber optic cables. In some embodiments, electronic sensors for detection or analysis (such as image processing) may be built into the pipette or other component of the fluid handling system. In some embodiments, a detection unit may be a PMT. In some embodiments, a detection unit may be a photodiode. In some embodiments, a detection unit may be a spectrophotometer. In some embodiments, a detection unit may be a nucleic acid assay station containing or operatively coupled to a light source and an optical sensor. In some embodiments, a detection unit may be a camera. In some embodiments, a detection unit may be an imaging device. In some embodiments, a detection unit may be a cytometry station containing a microscopy stage and an imaging device. In some embodiments, a detection unit containing a CCD or CMOS sensor may be configured to obtain a digital image, such as of a sample, assay unit, cuvette, assay, the device, or the device surroundings. The digital image may be two-dimensional or three-dimensional. The digital image may be a single image or a collection of images, including video. In some instances, digital imaging may be used by the device or system for control or monitoring of the device, it surroundings, or processes within the device.

One or more detection units may be configured to detect a detectable signal, which can be a light signal, including but not limited to photoluminescence, electroluminescence, sonoluminescence, chemiluminescence, fluorescence, phosphorescence, polarization, absorbance, turbidity or scattering. In some embodiments, one or more label may be employed during a chemical reaction. The label may permit the generation of a detectable signal. Methods of detecting labels are well known to those of skill in the art. Thus, for example, where the label is a radioactive label, means for detection may include a scintillation counter or photographic film as in autoradiography. Where the label is a fluorescent label, it may be detected by exciting the fluorochrome with the appropriate wavelength of light and detecting the resulting fluorescence by, for example, microscopy, visual inspection, via photographic film, by the use of electronic detectors such as digital cameras, charge coupled devices (CCDs) or photomultipliers and phototubes, or other detection device. In some embodiments, imaging devices may be used, such as cameras. In some instances, cameras may use CCDs, CMOS, may be lensless cameras (e.g., Frankencamera), microlens-array cameras, open-source cameras, or may use or any other visual detection technology known or later developed in the art. Cameras may acquire non-conventional images, e.g. holographic images, tomographic or interferometric, Fourier-transformed spectra, which may then be interpreted with or without the aid of computational methods. Cameras may include one or more feature that may focus the camera during use, or may capture images that can be later focused. In some embodiments, imaging devices may employ 2-d imaging, 3-d imaging, and/or 4-d imaging (incorporating changes over time). Imaging devices may capture static images. The optical schemes used to achieve 3-D and 4-D imaging may be one or more of the several known to those skilled in the art, e.g. structured illumination microscopy (SLM), digital holographic microscopy (DHM), confocal microscopy, light field microscopy etc. The static images may be captured at one or more point in time. The imaging devices may also capture video and/or dynamic images. The video images may be captured continuously over one or more periods of time. An imaging device may collect signal from an optical system which scans the sample in arbitrary scan patterns (e.g. raster scan). In some embodiments, the imaging device may use one or more component of the device in capturing the image. For example, the imaging device may use a tip and/or vessel to assist with capturing the image. The tip and/or vessel may function as an optic to assist in capturing an image.

Detection units may also be capable of capturing audio signals. The audio signals may be captured in conjunction with one or more image. Audio signals may be captured and/or associated with one or more static image or video images. Alternatively, the audio signals may be captured separate from the image.

In one example, a PMT may be used as a detector. In some instances, count rates as low as 100 per second and count rates as high as 10,000,000 may be measurable. The linear response range of PMTs (for example, the range where count rate is directly proportional to number of photons per unit time) can be about 1000-3,000,000 counts per second. In an example, an assay has a detectable signal on the low end of about 200-1000 counts per second and on the high end of about 10,000-2,000,000 counts per second. In some instances for protein biomarkers, the count rate is directly proportional to alkaline phosphatase bound to the capture surface and also directly proportional to the analyte concentration.

In another example, a detector may include a camera that may be imaging in real-time. Alternatively, the camera may take snapshots at selected time intervals or when triggered by an event. Similarly, the camera may take video at selected time intervals or when triggered by an event. In some embodiments, the camera may image a plurality of samples simultaneously. Alternatively, the camera may image a selected view, and then move on to a next location for a different selected view.

A detection unit may have an output that is digital and generally a one-to-one or one-to-many transformation of the detected signal, e.g., the image intensity value is an integer proportional to a positive power of the number of photons reaching the camera sensor over the time of exposure. Alternatively, the detection unit may output an analog signal. The detectable range for exemplary detectors can be suitable to the detector being used.

The detection unit may be capable of capturing and/or imaging a signal from anywhere along the electromagnetic spectrum. For example, a detection unit may be capable of capturing and/or imaging visible signals, infra-red signals, near infra-red signals, far infra-red signals, ultraviolet signals, gamma rays, microwaves, and/or other signals. The detection unit may be capable of capturing acoustic waves over a large range of frequencies, e.g. audio, ultrasound. The detection unit may be capable of measuring magnetic fields with a wide range of magnitude.

An optical detector can also comprise a light source, such as an electric bulb, incandescent bulb, electroluminescent lamp, laser, laser diode, light emitting diode (LED), gas discharge lamp, high-intensity discharge lamp, natural sunlight, chemiluminescent light sources. Other examples of light sources as provided elsewhere herein. The light source can illuminate a component in order to assist with detecting the results. For example, the light source can illuminate an assay in order to detect the results. For example, the assay can be a fluorescence assay or an absorbance assay, as are commonly used with nucleic acid assays. The detector can also comprise optics to deliver the light source to the assay, such as a lens, mirror, scanning or galvano-mirror, prisms, fiber optics, or liquid light guides. The detector can also comprise optics to deliver light from an assay to a detection unit. In some embodiments, a light source can be coupled to an optical detector/sensor which is configured primarily for the detection of luminescent assays, in order to expand the range of types of assays that may be detected by the optical sensor (e.g. to include absorbance, fluorescence, turbidity, and colorimetry assays, etc.).

An optical detection unit may be used to detect one or more optical signal. For example, the detection unit may be used to detect a reaction providing luminescence. The detection unit may be used to detect a reaction providing fluorescence, chemiluminscence, photoluminescence, electroluminescence, color change, sonoluminescence, absorbance, turbidity, or polarization. The detection unit may be able to detect optical signals relating to color intensity and phase or spatial or temporal gradients thereof. For example, the detection unit may be configured to detect selected wavelengths or ranges of wavelengths. The optical detection unit may be configured to move over the sample and a mirror could be used to scan the sample simultaneously.

In some embodiments, an assay provided herein generating a particular type of result (e.g. luminescence, turbidity, color change/colorimetry, etc.) may be monitored by different types or configurations of detection units provided herein. For example, in some situations, an assay resulting in a turbid reaction product may be monitored in: i) a dedicated spectrophotometer, ii) a nucleic acid assay station containing or operatively coupled to a light source and a optical sensor, or iii) a detection unit containing a CCD sensor (e.g. a stand-alone imaging device containing a CCD sensor, or a cytometry station containing an imaging device containing a CCD sensor). In both detection unit configurations i) and ii), the sample may be positioned in the detection unit between the respective light source and the respective optical sensor, such that ii) (incident radiation) and $I_1$ (transmitted radiation) values may be measured at one or more selected wavelengths, and absorbance calculated. In detection unit configuration iii), an image of the sample may be obtained by the CCD sensor, and further processed by image analysis. In some embodiments, a sample may be monitored in more than one of the above detection units. In another example, in some situations, an assay resulting in a chemiluminescent signal may be monitored by i) a photodiode or other luminescence sensor, ii) a nucleic acid assay station containing or operatively coupled to a light source and an optical sensor, or iii) a detection unit containing a CCD sensor. In configuration i) the photodiode detects light from the chemiluminescent reaction. In some situations, the photodiode may be configured to sense very low levels of light, and thus may be used with assays which result in only a low level of chemiluminescence. In configuration ii) the assay (including non-nucleic acid amplification assays) may be placed in the nucleic acid amplification module, and the optical sensor within the station may be used to detect light from the chemiluminescent assay (without using the light source in the station). In some situations, the optical sensor in this configuration may not be as sensitive to light as a stand-alone photodiode or PMT, and therefore, use of the nucleic acid assay staiton as detector for chemiluminscence assays may be with assays which produce relatively moderate to high levels of chemiluminescent light. In configuration iii), an image of the chemiluminescent sample may be obtained by the CCD sensor, and further processed by image analysis (including light counts) to determine the level of chemiluminescence in the sample.

Assays

An assay may comprise a physical assay, a chemical assay, an electrochemical assay, an optical assay (using any suitable wavelength, or combination of wavelengths, of electromagnetic energy), or a combination of any of these. Physical assays include but are not limited to, assays which detect or measure a physical property of a sample (e.g., weight, volume, density, viscosity, temperature, or other characteristic or property). Chemical assays include but are not limited to, assays which detect or measure a chemical property of a sample (e.g., which detect the presence, absence, or concentration, of a chemical compound (e.g., an analyte)), or a material which comprises a compound or analyte; or which detect or measure a chemical property of a sample (e.g., pH, partial pressure, concentration of a chemical, or other chemical property). Electrochemical assays include but are not limited to, assays which detect the presence, absence, or concentration, of a chemical compound using electrochemical means, such as, e.g., ion-selective electrode techniques, amperommetry, voltammetry, and other such means. Optical assays include, but are not limited to, for example, fluorescence, chemiluminescence, autofluorescence, quenching, Förster resonance energy transfer (FRET) assays, and other fluorescence and luminscence assays; absorbance assays; transmittance assays; turbidometric assays assays; colorimetric assays; spectroscopic assays; polarimetric assays; circular dichroic assays; linear dichroic assays; optical rotation assays; and other optical assays which utilize any suitable wavelength or wavelengths of electromagnetic energy.

In embodiments, an assay may comprise a pre-treatment and a treatment. Thus, in embodiments, an assay may comprise (a) at least one sample preparation procedure (e.g., a pretreatment) selected from the group consisting of aliquotting, filtering, centrifuging, precipitating, coagulating, separating, sample processing, and chemical processing; and (b) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidometric assay, agglutination assay, radioisotope assay, viscometric assay, coagulation assay, clotting time assay, protein synthesis assay, histological assay, culture assay, and osmolarity assay; and wherein the multiple types of assays are performed with the aid of isolated (including but not limited to fluidically) assay units contained within the system. In some embodiments, separation includes magnetic separation.

In embodiments, assays may comprise at least one sample preparation procedure selected from the group consisting of sample processing, centrifugation, and magnetic separation. In embodiments, assays may comprise at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof. Where a plurality of assays are performed together, or in conjunction with each other, multiple types of assays may be performed with the aid of isolated (including but not limited to fluidically) assay units contained within a device or system. In embodiments, assay device and systems may be configured to be in electrical, electro-magnetical or optoelectronic communication with a controller, said controller being configured to provide one or more instructions to said module or individual modules of said plurality of modules to facilitate performance of the at least one sample preparation procedure or the at least one type of assay.

In embodiments, an assay may comprise a treatment and a post-treatment. For example in embodiments, an assay may comprise i) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidometric assay, agglutination assay, radioisotope assay, viscometric assay, coagulation assay, clotting time assay, protein synthesis assay, histological assay, culture assay, and osmolarity assay; and ii) a post-treatment step. In embodiments, such a post-treatment step may be one or more of precipitating a reaction product; removing non-target material from a sample; fixing a sample; preparing the sample for a subsequent assay; and disposing of all or a portion of a sample or associated reagents following measurement or use of the sample. In embodiments, multiple types of assays may be performed with the aid of isolated assay units contained within a device or system.

Thus, in embodiments, processing of a biological sample may include pre-treatment (e.g., preparation of a sample for a subsequent treatment or measurement), processing (e.g., alteration of a sample so that it differs from its original, or previous, state), and post-treatment (e.g., fixing a sample, or disposing of all or a portion of a sample or associated reagents following its measurement or use). A biological sample may be divided into portions, such as aliquots of a blood or urine sample, or such as slicing, mincing, or dividing a tissue sample into two or more pieces.

Processing of a biological sample, such as blood sample, may include mixing, stirring, sonication, homogenization, or other treatment of a sample or of a portion of the sample. Processing of a biological sample, such as blood sample, may include centrifugation of a sample or a portion thereof.

Processing of a biological sample, such as a blood sample, may include providing time for components of the sample to separate or settle, and may include filtration (e.g., passing the sample or a portion thereof through a filter or membrane). Processing of a biological sample, such as a blood sample, may include allowing or causing a blood sample to coagulate. Processing of a biological sample, such as blood sample, may include concentration of the sample, or of a portion of the sample (e.g., by sedimentation or centrifugation of a blood sample, or of a solution containing a homogenate of tissue from a tissue sample, or with magnetic or other beads) to provide a pellet and a supernatant.

Processing of a biological sample, such as blood sample, may include dilution of a portion of the sample. Dilution may be of an entire sample, or of a portion of a sample, including dilution of a pellet or of a supernatant from sample. A biological sample may be diluted with water, or with a saline solution, such as a buffered saline solution. A biological sample may be diluted with a solution which may or may not include a fixative (e.g., formaldehyde, paraformaldehyde, or other agent which cross-links proteins). A biological sample may be diluted with a solution such that an osmotic gradient is produced between the surrounding solution and the interior, or an interior compartment, of such cells, effective that the cell volume is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution). For example, treating a blood sample so as to cause cell swelling in the presence of a cross-linking agent (e.g. formaldehyde, paraformaldehyde, or other fixative) may provide a blood sample in which red blood cells are osmotically burst (and may be removed if desired), yet the white blood cells, which swell and cross-link at different rates than the red blood cells, remain and may be analyzed with less interference than otherwise would be caused by the more numerous red blood cells.

A biological sample may be dyed, or markers or reagents may be added to the sample, or the sample may be otherwise prepared for detection, visualization, or quantification of the sample, a portion of a sample, a component part of a sample, or a portion of a cell or structure within a sample. For example, a biological sample may be contacted with a solution containing a dye. A dye may stain or otherwise make visible a cell, a portion of a cell, a component inside a cell, or a material or molecule associated with a cell in a sample. A dye may bind to or be altered by an element, compound, or other component of a sample; for example a dye may change color, or otherwise alter one of more of its properties, including its optical properties, in response to a change or differential in the pH of a solution in which it is present; a dye may change color, or otherwise alter one of more of its properties, including its optical properties, in response to a change or differential in the concentration of an element or compound (e.g., sodium, calcium, CO2, glucose, or other ion, element, or compound) present in a solution in which the dye is present. For example, a biological sample may be contacted with a solution containing an antibody or an antibody fragment. For example, a biological sample may be contacted with a solution that includes particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

In some embodiments, binding of one or more analyte receptors to one or more target analytes is detected using one or more detectable labels or tags. In general a label is a molecule that can be directly (i.e., a primary label) or indirectly (i.e., a secondary label) detected; for example a label can be visualized and/or measured or otherwise identified so that its presence or absence can be known. A label can be directly or indirectly conjugated to one or more of an analyte receptor, an analyte, or a tag (e.g. a probe) that interacts with either or both of the analyte or analyte receptor. In general, a label provides a detectable signal. Non-limiting examples of labels useful in the invention include fluorescent dyes (e.g., fluorescein isothiocyanate, Texas red, rhodamine, and the like), enzymes (e.g., LacZ, CAT, horseradish peroxidase, alkaline phosphatase, I 2-galactosidase, β-galactosidase, and glucose oxidase, acetylcholinesterase and others, commonly used as detectable enzymes), nanoparticles (such as, e.g., gold nanoparticles), quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; magnetic particles; electrical labels; thermal labels; luminescent molecules; phosphorescent molecules; chemiluminescent molecules; fluorophores such as umbelliferone, fluorescein, rhodamine, tetramethyl rhodamine, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin, fluorescent lanthanide complexes such as those including Europium and Terbium, molecular beacons and fluorescent derivatives thereof, a luminescent material such as luminol; light scattering or plasmon resonant materials such as gold or silver particles or quantum dots; radiolabels or heavy isotopes including $^{14}C$, $^{123}I$, $^{124}I$, $^{131}I$, $^{125}I$, Tc99m, $^{32}P$, $^{35}S$ or $^{3}H$; or spherical shells; and probes labeled with any other signal generating label known to those of skill in the art, as described, for example, in Principles of Fluorescence Spectroscopy, Joseph R. Lakowicz (Editor), Plenum Pub Corp, 2nd edition (July 1999) and the 6 th Edition of the Molecular Probes Handbook by Richard P. Hoagland. Two or more different labels may be used together to detect two or more analytes in a single assay. In some embodiments, about or more than about 1, 2, 3, 4, 5, 6, 7, 8, 9, 10, 11, 12, 13, 14, 15, 16, 17, 18, 19, 20, or more different labels are used in a single assay.

In some embodiments, the label is an enzyme, the activity of which generates a product having a detectable signal. Substrates used for sensitive detection can be colorimetric, radioactive, fluorescent or chemiluminescent. Conventional colorimetric substrates produce a new color (or change in spectral absorption) upon enzyme action on a chromogenic substrate. In general, colorimetric substrates produce a change in spectral absorption. In some embodiments, the enzyme is horseradish peroxidase, substrates of which include but are not limited to 3,3'-diaminobenzidine (DAB), 3-Amino-9-ethylcarbazole (AEC), and Bajoran Purple. In some embodiments, the enzyme is alkaline phosphatase, substrates of which include but are not limited to Fast Red and Ferangi Blue. A variety of other enzymatic labels and associated chromagens are known in the art, and are available from commercial suppliers such as Thermo Fisher Scientific. A non-limiting example of an enzymatic assay is an enzyme-linked immunosorbant assay (ELISA). Methods for performing ELISA are known in the art, and may be similarly applied in the methods disclosed herein. An analyte may or may not be bound by a first analyte receptor that is not labeled before exposure to a second analyte receptor that is labeled (e.g. sandwich ELISA) and specifically binds to either the analyte or the first analyte receptor. In a typical ELISA assay, the analyte receptor linked to an enzyme is an antibody. Similar assays may be performed where the antibody is replace with another analyte receptor.

Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAE-DANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP), enhanced GFP (EGFP), blue fluorescent protein (BFP), enhanced yellow fluorescent protein (EYFP), luciferase, β-galactosidase, and *Renilla*. Further examples of fluorescent labels are described in WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558, which are incorporated herein by reference.

In some embodiments, labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC are known in the art. Quantitation of fluorescent probe conjugation may be assessed to determine degree of labeling and protocols including dye spectral properties are also well known in the art. In some embodiments the fluorescent label is conjugated to an aminodextran linker which is conjugated to a binding element or antibody. Additional labels are listed in and are available through the on-line and hard copy catalogues of BD Biosciences, Beckman Coulter, AnaSpec, Invitrogen, Cell Signaling Technology, Millipore, eBioscience, Caltag, Santa Cruz Biotech, Abcam and Sigma, the contents of which are incorporated herein by reference.

Labels may be associated with the analyte receptor, the analyte, or both, which association may be covalent or non-covalent. Detection may result from either an increase or decrease in a detectable signal from a label. In some embodiments, the degree of increase or decrease correlates with the amount of an analyte. In some embodiments, a sample containing analytes to be analyzed is treated with a labeling compound to conjugate the analytes with a label, such as a fluorescent tag. Binding can then be measured by detection of the label, such as by measuring fluorescence, to detect presence and optionally quantity of one or more analytes, such as in combination with analyte receptors coupled to an array or analyte receptors coupled to coded beads. In some embodiments, the sample is treated with a labeling compound to conjugate the analytes with a linker. Upon binding the linker is functionalized with a label, such as a fluorescent tag, and the positive event is measured by detection of the tag, such as an increase in fluorescence. In some embodiments, the analyte binding domain of an analyte receptor is bound by a probe comprising a label, such as a fluorescent label; upon binding to the analyte, the probe is released, which results in a measurable decrease in a detectable signal from the label (e.g. a decrease in fluorescence). In some embodiments, an analyte receptor is fluorescently labeled and is partially bound by a probe labeled with a quencher that is in proximity to the fluorescent label; upon binding to the analyte, the complementary probe is released resulting in a measurable increase in fluorescence of the label conjugated to the analyte receptor. In some embodiments, the analyte receptor is bound by a probe, which hybridization occludes a domain containing a secondary structure; upon binding to the analyte, the probe is released, and the secondary structure is made available to a label, such as an intercalating dye, used to produce a measurable signal. Labels useful in the detection of binding between an analyte receptor and an analyte in a binding pair can include, for example, fluorescein, tetramethylrhodamine, Texas Red, or any other fluorescent molecules known in the art. The level of label detected will then vary with the amount of target analyte in the mixture being assayed.

In some embodiments, a displaced probe is conjugated to one member of an affinity pair, such as biotin; or digoxigenin. A detectable molecule is then conjugated to the other member of the affinity pair, for example avidin, or streptavidin; or an antibody to digoxigenin. After a test mixture is applied to an assay unit comprising analyte receptors, a detectable molecule is added. The amount of detectable molecule will vary inversely with the amount of target molecule present in the test mixture. In another embodiment, the displaced probe will be biotin labeled, and can be detected by addition of fluorescently labeled avidin; the avidin itself will then be linked to another fluorescently labeled, biotin-conjugated compound. The biotin group on the displaced oligonucleotide can also be used to bind an avidin-linked reporter enzyme; the enzyme will then catalyze a reaction leading to the deposition of a detectable compound. Alternatively, the reporter enzyme will catalyze the production of an insoluble product that will locally quench the fluorescence of an intrinsically-fluorescent solid surface. In another embodiment of a displacement assay, a displaced probe will be labeled with an immunologically-detectable probe, such as digoxigenin. The displaced probe will then be bound by a first set of antibodies that specifically recognize the probe. These first antibodies will then be recognized and bound by a second set of antibodies that are fluorescently labeled or conjugated to a reporter enzyme.

In some embodiments, an analyte receptor, such as an antibody, induces an agglutination reaction in the presence of one or more target analytes (e.g. antigens). Typical agglutination reactions involving the use of antibodies include (i) mixing polyclonal antibodies with a sample containing an antigen corresponding to the antibodies, and observing the formation of immunoagglutinates; (ii) mixing a monoclonal antibody with a sample containing an antigen carrying at least two antigenic functions (bivalent or multivalent antigen) and observing the formation of immunoagglutinates; (iii) mixing at least two different monoclonal antibodies with a sample containing a monovalent antigen and observing immunoagglutination; (iv) any of the reactions mentioned above, but applying the antibodies, or other suitable analyte receptor as described herein, coupled to particles, such as latex particles, colloids, etc.; and (v) any of the reactions mentioned above, but applied to antigens present on cell surfaces in which case the number of antigens per physical unit is normally a hundred or more, and in which case such cells may be agglutinated by monoclonal antibodies, or other suitable analyte receptor as described herein, even if each antigen molecule is monovalent. Agglutination reactions can be observed on the surface of a solid substrate such as a glass or plastic plate, or in a solution, such as in a microtitre plate, cuvette, tip, capillary, or other suitable container. The solid surface or container is preferably colored to contrast with the color of the agglutinate. In some embodiments, the solid surface or container is optically clear, such that agglutination may be measured by changes in color, contrast, absorbance, or detection of any other suitable label as described herein. In some embodiments, agglutination is measured is a fluid flow, where the presence of an agglutinate is determined by disruptions in the flow of the fluid. In some embodiments the agglutination reaction is a hemagglutination reaction. In some embodiments, the agglutination reaction is an agglutination inhibition reaction, wherein the presence of an analyte (e.g. a small molecule, drug, or drug metabolite) inhibits or slows the rate of an agglutination reaction, such as by competing for binding with an analyte receptor (e.g. an antibody) in the presence of an agglutinatable target (e.g. beads coated with analyte).

Receptor binding assays as described herein may be combined with one or more other assays, such as on different samples analyzed within a single device or system, or on the same sample. Different assays may be performed simultaneously or sequentially on one or more samples.

In some embodiments, multiple analytes can assayed simultaneously. Multiple analytes may be analyzed in separate vessels or in the same vessel. The same analyte might be assayed using different detectors. This may allow the system to maintain high precision on different concentration ranges of the analyte.

General Chemistry Assays

In some embodiments, automatic assay devices and systems may be configured to perform one or more general chemistry assays. For example, general chemistry assays often used to analyze blood samples may include, for example: assays of a Basic Metabolic Panel [glucose, calcium, sodium (Na), potassium (K), chloride (Cl), CO2 (carbon dioxide, bicarbonate), creatinine, blood urea nitrogen (BUM], assays of an Electrolyte Panel [sodium (Na), potassium (K), chloride (Cl), CO2 (carbon dioxide, bicarbonate)], assays of a Chem 14 Panel/Comprehensive Metabolic Panel [glucose, calcium, albumin, total protein, sodium (Na), potassium (K), chloride (Cl), CO2 (carbon dioxide, bicarbonate), creatinine, blood urea nitrogen (BUN), alkaline phosphatase (ALP), alanine aminotransferase (ALT/GPT), aspartate aminotransferase (AST/GOT), total bilirubin] assays of a Lipid Profile/Lipid Panel [LDL cholesterol, HDL cholesterol, total cholesterol, and triglycerides], assays of a Liver Panel/Liver Function [alkaline phosphatase (ALP), alanine aminotransferase (ALT/GPT), aspartate aminotransferase (AST/GOT), total bilirubin, albumin, total protein, gamma-glutamyl transferase (GGT), lactate dehydrogenase (LDH), prothrombin time (PT)], alkaline phosphatase (APase), hemoglobin, VLDL cholesterol, ethanol, lipase, pH, zinc protoporphyrin, direct bilirubin, blood typing (ABO, RHD), lead, phosphate, hemagglutination inhibition, magnesium, iron, iron uptake, fecal occult blood, and others, individually or in any combination.

In general chemistry assays provided herein, in some examples, the level of an analyte in a sample is determined through one or more assay steps involving a reaction of the analyte of interest with one or more reagents, leading to a detectable change in the reaction (e.g. change in the turbidity of the reaction, generation of luminescence in the reaction, change in the color of the reaction, etc.). In some examples, a property of a sample is determined through one or more assay steps involving a reaction of the sample of interest with one or more reagents, leading to a detectable change in the reaction (e.g. change in the turbidity of the reaction, generation of luminescence in the reaction, change in the color of the reaction, etc.). Typically, as used herein, "general chemistry" assays do not involve amplification of nucleic acids, imaging of cells on a microscopy stage, or the determination of the level of an analyte in solution based on the use of a labeled antibody to determine the level of an analyte in a solution. In some embodiments, general chemistry assays are performed with all reagents in a single vessel—i.e. to perform the reaction, all necessary reagents are added to a reaction vessel, and during the course of the assay, materials are not removed from the reaction or reaction vessel (e.g. there is no washing step; it is a "mix and read" reaction). General chemistry assays may also be, for example, colorimetric assays, enzymatic assays, spectroscopic assays, viscometric assays, specific-binding assays (e.g., using metal ions, but typically not using antibodies), turbidometric assays, agglutination assays, coagulation assays, and/or other types of assays. Some general chemistry assays may utilize antibodies in ways other than antibodies are used in immunoassays; for example, agglutination assays and hemagglutination assays may be considered general chemistry assays, although they may use antibodies to condense the target analytes. Many general chemistry assays may be analyzed by measuring the absorbance of light at one or more selected wavelengths by the assay reaction (e.g. with a spectrophotometer). In some embodiments, general chemistry assays may be analyzed by measuring the turbidity of a reaction (e.g. with a spectrophotometer). In some embodiments, general chemistry assays may be analyzed by measuring the chemiluminescence generated in the reaction (e.g. with a PMT, photodiode, or other optical sensor). Some general chemistry assays may utilize image analysis (e.g., agglutination assays and sedimentation assays) and are considered general chemistry assays. In some embodiments, general chemistry assays may be analyzed by measuring fluorescence of a reaction (e.g. with a detection unit containing or connected to i) a light source of a particular wavelength(s) ("excitation wavelength(s)"); and ii) a sensor configured to detect light emitted at a particular wavelength(s) ("emission wavelength(s)"). In some embodiments, general chemistry assays may be analyzed by measuring agglutination in a reaction (e.g. by measuring the turbidity of the reaction with a spectrophotometer or by obtaining an image of the reaction with an optical sensor). In some embodiments, general chemistry assays may be analyzed by imaging the reaction at one or more time points (e.g. with a CCD or CMOS optical sensor), followed by image analysis. Optionally analysis may involve prothrombin time, activated partial thromboplastin time (APTT), either of which may be measured through a method such as but not limited to turbidimetry. In some embodiments, general chemistry assays may be analyzed by measuring the viscosity of the reaction (e.g. with a spectrophotometer, where an increase in viscosity of the reaction changes the optical properties of the reaction). In some embodiments, general chemistry assays may be analyzed by by measuring complex formation between two non-antibody reagents (e.g. a metal ion to a chromophore; such a reaction may be measured with a spectrophotometer or through colorimetry using another device). In some embodiments, general chemistry assays may be analyzed by non-ELISA or cytometry-based methods for assaying cellular antigens (e.g. hemagglutination assay for blood type, which may be measured, for example, by turbidity of the reaction). In some embodiments, general chemistry assays may be analyzed with the aid of electrochemical sensors (e.g. for carbon dioxide or oxygen). In some embodiments, general chemistry assays may be performed by calculations, based on experimental values determined for one or more other analytes in the same or a related assay. Additional methods may also be used to analyze general chemistry assays.

In some embodiments, a spectrophotometer may be used to measure an analyte or multiple analytes in a general chemistry assay. In some embodiments, general chemistry assays may be measured at the end of the assay (an "endpoint" assay) or at two or more times during the course of the assay (a "time-course" or "kinetic" assay). Assays which may utilize a spectrophotometer include chromogenic assays, color change assays, near ultraviolet (near UV) assays, turbidmetric assays, and light-scattering assays. Examples of such assays which may utilize a spectrophotometer include the following assays.

A glucose assay may be performed, for example, by incubating a biological sample (e.g. plasma, urine, etc.) with glucose oxidase, to generate gluconic acid and hydrogen peroxide. In an example, the hydrogen peroxide may be incubated with a peroxidase and a chromogen that can change color when oxidized—e.g. o-dianisidine. A colored product may be further stabilized by reaction with sulfuric acid. The colored product may be measured in a spectrophotometer by absorbance at 405 nm. In another example, the hydrogen peroxide may be incubated with a peroxidase, 4-aminoantipyrine, and a phenolic compound (e.g. N, N diethylaniline), to form a colored product. The product may be measured, for example, in a spectrophotometer at 510 nm.

An alanine aminotransferase assay may be performed, for example, by incubating a biological sample (e.g. plasma, urine, etc.) with alpha-ketoglutarate and alanine, to generate glutamate and pyruvate. Incubation of these products with an oxidizable chromogen [e.g. 10-acetyl-3,7-dihydroxyphenoxazine (ADHP)] may generate a colored product. Oxidized 10-acetyl-3,7-dihydroxyphenoxazine may be detected, for example, colorimetrically in a spectrophotometer by absorbance at 570 nm, or fluorescently, at EX/EM=535/587 nm. In another example, the glutamate and pyruvate products may be incubated with lactate dehydrogenase and NADH, where pyruvate reacts with NADH in a lactate dehydrogenase-catalyzed reaction to form NAD+ and lactate. This reaction may be monitored by absorbance at 340 nm, at which NADH absorbs (i.e. the more NADH is consumed, the lower the absorbance at 340 nm).

A potassium assay may be performed, for example, by incubating a biological sample (e.g. plasma, urine, etc.) with tetraphenylborate. Potassium in the plasma may form an insoluble salt with the tetraphenylborate, which may precipitate out of solution and/or increase the turbidity of the sample. The assay may be measured in a spectrophotometer, for example, by measuring absorbance of the sample at 578 nm.

An alkaline phosphatase assay may be performed, for example, by incubating a biological sample (e.g. plasma, urine, etc.) with the chromogen p-nitrophenyl phosphate (pNPP). pNPP may be dephosphorylated by alkaline phosphatase to form p-nitrophenol and phosphate; it forms a yellow color upon dephosphorylation. The assay may be measured, for example, in a spectrophotometer by measuring, colorimetrically, the absorbance of the sample at 405 nm. In another example, an alkaline phosphatase assay may be performed, for example, by incubating plasma with a chemiluminescent substrate that releases light upon alkaline phosphatase-mediated cleavage (e.g. 3-(2'-spiroadamantyl)-4-methoxy-4-(3"-phosphoryloxy)-phenyl-1,2-dioxetane (AMPPD)). The assay may be measured, for example, by obtaining a reading of the assay at a light sensor (e.g. a PMT or photodiode).

A sodium assay may be performed, for example, by incubating a biological sample (e.g. plasma, urine, etc.) with beta-galactosidase and ortho-nitrophenyl-beta-galactoside (ONPG). Beta-galactosidase may have sodium-dependent activity, and hydrolyze ONPG to galactose and ortho-nitrophenol. Ortho-nitrophenol generation may be measured in a spectrophotometer by absorbance at 420 nm.

A calcium assay may be performed, for example, by incubating a biological sample (e.g. plasma, urine, etc.) with o-cresolphthalein and 2-amino-2-methyl-1-propanol. Calcium in the plasma may form a complex with the o-cresolphthalein, the complex having a purple color. The complex may be measured in a spectrophotometer by absorbance at 575 nm.

A hemoglobin assay may be performed, for example, by incubating whole blood with one or more detergents, ferricyanide, and cyanide. Hemoglobin may form a complex with cyanide, which may be measured in a spectrophotometer by absorbance at 540 nm.

An HDL-cholesterol assay may be performed, for example, by incubating a biological sample (e.g. plasma, etc.) with reagents that protect non-HDL cholesterol (e.g. LDL, VLDL, and chylomicrons) but leave HDL-cholesterol exposed to enzymes. These reagents may include, for example, polyvinylsulfonic acid (PVS), polyethylene glycol methylether (PEGME) or dextran sulfate. The reaction mixture is then incubated with cholesterol esterase (to convert cholesteryl ester to cholesterol) and cholesterol oxidase (to convert cholesterol to cholest-4-ene-3-one, and simultaneously producing hydrogen peroxide). The reaction mixture is incubated with an oxidizable chromogen (e.g. N-(2-hydroxy-3-sulfopropyl)-3,5-dimethyoxyaniline (ALPS) and aminoantipyrene (AAP)) or fluorescent dye, which may be oxidized by hydrogen peroxide, catalyzed by a peroxidase (e.g. horseradish peroxidase).

A VLDL-cholesterol assay may be performed, for example, by calculating the level of VLDL in a sample based on the enzyme-based determination of the level of other cholesterol molecules in the sample (e.g. total cholesterol and HDL-cholesterol). In some instances, VLDL is estimated to be one-fifth of the total triglycerides in the sample. In another example, VLDL-cholesterol may be determined with LDL-cholesterol, by physically or chemically separating LDL and VLDL-cholesterol from HDL-cholesterol. The isolated LDL/VLDL may then be incubated with cholesterol esterase (to convert cholesteryl ester to cholesterol) and cholesterol oxidase (to convert cholesterol to cholest-4-ene-3-one, and simultaneously producing hydrogen peroxide). The reaction mixture is incubated with an oxidizable chromogen (e.g. ALPS/AAP) or fluorescent dye, which may be oxidized by hydrogen peroxide, catalyzed by a peroxidase (e.g. horseradish peroxidase).

A pH assay may be performed, for example, by incubating a biological sample (e.g. plasma, urine, etc.) with a pH indicator molecule. Commonly, the color of pH indicator changes in response to the pH of the surrounding solution. pH indicators are well known in the art, and include, for example bromophenol blue, methyl red, litmus, phenolphthalein and phenol red.

A prothrombin time (PT) assay may be performed, for example, by incubating blood with citrate or other anticoagulant, and isolating the blood plasma. A substance is then added to the plasma to reverse the effects of the anticoagulant (e.g. in the case of citrate, calcium is added). Then tissue factor (factor (III)) is added to the plasma, and the time required for the sample to clot is measured. Clotting of the sample may, for example, increase the turbidity of the sample and/or increase its viscosity. The assay may be measured in a spectrophotometer, for example, by measuring absorbance of the sample.

A zinc protoporphyrin assay may be performed, for example, by incubating red blood cells with a solution to lyse the red blood cells (e.g. water or water containing 10 mM phosphate buffer, pH 7.4), and observing the fluorescence of the sample at EX/EM=424/594 nm, which are strong excitation and emission wavelengths for zinc protoporphyrin.

A chloride assay may be performed, for example, by incubating a biological sample (e.g. plasma, urine, etc.) with a reagent which has one color when in complex with a mercury atom, and which has a second color when in complex with an iron atom (e.g. 2,4,6-Tripyridyl-s-triazine (TPTZ) or thiocyanate). These reagents preferentially form complexes with mercury atoms over iron atoms. However, in the presence of chloride ions, mercury disassociates from the reagent and forms $HgCl_2$, and iron is able to form a complex with the reagent. The iron-containing complex may be colored and can be measured, for example, in a spectrophotometer: Fe-TPTZ at 620 nm or Fe-thiocyanate at 480 nm.

A triglycerides assay may be performed, for example, by incubating a biological sample (e.g. plasma, etc.) with lipase enzyme, which can convert triglycerides to glycerol and fatty acids. Glycerol may then be incubated with additional enzymes which react with glycerol and and products thereof, ultimately resulting in the formation of hydrogen peroxide (in an example, glycerol kinase catalyzes the reaction of glycerol and ATP to form glycerol phosphate, and glycerol-3-phosphate oxidase catalyzes the conversion of glycerol phosphate to dihydroxyacetone phosphate and hydrogen peroxide). The reaction may be incubated with a peroxidase and oxidizable substrate (e.g. a chromogen or fluorescent dye), the oxidation of which may be monitored (for example, with a spectrophotometer).

A total cholesterol assay may be performed, for example by incubating a biological sample (e.g. plasma, etc.) with cholesterol esterase (to convert cholesteryl ester to cholesterol) and cholesterol oxidase (to convert cholesterol to cholest-4-ene-3-one, and simultaneously producing hydrogen peroxide). The reaction may be incubated with a peroxidase and an oxidizable substrate (e.g. a chromogen or fluorescent dye), the oxidation of which may be monitored (for example, with a spectrophotometer).

An albumin assay may be performed, for example, by incubating a biological sample (e.g. plasma, urine, etc.) with a dye which binds to albumin, such as 5',5"-dibromo-o-cresolsulfophthalein (Bromocresol Purple (BCP)) or Bromocresol Green (BCG)). The assays can be measured, for example, in a spectrophotometer by absorbance at 600 nm for BCP, or absorbance at 628 nm for BCG.

A total protein assay may be performed, for example, by incubating a biological sample (e.g. plasma, urine, etc.) with a reagent which binds to one or more structures in proteins (e.g. peptide bonds). These reagents include, for example, copper (II) ions (for the Biuret test) and Coomassie™ dyes. Protein-dye complexes may be further stabilized by incubating the complexes with another reagent, such as bicinchoninic acid (BCA) (for the BCA test). For assays with copper (II) ions, the samples can be measured, for example in a spectrophotometer at 540 nm. For assays with a Coomassie™ dye, the samples can be measured, for example in a spectrophotometer at 595 nm.

A bicarbonate/carbon dioxide assay may be performed, for example, by adjusting the pH of biological sample (e.g. plasma, urine, etc.) to a pH greater than 7, so that carbon dioxide in the sample is converted to bicarbonate ($HCO_3^-$). Phosphoenolpyruvate (PEP) and phosphoenolpyruvate carboxylase (PEPC) are provided to the sample, such that PEPC catalyzes the reaction between PEP and bicarbonate to form oxaloacetate and phosphate. The oxaloacetate may be detected by a variety of mechanisms. For example, oxaloacetate may be incubated with NADH and malate dehydrogenase, in which malate dehydrogenase catalyzes the conversion of oxaloacetate and NADH to malate and NAD+. The reaction may be monitored by measuring absorbance at 340 nm, to monitor the level of NADH. In another example, oxaloacetate may be incubated with a chromogen which can form a complex with oxaloacetate, such as Fast Violet B. The reaction may be monitored, for example, in a spectrophotomer measuring the absorbance at 578 nm, to monitor the level of oxaloacetate-Fast Violet B complex.

An aspartate aminotransferase (AST/SGOT) assay may be performed, for example, by incubating a biological sample (e.g. plasma, urine, etc.) with one or more substrates for aspartate aminotransferase (e.g. aspartate and alpha-ketoglutarate). Aspartate aminotransferase in the sample may catalyze the transfer of an amino group from aspartate to alpha-ketoglutarate, to form oxaloacetate and glutamate. Malate dehydrogenase may also be provided in the assay, which may catalyze the conversion of oxaloacetate to malate, coupled with the oxidation of NADH to NAD+. Lactate dehydrogenase may also be provided in the assay, to reduce interference from pyruvate. The assay may be monitored by absorbance at 340 nm, at which NADH absorbs (i.e. the more NADH is consumed, the lower the absorbance at 340 nm). The rate of conversion of NADH to NAD+ may be directly proportional to the quantity of aspartate aminotransferase in the sample.

A blood urea nitrogen (BUN) assay may be performed, for example, by incubating a biological sample (e.g. plasma, urine, etc.) with urease, which may cleave urea in the sample to yield carbon dioxide and ammonia. The ammonia may then be involved in a reaction which may be readily monitored. In an example, the ammonia may be incubated with ammonia and alpha-ketoglutarate in the presence of glutamate dehydrogenase and NADH, to yield glutamate and NAD+. The assay may be monitored by absorbance at 340 nm, at which NADH absorbs; the rate of conversion of NADH to NAD+ may be directly proportional to the quantity of urea in the sample. In another example, ammonia may be incubated with salicylate and sodium nitroprusside, and then with hypochlorite, to yield a blue-green colored product, which may be measured, for example, in a spectrophotometer at 630 nm.

A total bilirubin assay may be performed, for example, by incubating a biological sample (e.g. plasma, urine, etc.) with a reagent that converts bilirubin to a readily detectable molecule. For example, a sample may be incubated with sulfanilic acid and sodium nitrite to convert bilirubin to an azobilirubin form which may, for example, be readily detected in a spectrophotometer by absorbance at 550 nm.

A creatinine assay may be performed, for example, by incubating a biological sample (e.g. plasma, urine, etc.) with creatininase, which that converts creatinine to creatine. Creatine may then be converted to sarcosine by creatine amidinolydrolase. Sarcosine oxidase may then catalyze the reaction of sarcosine with water and oxygen to form glycine, formaldehyde, and hydrogen peroxide. The hydrogen peroxide may be used with any oxidizable chromogen or other detectable agent described herein, according to methods disclosed elsewhere herein. The level of the oxidized product may be directly proportional to the quantity of creatinine in the sample.

It should be understood that for substantially all of the foregoing, two or more of these assays may be performed in a system using multiple detection methods (which may be the same or different) using the same system. This simultaneous processing of at least two, optionally three or more assays, within the same device (or optionally using the same system) using aliquots from the same sample provides substantial advantages over known systems due to savings in at least the reduced amount of sample used and the reduced processing time for the multiple assays.

Immunoassays

Many assays use antibody-antigen binding to detect analytes, and to quantitate analyte amounts where present. For example, ELISAs are useful assays that utilize antibodies for identifying protein or small molecule targets. ELISAs are suitable for use in automatic assay devices and systems. In a typical ELISA assay, a sample containing or suspected to contain the antigen of interest is immobilized on a support (e.g., a wall within a well, a pipette tip, a bead, or other support having a surface for immobilization) either non-specifically (e.g., via adsorption to the surface) or specifically (e.g., via capture by another antibody specific to the same antigen, in a "sandwich" ELISA). After the antigen is immobilized the detection antibody is added, forming a complex with the antigen. The detection antibody can be conjugated to an enzyme, or can itself be detected by a secondary antibody which is in turn conjugated to an enzyme. Upon addition of a substrate for the conjugated enzyme, a detectable signal is generated which indicates the presence and/or quantity of the antigen in the sample. The choice of substrates will depend on the enzyme conjugated. Suitable substrates include fluorogenic and chromogenic substrates. There are multiple parameters that can be modified to increase the signal detected as well as other variations of ELISAs known in the art.

In some ELISAs, a solid phase capture surface can include an attached first antibody to which a sample (e.g., diluted blood, plasma, or biological specimen) can be added. If present, an analyte in the sample can bind to the first antibody and become immobilized. An enzyme reagent can be added that includes, for example, an antibody coupled or conjugated to an enzyme (e.g., alkaline phosphatase or horseradish peroxidase) that produces a detectable product, or can be otherwise detected. If the antibody portion of the enzyme reagent can bind the analyte, then the enzyme reagent also becomes immobilized at the capture surface. Addition of a substrate for the enzyme can result in a product producing an effect, for example, light that can be measured and plotted as shown. In this manner the amount of analyte present in a sample can be measured.

Thus, for example, an exemplary ELISA which may be performed using an automatic assay device may utilize a solid phase capture surface on which a first antibody is immobilized. The first antibody is typically specific for a test antigen (e.g., antibody specific for a target blood analyte, such as cholesterol, or for e.g., neuraminidase on the coat of a virus of interest, or other antigen). If the test antigen is present in a test sample (e.g., whole blood, plasma, or serum) that is exposed to the antibody immobilized on the surface, then the test antigen can become immobilized (captured) at the capture surface. Addition of a second, labeled antibody that binds to the first antibody (e.g., where the first antibody has a biotin label, and the second antibody has an avidin label and a detectable label; or where the first antibody is a sheep antibody including an Fc portion, the second antibody may be an antibody targeting sheep Fc and labeled with alkaline phosphatase (AP) which can be detected following addition of AP substrate) allows the detection and quantification of the amount of antigen in the sample. The first antibody, which is bound to the substrate, is not washed out by the addition of the second antibody. Such detection and quantification may be accomplished by providing substrate for alkaline phosphatase, leading to the production of colored, fluorescent, luminescent (e.g., chemiluminescent), or otherwise detectable compounds which may be detected and measured.

In embodiments, multiple analytes may be detected or quantified in a sample by ELISA assays. For example, after a blood sample is placed in contact with the surface having the immobilized first antibody (labeled with an enzyme which catalyzes a reaction that produces a first detectable compound) that targets a first antigen, a second antibody, targeting a second antigen and labeled with a second enzyme which can produce a second detectable compound may be added. The first antibody, which is bound to the substrate, is not washed out by the addition of the second antibody, and may be detected by providing the substrate and proper reaction conditions for the production of a first detectable product by an enzyme linked to the first antibody. Binding and subsequent detection of the second, labeled antibody at the capture surface indicates the presence of both the first and the second test antigens in the test sample. Both the first and second detectable compounds produced by the enzymes linked to the antibodies may be detected by any means desired, including by detection of fluorescence, luminescence, chemiluminescence, absorbance, or other means for detecting the products of the enzymatic reactions due to the attached enzymes.

Photomultipliers tubes, charge-coupled devices, photodiodes, cameras, spectrophotometers, and other optical sensors, components, and devices may be used to measure light emitted or affected during the performance of an ELISA. For example, the amount of light detected (e.g., in relative light units, or other measurements of luminosity) during the performance of an ELISA on a sample may be compared to a standard curve (e.g., a calibration curve prepared for a particular assay, device, cartridge, or reagent) to calculate the concentration of the target analyte in the sample. Target analytes that have been detected and their levels measured in blood samples using ELISAs performed on automatic devices and systems include, for example: vitamin B-12, folic acid, thyroxine, testosterone, estradiol, cotinine, vancomycin, hemoglobin A1c, prostate specific antigen, human chorionic gonadotropin, luteinizing hormone, parathyroid hormone, alpha-fetoprotein, prealbumin, cardiac troponin T, C-reactive protein, hepatitis B surface antigen (HbsAg), immunoglobulin E (IgE), immunoglobulin G (IgG), Dengue virus IgG, rheumatoid factor IgM, West Nile Virus IgM, anti-HIV 1 antibodies, anti-HIV 2 antibodies, anti-nuclear antibodies, influenza A, influenza B, and *streptococcus*.

ELISAs are also used, for example, in competitive binding experiments, in which the concentration of an analyte in a solution may be measured by adding a known amount of labeled analyte, and measuring the binding of the analyte. Increased concentrations of the sample analyte (which does not include the label) interfere ("compete") with the binding of the labeled analyte, allowing calculation of the amount of analyte in the sample.

Nucleic Acid Assays

In some embodiments, the analyte is a target nucleic acid (e.g. DNA, RNA, mRNA, miRNA, rRNA, tRNA, and hybrids of these) that is detected in a nucleic acid hybridization reaction. Target nucleic acid in a sample may be a nucleic acid from the subject from which the sample is derived, or from a source to which the subject providing the sample is a host, such as a pathogen as described herein. In general, hybridization refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of an amplification process (e.g. PCR, ligase chain reaction, self-sustained sequence replication), or the enzymatic cleavage of a polynucleotide by an endonuclease. A sequence capable of hybridizing with a given sequence is referred to as the "complement" of the given sequence. In some embodiments, hybridization occurs between a target nucleic acid (analyte) and a nucleic acid probe. In some embodiments, a target nucleic acid is modified before hybridization with a probe, such as by the ligation of an adapter to one or both ends of a target nucleic acid to generate a modified target nucleic acid. In a modified nucleic acid comprising a linker, a probe may hybridize only to linker sequence, only to target nucleic acid sequence, or to both linker and target nucleic acid sequence. Non-limiting examples of uses for nucleic acid probes include detecting the presence of viral or bacterial nucleic acid sequences indicative of an infection, detecting the presence of variants or alleles of mammalian genes associated with disease and cancers, genotyping one or more genetic loci (e.g. single nucleotide polymorphisms), identifying the source of nucleic acids found in forensic samples, and determining paternity.

A nucleic acid probe may comprise DNA, RNA, modified nucleotides (e.g. methylated or labeled nucleotides), modified backbone chemistries (e.g. morpholine ring-containing backbones), nucleotide analogs, or combinations of two or more of these. A probe can be the coding or complementary strand of a complete gene or gene fragment, or an expression product thereof. The nucleotide sequence of the probe can be any sequence having sufficient complementarity to a nucleic acid sequence in a biological sample to allow for hybridization of the probe to the target nucleic acid in the biological sample under a desired hybridization condition. Ideally, a probe will hybridize only to a nucleic acid target of interest in the sample and will not bind non-specifically to other non-complementary nucleic acids in the sample or other regions of the target nucleic acid in the sample. The hybridization conditions can be varied according to the degree of stringency desired in the hybridization reaction. For example, if the hybridization conditions are for high stringency, the probe will bind only to the nucleic acid sequences in the sample with which it has a very high degree of complementarity. Low stringency hybridization conditions will allow for hybridization of the probe to nucleic acid sequences in the sample which have some complementarity but which are not as highly complementary to the probe sequence as would be required for hybridization to occur at high stringency. The hybridization conditions will vary depending on the biological sample, probe type and target.

A nucleic acid probe can be commercially obtained or can be synthesized according to standard nucleotide synthesizing protocols well known in the art. Alternatively, a probe can be produced by isolation and purification of a nucleic acid sequence from biological materials according to methods standard in the art of molecular biology (Sambrook et al. 1989. Molecular Cloning: A Laboratory Manual, 2d Ed., Cold Spring Harbor Laboratory Pres, Cold Spring Harbor, N.Y.). A nucleic acid probe can be amplified according to known procedures for amplification of nucleic acid (e.g., PCR). Furthermore, a probe can be linked to a label by known protocols.

Labels to which a nucleic acid probe can be linked to include, but are not limited to, a hapten, biotin, digoxigenin, fluorescein isothiocyanate (FITC), dinitrophenyl, amino methyl coumarin acetic acid, acetylaminofluorene and mercury-sulfhydryl-ligand complexes, chromogenic dyes, fluorescent dyes, and any other suitable label as described herein, such as described in combination with labeling of analyte receptors. In some embodiments, hybridization is detected indirectly by detection of a product of a hybridization reaction, such as PCR. For example, amplification products may be detected by a dye or stain capable of detecting amplified nucleic acids (e.g. intercalating or groove-binding dyes), such as ethidium bromide, SYBR green, SYBR blue, DAPI, acriflavine, fluorcoumanin, ellipticine, daunomycin, chloroquine, distamycin D, chromomycin, propidium iodine, Hoeste, SYBR gold, acridines, proflavine, acridine orange, homidium, mithramycin, ruthenium polypyridyls, anthramycin, and other suitable agents known in the art. In some embodiments, multiple probes, each having a different target nucleic acid and a different label, are hybridized to a single sample simultaneously, such as about or more than about 1, 2, 3, 4, 5, 6, 7, 8, 9, 10, 11, 12, 13, 14, 15, 16, 17, 18, 19, 20, 30, 40, 50, 60, 70, 80, 90, or more different probes.

In one embodiment, nucleic acid probes are covalently or non-covalently coupled to a substrate. Non-limiting examples of substrates to which nucleic acid probes may be coupled include microarrays, microbeads, pipette tips, sample transfer devices, cuvettes, capillaries or other tubes, reaction chambers, or any other suitable format compatible with the subject detection system.

In some embodiments, the nucleic acid hybridization reaction is a sequencing reaction. Sequencing reactions may proceed directly from sample nucleic acids, or may involve a pre-amplification step, such as reverse transcription and/or PCR. Sequence analysis using template-dependent synthesis can include a number of different processes. For example, one of the earliest methods for DNA sequencing was the four-color chain-termination Sanger sequencing methodology in which a population of template molecules is used to create a population of complementary fragments. Primer extension is carried out in the presence of the four naturally occurring nucleotides, and with a sub-population of dye-labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the template beyond the primer, and are labeled in a manner that permits identification of the terminating nucleotide. The nested fragment population is then subjected to size-based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534, incorporated herein by reference in its entirety for all purposes).

Nucleic acid assays typically involve detection of nucleic acid analytes by detecting hybridization of a probe (having a known nucleic acid sequence) to complementary nucleic acid sequences in a sample. Often there are too few such complementary sequences in a typical sample, so that amplification of sample nucleic acids is required for detection. Amplification entails making multiple copies of the nucleic acid sequences in a sample in order to provide a sufficient number of target sequences for their detection. Methods for the amplification of nucleic acids, including DNA and/or RNA, are known, and many such methods are suitable for use on automatic assay devices and systems.

Nucleic acid amplification may comprise sequential, parallel, or simultaneous amplification of a plurality of nucleic acid sequences, such as about or more than about 10, 11, 12, 13, 14, 15, 20, 25, 30, 35, 40, 50, 100, or more target sequences. In some embodiments, a subjects entire genome or entire transcriptome is non-specifically amplified, the products of which are probed for one or more identifying sequence characteristics. An identifying sequence characteristic includes any feature of a nucleic acid sequence that can serve as a basis of differentiation between individuals. In some embodiments, an individual is uniquely identified to a selected statistical significance using about or more than about 10, 11, 12, 13, 14, 15, 20, 25, 30, 35, 40, 50, 100, or more identifying sequences. In some embodiments, the statistical significance is about, or smaller than about $10^{-2}$, $10^{-3}$, $10^{-4}$, $10^{-5}$, $10^{-6}$, $10^{-7}$, $10^{-8}$, $10^{-9}$, $10^{-19}$, $10^{-11}$, $10^{-12}$, $10^{-13}$, $10^{-14}$, $10^{-15}$, or smaller. Examples of identifying sequences include Restriction Fragment Length Polymorphisms (RFLP; Botstein, et al., Am. J. Hum. Genet. 32: 314-331, 1980; WO 90/13668), Single Nucleotide Polymorphisms (SNPs; Kwok, et al., Genomics 31: 123-126, 1996), Randomly Amplified Polymorphic DNA (RAPD; Williams, et al., Nucl. Acids Res. 18: 6531-6535, 1990), Simple Sequence Repeats (SSRs; Zhao & Kochert, Plant Mol. Biol. 21: 607-614, 1993; Zietkiewicz, et al. Genomics 20: 176-183, 1989), Amplified Fragment Length Polymorphisms (AFLP; Vos, et al., Nucl. Acids Res. 21: 4407-4414, 1995), Short Tandem Repeats (STRs), Variable Number of Tandem Repeats (VNTR), microsatellites (Tautz, Nucl. Acids. Res. 17: 6463-6471, 1989; Weber and May, Am. J. Hum. Genet. 44: 388-396, 1989), Inter-Retrotransposon Amplified Polymorphism (IRAP), Long Interspersed Elements (LINE), Long Tandem Repeats (LTR), Mobile Elements (ME), Retrotransposon Microsatellite Amplified Polymorphisms (REMAP), Retrotransposon-Based Insertion Polymorphisms (RBIP), Short Interspersed Elements (SINE), and Sequence Specific Amplified Polymorphism (SSAP). Additional examples of identifying sequences are known in the art, for example in US20030170705, which is incorporated herein by reference. A genetic signature may consist of multiple identifying sequences of a single type (e.g. SNPs), or may comprise a combination of two or more different types of identifying sequences in any number or combination.

Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. No. 5,527,670, U.S. Pat. No. 6,033,850, U.S. Pat. No. 5,939,291, and U.S. Pat. No. 6,333,157), and application of an electromagnetic field in combination with primers bound to a magnetically-responsive material (e.g. U.S. Pat. No. 5,545,540), which are hereby incorporated by reference in their entireties. In a variation called RT-PCR, reverse transcriptase (RT) is used to make a complementary DNA (cDNA) from RNA, and the cDNA is then amplified by PCR to produce multiple copies of DNA (e.g. U.S. Pat. No. 5,322,770 and U.S. Pat. No. 5,310,652, which are hereby incorporated by reference in their entirety). Other amplification methods include isothermal methods which do not require thermal cycling (which is required for PCR).

One example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product (e.g. U.S. Pat. No. 5,270,184 and U.S. Pat. No. 5,455,166, which are hereby incorporated by reference in their entirety). Thermophilic SDA (tSDA) uses thermophilic endonucleases and polymerases at higher temperatures in essentially the same method (European Pat. No. 0 684 315, which is hereby incorporated by reference in its entirety).

Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278), which are hereby incorporated by reference in their entirety. In some cases, isothermal amplification uses transcription by an RNA polymerase from a promoter sequence, such as may be incorporated into an oligonucleotide primer. Transcription-based amplification methods commonly used in the art include nucleic acid sequence based amplification, also referred to as NASBA (e.g. U.S. Pat. No. 5,130,238); methods which rely on the use of an RNA replicase to amplify the probe molecule itself, commonly referred to as Qβ replicase (e.g., Lizardi, P. et al. (1988) *BioTechnol.* 6, 1197-1202); self-sustained sequence replication (e.g., Guatelli, J. et al. (1990) *Proc. Natl. Acad. Sci. USA* 87, 1874-1878; Landgren (1993) *Trends in Genetics* 9, 199-202; and HELEN H. LEE et al., NUCLEIC ACID AMPLIFICATION T ECHNOLOGIES (1997)); and methods for generating additional transcription templates (e.g. U.S. Pat. No. 5,480,784 and U.S. Pat. No. 5,399,491), which are hereby incorporated by reference in their entirety. Further methods of isothermal nucleic acid amplification include the use of primers containing non-canonical nucleotides (e.g. uracil or RNA nucleotides) in combination with an enzyme that cleaves nucleic acids at the non-canonical nucleotides (e.g. DNA glycosylase or RNaseH) to expose binding sites for additional primers (e.g. U.S. Pat. No. 6,251,639, U.S. Pat. No. 6,946,251, and U.S. Pat. No. 7,824,890), which are hereby incorporated by reference in their entirety. Isothermal amplification processes can be linear or exponential.

A nucleic acid assay may utilize an optical sensor, and may utilize a thermal block to heat a solution or vessel. The optical sensor may be in-line with the well of a thermal block, or to the side of the well of the thermal block. There may be an opening or a channel in the wall of the well of thermal block creating an optical path between the interior of the well and the optical sensor. The nucleic acid assay station may also contain a light source. The light source may be attached to a movable portion of the assay station, configured such that in one or more positions of the movable portion, the light from the light source is directed into the well of the thermal block. In situations where the light source and the optical sensor are both in-line with the well of the thermal block (due to the light source and optical sensor having fixed or movable positions), various types of spectrophotometric readings of the sample may be obtained—e.g. absorbance, transmittance, or fluorescence. In situations where the optical sensor is at an angle to the light source and the well of the thermal block, spectrophotometric readings of the sample that may be obtained include, for instance, light scattering, fluorescence, and turbidity.

Cytometric Assays

Cytometric assays are typically used to measure characteristics of individual cells. Techniques used for cytometry include optical (e.g., microscopic and fluorometric), electrical (e.g., electronic), and acoustic techniques and equipment. For the purposes of this disclosure, "cells" may encompass non-cellular samples that are generally of similar sizes to individual cells, including but not limited to vesicles (such as liposomes), small groups of cells, virions, bacteria, protozoa, crystals, bodies formed by aggregation of lipids and/or proteins, and substances bound to small particles such as beads or microspheres. Such characteristics include but are not limited to size; shape; granularity; light scattering pattern (or optical indicatrix); whether the cell membrane is intact; concentration, morphology and spatio-temporal distribution of internal cell contents, including but not limited to protein content, protein modifications, nucleic acid content, nucleic acid modifications, organelle content, nucleus structure, nucleus content, internal cell structure, contents of internal vesicles (including pH), ion concentrations, and presence of other small molecules such as steroids or drugs; and cell surface (both cellular membrane and cell wall) markers including proteins, lipids, carbohydrates, and modifications thereof. By using appropriate dyes, stains, or other labeling molecules either in pure form, conjugated with other molecules or immobilized in, or bound to nano- or micro-particles, cytometry may be used to determine the presence, quantity, and/or modifications of specific proteins, nucleic acids, lipids, carbohydrates, or other molecules. Properties that may be measured by cytometry also include measures of cellular function or activity, including but not limited to phagocytosis, antigen presentation, cytokine secretion, changes in expression of internal and surface molecules, binding to other molecules or cells or substrates, active transport of small molecules, mitosis or meiosis; protein translation, gene transcription, DNA replication, DNA repair, protein secretion, apoptosis, chemotaxis, mobility, adhesion, antioxidizing activity, RNAi, protein or nucleic acid degradation, drug responses, infectiousness, and the activity of specific pathways or enzymes. Cytometry may also be used to determine information about a population of cells, including but not limited to cell counts, percent of total population, and variation in the sample population for any of the characteristics described above. The assays described herein may be used to measure one or more of the above characteristics for each cell, which may be advantageous to determine correlations or other relationships between different characteristics.

The assays described herein may also be used to independently measure multiple populations of cells, for example by labeling a mixed cell population with antibodies specific for different cell lines. An automatic assay device may include cytometry capabilities; e.g., may include microscopy and other cytometric capabilities. In embodiments, an automatic assay device may include a cytometry module; in embodiments, an automatic assay device may include a microscopy module. Cytometry may include flow cytometery and may include stationary cytometry (e.g., in which a sample, and cells and particles within the sample, does not flow but is stationary within a chamber, such as a cuvette).

A cytometry module or a microscopy module may permit the performance of histology, pathology, and/or morphological analysis with the device, and also facilitates the evaluation of objects based on both physical and chemical characteristics. Fluid samples may be examined directly, or may be pretreated, or diluted, or otherwise prepared for cytometric or microscopic analysis. Fluid samples may be introduced into a cuvette, and cells allowed or induced to settle, e.g., onto a transparent portion suitable for imaging. For example, tissues can be homogenized, washed, deposited on a cuvette or slide, dried, stained (such as with antibodies), incubated and then imaged, e.g., by a microscope. When combined with the data transmission technologies described elsewhere herein, these innovations facilitate the transmission of images from a CMOS/CDD or similar to a licensed pathologist for review, which is not possible with traditional devices that only perform flow cytometry. A cytometer can measure surface antigens as well as cell morphology; surface antigens enable more sensitive and specific testing compared to traditional hematology laboratory devices. The interpretation of cellular assays may be automated by gating of one or more measurements; the gating thresholds may be set by an expert and/or learned based on statistical methods from training data; gating rules can be specific for individual subjects and/or populations of subjects.

Cytometric analysis may use, for example, flow cytometry, stationary cytometry, or microscopy. Flow cytometry typically uses a mobile liquid medium that sequentially carries individual cells to an optical, electrical or acoustic detector. Microscopy typically uses optical or acoustic means to detect stationary cells, generally by recording at least one magnified image. Stationary cytometry uses optical methods to detect, identify, and analyze cells and particles in a sample while the cells are stationary within the sample, or within a cell or chamber (e.g., a cuvette). For example, a sample may be introduced into a cuvette, and cells and particles allowed to settle onto an optically transmissive (e.g., transparent) portion of the floor of the cuvette, through which light may be shone, and images and optical information obtained, regarding the sample and cells and particles within it. It should be understood that flow cytometry and microscopy are not entirely exclusive. Many of the targets, reagents, assays, and detection methods may be the same for flow cytometry and microscopy. As one example, flow cytometry assays may use microscopy to record images of cells passing by the detector. Cytmoetry includes cytometric observations and analysis made in non-flow conditions: e.g., when cells or particles form a sample are at rest in a sample, in a solution, or in contact with a substrate. For example, cytometry and microscopy may use fluorescence measurements, light scatter measurements, or other optical measurements to analyze samples, and cells and particles within the samples. As such, unless otherwise specified, the descriptions below should be taken to apply to these and other forms of cytometric analyses known in the art.

Flow cytometry may be used to measure, for example, cell size (forward scatter, conductivity), cell granularity (side scatter at various angles), DNA content, dye staining, and quantitation of fluorescence from labeled markers. Flow cytometry may be used to perform cell counting, such as by marking the sample with fluorescent markers and flowing past a sensing device. Cell counting may be performed on unlabeled samples as well.

Assay Improvement

An assay comprises a step or steps applied to a sample. Steps which may be performed in an assay include, without limitation, pretreatment steps, mixing steps, incubation steps, reaction steps, labeling steps, detecting steps, and other steps. An assay to be improved is termed a "baseline assay"; in embodiments, the process of improving an assay includes making changes in a step or steps of the baseline assay, and comparing the results of the baseline assay with the results of the assay in which the step or steps were changed. An assay in which the step or steps are changed, as compared with the baseline assay, is termed a "revised assay." A revised assay whose results compare satisfactorily with those of the baseline assay may be termed an "improved assay."

Assays may have more than one aspect, and may be improved by improvement of one or more aspect. Changes in a step, or in multiple steps, may improve an aspect, or may improve more than one aspect, of an assay. Improvement of an assay may improve at least one aspect, and may improve more than one aspect of the baseline assay (where an aspect of an assay may include, without limitation, the accuracy, precision, reliability, simplicity, speed, cost, or other aspect of an assay or of an assay step). As discussed herein, improvement of an assay typically requires that the baseline assay be changed in one or more ways; that is, at least one step of the assay will be changed during the process of improvement, and the resulting, improved assay will differ from the baseline assay in the performance of at least one step. For example, without limitation, a revised assay may differ from a baseline assay in the volume of sample used in the assay; in the type or extent of pretreatment of the sample (e.g., aliquotting, filtration, centrifugation, or other pretreatment); in the timing of a treatment applied to the sample (e.g., time of initiation of a treatment, duration of a treatment, sequence of treatments); in the temperature at which the assay is performed; in the composition of a reagent used in the assay; in the type or extent of a chemical reaction used in the assay; in the type of detection used in the assay; in the particulars of such detection (e.g., the wavelength or wavelengths of light used in an optical detection step); in the timing of detection; in whether or not additional analytes or characteristics are also detected in the assay; in the method of reporting results detected by the assay; and in other aspects and combinations of aspects.

Revised assays may differ from baseline assays in one or more ways. For example, differences between a revised assay and a baseline assay may include differences in the requirements for sample volume, and an improvement may include a reduction in the sample volume required for the assay. For example, differences between a revised assay and a baseline assay may include differences in reagent requirements, and an improvement may include a reduction in the volume of reagents required, or a reduction in the number of reagents required to perform the assay. For example, differences between a revised assay and a baseline assay may include differences in assay sensitivity, and an improvement may include an increase in that sensitivity of the assay. For example, differences between a revised assay and a baseline assay may include differences in the time required to complete the assay, and an improvement may include a reduction in the time required to complete the assay. For example, differences between a revised assay and a baseline assay may include differences in cost, and an improvement may include a reduction in the cost of performing the assay. Further examples include, without limitation, that a revised assay may have a different number of steps than a baseline assay (e.g., a revised assay may require fewer steps than a baseline assay); a revised assay may be performed at a different temperature than the temperature used to perform a baseline assay; a revised assay may be performed more rapidly than a baseline assay; a revised assay may be performed with fewer reagents than are required to perform a baseline assay; a revised assay may combine two assays into a single assay, or into a compatible sequence of steps, to provide a revised assay which provides results regarding more analytes than a baseline assay; a revised assay may be less expensive to perform than a baseline assay; and may differ from a baseline assay in other ways. In embodiments of improvement of an assay, any part or detail of a step of an assay may be altered in an attempt to improve an assay.

However, improvement of an assay need not improve all aspects of an assay; in embodiments, improvement of an assay may leave some, or even many, aspects of an assay unchanged, while improving at least one aspect of the assay. In embodiments, one aspect of an assay may be selected for improvement. In embodiments, more than one aspect of an assay may be selected for improvement. In embodiments, one aspect of an assay may be identified as not being in need of improvement. In embodiments, more than one aspect of an assay may be identified as not being in need of improvement. Once a baseline assay is selected, the process of improvement of that assay may begin.

During the process of improvement, a revised assay, or multiple revised assays, are run and the results of these revised assays (termed "revised assay results") are compared to the baseline results in order to determine how well the revised assays match the baseline results. The results of such revised assays may be worse than the results of the baseline assay; or may be similar to the results of the baseline assay; or may be substantially equal to the results of the baseline assay; or may be better than the results of the baseline assay. Revised assays which provide results that are similar to, or substantially equal to, or better than the results of the baseline assay are noted, and considered candidates for further improvement. A goal of improvement is to identify a revised assay, or multiple revised assays, which provide results that are substantially equal to, or better than the results of the baseline assay. Determination of what constitutes results that are results that are substantially equal to, or better than the results of the baseline assay will depend on the aspect, or aspects, of the baseline assay selected for improvement. Where speed is selected for improvement, revised assays that provide reliable results in less time than the baseline assay will be sought; where small sample volume is selected for improvement, revised assays that provide reliable results with less sample than required for the baseline assay will be sought; where cost is selected for improvement, revised assays that provide reliable results with less cost than the baseline assay will be sought. It will be understood that other aspects, and other parameters, may be improved. In embodiments where multiple aspects or parameters are to be improved, combinations of improvements in different aspects or parameters will determine which revised assays are better than other revised assays, and are better than the baseline assay.

Processes for Improving Assays

In order to improve an assay, an assay which is to be improved must first be selected. The assay which is to be improved is termed a "baseline assay" and the results of this baseline assay are termed "baseline results." Any assay may be selected as a baseline assay. A baseline assay may be selected because the analyte identified by the assay is an analyte of interest. A baseline assay may be selected because the assay is needed, but may be difficult to perform, or expensive, or unreliable, or slow, or have other drawbacks. A baseline assay may have no obvious drawbacks, but improvement may be desired to improve the assay. As disclosed herein, an improved assay may provide advantages as compared to a baseline assay; that is, an improved assay may be an improvement over a baseline assay. For example, an improved assay may provide more accurate results than a baseline assay; may provide more rapid results than a baseline assay; may provide results more inexpensively than a baseline assay; may be more sensitive than a baseline assay; may be more reliable than a baseline assay; may require fewer steps than a baseline assay; may require fewer reagents than a baseline assay; may utilize more stable reagents than a baseline assay; or may provide other advantages or combinations of these and other advantages as compared to a baseline assay.

Altering or changing an aspect of an assay typically entails altering or changing an assay step to provide a revised assay. Methods for improving an assay, including iterative methods for improving an assay, may include, without limitation, steps of: altering a step of a baseline assay; deleting a step of a baseline assay; adding a step to a baseline assay; altering the order of steps in a baseline assay; altering a reagent, or multiple reagents, used in a baseline assay; altering the temperature of a step, or of multiple steps, of a baseline assay; altering detection of results of a baseline assay; combinations of these; and otherwise altering a step or aspect of a baseline assay to provide a revised assay which differs from a baseline assay. Assay steps may include, without limitation: pretreating, diluting, aliquotting, separating, transporting, mixing, incubating, reacting, labeling, and detecting steps, as well as other steps. Altering a step may include altering a component, or multiple components, of a reagent. Altering a step may include altering a condition of a step (e.g., altering the pH of a reagent, or altering the step temperature, or other change). Altering a reagent used in an assay may include altering the pH, or osmolarity, or other aspect, of the reagent; thus, an alteration may include, or may affect, more than one aspect or condition of an assay.

Altering or changing a first assay step may require, or may be better accomplished, if a second assay step is also changed, e.g., in a complementary or compensating manner. Such complementary of compensating changes may include, without limitation, one or more of the following examples of changes. For example, if a step is changed by being eliminated, or by its duration being shortened, then the timing of subsequent steps may be altered, or the duration of subsequent steps may be altered, or the sequence of subsequent steps may be altered, to accommodate that change. For example, if the concentration of an active ingredient in a reagent is increased, the duration of a reaction step may be shortened to accommodate that change. For example, if a catalyst or other agent is added to a reagent, increasing the rate or extent of a reaction effected by a reagent, the duration of a reaction step may be shortened to accommodate that change. For example, if two or more steps are combined, the timing of subsequent steps may be altered, or the sequence of subsequent steps may be altered to accommodate that change. For example, if the temperature, or amount or duration of applied energy (e.g., ultrasonic energy) or radiation (e.g., electromagnetic radiation) in a step is changed, the duration of the step, or the duration or sequencing of other steps, may also be changed in order that the reaction, or the effect of the energy or radiation, remains or is improved or enhanced. For example, if a first reagent is changed, other reagents (e.g., with which the first reagent reacts, or which the first reagent affects) may also be changed in order that the reaction, or the effect, remains or is improved. For example, if a labeling step is changed, a detection step may be changed to accommodate the change in the labeling step so as to allow or improve the detection of the label.

For example, a process of altering a baseline assay, where such alterations are with respect to the conditions and requirements of the baseline assay, may include some or all of the following:

Defining the kinetics of the assay (e.g., whether to use kinetic assays, end-point assays, or both);

Identifying the expected range of assay results that may be obtained from the assay when applied to samples obtained from a wide range of subjects;

Identifying, and preferably demonstrating, a reasonable assay response across this range of expected assay results;

Selecting an appropriate and suitable calibrator (to serve as a control), with a preference for simple and readily available calibration reagents;

Selecting a suitable sample type (e.g., untreated, or filtered, or pre-treated in other ways) with a preference for no or minimal pre-treatment of the sample;

Selecting a suitable sample volume for use in the assay, with a preference for small volumes (e.g., <1 uL of plasma or other liquid sample);

Selecting a suitable diluent compatible with the sample, the analyte, and the reagents used in the assay;

Selecting a suitable target sample dilution factor for at least a first step in the assay, in order that the assay results will be expected to all fall within a detectable range (as expected from the possible range of samples from a wide range of subjects), thereby providing an altered sample dilution if required;

Selecting a suitable second and subsequent target sample dilution factor(s) for one or more subsequent steps in the assay, if the assay may require a second or subsequent dilution(s) in order that the assay results will be expected to all fall within a detectable range, thereby providing a further altered sample dilution if required;

Selecting a suitable assay temperature, for one, some, or all steps;

Selecting a suitable active ingredient concentration for a first ingredient of a reagent to be used with samples diluted by the selected sample dilution factor, thereby providing an altered reagent composition if required;

Where necessary, adapting all active ingredient concentrations in concert with each other so that all ingredients may be used at the dilution factor (or factors if the sample may be diluted a first time and a second or more times during the performance of the assay) used in the assay;

Combining two or more steps where possible (e.g., where the baseline assay includes two steps, each of which comprises addition of a reagent, and where the two reagents are mutually compatible, the two steps may be performed together as one step);

Combining detection steps of an assay, so that one assay uses both kinetic measurements and end-point measurements to obtain more data than was obtained with each measurement alone;

Deleting any step which may be omitted without significantly compromising the integrity of the results of the assay;

Adding any additional steps as may be required in order to provide suitable assay results;

Selecting suitable step durations, and a suitable assay duration (the total time taken to perform all assay steps) compatible with the assay temperature, sample volume, sample dilution, and reagent concentrations obtained from the preceding steps, with a preference for shorter duration steps, and a shorter assay duration, whenever possible; and Selecting or altering other assay parameters so as to be suitable for use in the revised assay based on the range of assay results expected from samples obtained from a wide range of subjects.

It will be understood that, in the practice of the methods disclosed herein that not all of the steps discussed above need be applied in every instance, but that instead, some baseline assays may be improved by application of only some of the above-mentioned steps, and that one baseline assay may require a different subset, or combination, of the above-mentioned steps than does another baseline assay. In embodiments, some baseline assays may be improved by application of all of the above-mentioned steps, and some baseline assays may be improved only by application of all of the above-mentioned steps. However, in embodiments, some baseline assays may be improved by application fewer than all of the above-mentioned steps for improving assays.

Assay Steps

An assay may include treatment of a sample, e.g., contacting a sample with a reagent which may react with, or alter, the sample and make detection of an analyte easier, or make such detection possible. An assay may include treatment of a sample, e.g., contacting a sample with a reagent which may react with, or alter, the sample and make measurement of an a property of the sample easier, or make such measurement possible. An assay may include pretreatment steps, which precede a treatment step or steps; an assay may include steps which follow a treatment step or steps; an assay may include detection steps which effect detection of, or measurement of, an analyte or sample property; and may include other treatment steps.

For example, the alteration of a pretreatment step of a baseline assay may include, without limitation: deleting a pretreatment step; shortening the duration of a pretreatment step; changing the temperature of a pretreatment step; changing a reagent used in a pretreatment step; mixing or combining reagents used in a pretreatment step; and combinations thereof.

In embodiments, pretreatment steps may include separation steps; aliquotting a sample (e.g., removing a portion of a sample from the baseline sample; or dividing the sample into two or more portions (which may or may not be of equal size or volume)) is one type of separation step. A settling step may be a type of separation step. A settling step may include, for example, a step of allowing a sample to sit effective that a portion, or portions, of the sample may settle over time. In embodiments, pretreatment steps may include other types of separation steps (e.g., steps which allow, or cause, a portion, or portions, of the sample to separate from each other). Such other types of separation steps may include, without limitation: centrifugation steps; coagulation steps; application of beads, microspheres, or other separation agents; capillary separation steps; electrophoretic steps; chromatographic steps; solvent-based separation steps; gel-based separation steps; membrane-based separation steps; filtration steps; and other steps. Alteration of such pretreatment steps may include, without limitation, alteration of the duration of the separation step; or of the temperature at which the separation occurs; or of the speed or duration of centrifugation; or of the concentration of coagulant used, or of the amount of beads, microspheres, or other separation agents used; or of the type, length, or solvents used in a chromatographic or electrophoretic step; or of the membrane composition, or thickness, or surface area, of other property of a membrane used; or of other conditions.

In embodiments, pretreatment steps may include dilution steps. In embodiments, a dilution step may include, without limitation: addition of a diluent to a sample, or may include addition of a sample, e.g., an aliquot of a sample, to a volume of diluent. A dilution step may include multiple dilutions, e.g., may comprise serial dilutions, to provide a highly diluted sample, or to provide a plurality of diluted samples which may be of the same, or of different, levels of dilution. In embodiments, a dilution step may include a mixing step, e.g., a step of mixing the combined sample and diluent. In embodiments, a dilution step may provide a diluted sample preparation, or multiple diluted sample preparations, one or more of which may comprise dilutions of 2, 3, 4, 5, 10, 20, 30, 40, 50, 100, 200, 300, 500, 700, 1000, $1\times10^4$, $2\times10^4$, $3\times10^4$, $5\times10^4$, $7\times10^4$, $1\times10^5$, $2\times10^5$, $3\times10^5$, $5\times10^5$, $7\times10^5$, $1\times10^6$-fold or more. Alteration of such dilution steps may include, without limitation, alteration of the amount of dilution (e.g., altering a 10-fold dilution to become a 100-fold dilution); or of the volume of the sample taken for dilution (e.g., altering the amount of an initial aliquot of sample to be diluted); or of the volume of the diluted sample (e.g., altering the amount of a diluted sample taken for a further dilution step in a serial dilution protocol); or of the number of dilutions in a serial dilution protocol; or of the temperature at which the dilution occurs; or of the nature of the diluent used; or of the concentration of the diluent used; or of the amount of mixing of the combined sample and diluent; or of other dilution conditions.

In embodiments, pretreatment steps may include, without limitation: contacting a sample with a reagent, such as EDTA, or heparain, or other reagent. A pretreatment step comprising contacting a sample with a reagent may include a step of incubating the sample and the reagent for a period of time, or at a specific temperature, or under specific conditions. Alteration of such pretreatment steps may include, without limitation, alteration of the period of time, or of the temperature, or of other conditions.

In embodiments, mixing steps may include, without limitation: stirring a sample; agitating a sample; sonicating a sample; rotating a sample container; aspirating a sample, or a portion of a sample from a container; aspirating a sample, or a portion of a sample from a container, and returning some or all of that sample or portion to the container; repeated aspiration and returning of some or all of a sample from and to a container; contacting a sample with a reagent; stirring a mixture containing a sample and a reagent; agitating a mixture containing a sample and a reagent; sonicating a mixture containing a sample and a reagent; rotating a container holding a mixture containing a sample and a reagent; aspirating a mixture containing a sample and a reagent, or a portion of such a mixture, from a container; aspirating a mixture containing a sample and a reagent, or a portion of such a mixture, from a container, and returning some or all of that mixture or portion to the container; repeated aspiration and returning of some or all of a mixture containing a sample and a reagent from and to a container; and combinations thereof. For example, altering a mixing step of a baseline assay may include, without limitation: deleting a mixing step; altering the amount of sample used in a mixing step; altering the amount of reagent used in a mixing step; altering the relative amounts of sample and reagent used in a mixing step; changing a reagent used in a mixing step; combining reagents used in a mixing step; altering the method of mixing used in a mixing step; shortening the duration of a mixing step; changing the temperature of a mixing step; changing the time at which a mixing step is performed; and combinations thereof.

In embodiments, incubation steps may include, without limitation: holding a sample, or a portion of a sample, in a container; holding a diluted sample, or a diluted portion of a sample, in a container; holding a mixture comprising a sample, or comprising a portion of a sample, in a container; holding a sample, or a portion of a sample, in a container following contacting the sample, or portion of a sample, with a reagent; holding a sample, or a portion of a sample, in a container following contacting the sample, or portion of a sample, with a label; holding a sample, or mixture comprising a sample or a portion of a sample, in a container at an incubation temperature; or combinations thereof. For example, altering an incubation step of a baseline assay may include, without limitation: deleting an incubation step; shortening the duration of an incubation step; changing the temperature of an incubation step; changing a reagent used in an incubation step; mixing or combining reagents used in an incubation step; changing the time at which an incubation step is performed; and combinations thereof.

In embodiments, a reaction step comprises a step in which a chemical, physical or other reaction occurs which includes at least a portion of a sample as a reactant. In embodiments, reaction steps may include, without limitation: combining a sample, or a portion of a sample, with a reagent; combining or contacting a sample with a substrate of an enzymatic reaction; combining or contacting a sample, or a portion of a sample, with a physical agent or material, such as, e.g., a stirring bar, a bead or plurality of beads, a chelating agent, a dessicant, an absorbent material, a gel, or other physical agent or material; combining or contacting a sample with a separation agent; applying heat to a sample or a mixture comprising a sample; cooling a sample or a mixture comprising a sample; exposing a sample, or a mixture comprising a sample, to electromagnetic energy, such as, e.g., light, microwave, or radiofrequency radiation; exposing a sample, or a mixture comprising a sample, to ultrasonic energy; or combinations thereof.

For example, altering a reaction step of a baseline assay may include, without limitation: deleting a reaction step; shortening the duration of a reaction step; changing the temperature of a reaction step; changing a reagent used in a reaction step; mixing or combining reagents used in a reaction step; changing the time at which a reaction step is performed; altering the intensity, duration, or wavelength of electromagnetic energy applied in a reaction step; altering the intensity, duration, or wavelength of ultrasonic energy applied in a reaction step; altering the particular physical agent or material used in a reaction step; altering the type of physical agent or material used in a reaction step; altering the duration of use of a physical agent or material in a reaction step; and combinations thereof.

In embodiments, an assay may include a labeling step; in embodiments, a reaction step of an assay may comprise a labeling step. In embodiments, labeling steps, and reaction steps comprising labeling steps may include, without limitation: contacting a sample, or portion of a sample, with a label; contacting a sample, or portion of a sample, with a reagent comprising a label, e.g., contacting a sample, or portion of a sample, with a labeled antibody, or a labeled nucleic acid molecule, or a labeled molecule which specifically binds to a sample, or portion of a sample, or an analyte in a sample, or in a portion of a sample; contacting a sample with a reagent which, upon combination with, or chemical reaction with, a sample, portion of a sample, or analyte within a sample, forms a detectable label; contacting a sample with a reagent which, upon combination with, or chemical reaction with, another compound or element present in, or added to, a sample or portion thereof forms a detectable label; contacting a sample with an enzyme which, upon combination with, or chemical reaction with, a sample, portion of a sample, or analyte within a sample, forms a detectable label; contacting a sample with an enzyme substrate which, upon combination with, or chemical reaction with, a sample, portion of a sample, or analyte within a sample, forms a detectable label; and combinations thereof.

For example, altering a labeling step of a baseline assay may include, without limitation: deleting a labeling step; changing (e.g., shortening) the duration of a labeling step; changing the temperature of a labeling step; adding a label used in a labeling step; changing a reagent used in a labeling step; changing a label used in a labeling step; mixing or combining labels used in a labeling step; adding an excitation step for use with a labeling step; changing an excitation step used with a labeling step; changing the time at which a labeling step is performed; changing the amount or duration of mixing during a labeling step; and combinations thereof.

In embodiments, an assay may include a detecting step. In embodiments, a detecting step may include, without limitation: detecting the level of a sample, or of a portion of a sample, within a container (e.g., detecting the level of a boundary between two components of a sample, or of a portion of a sample; or detecting the level of a meniscus of a sample, or of a portion of a sample, within a container); detecting the pH of a sample, or of a portion of a sample; detecting the partial pressure of a gas within a sample, or of a portion of a sample; detecting the concentration of an ion in a sample, or of a portion of a sample; detecting the concentration of an element or compound in a sample, or of a portion of a sample; detecting the partial pressure of a gas within a sample, or of a portion of a sample; detecting the temperature of a sample, or of a portion of a sample; detecting the concentration of a constituent of a sample, or of a portion of a sample (e.g., of an analyte in the sample); detecting a label; detecting an optical property of a sample or of a portion of a sample; detecting radiation; detecting the transmission of radiation through a sample, or a portion of a sample; detecting the absorbance of radiation through a sample, or a portion of a sample; detecting the effect on a property of radiation caused by transmission of radiation through a sample, or a portion of a sample (e.g., optical rotation, polarization, or other optical property); and combinations thereof.

For example, altering a detecting step of a baseline assay may include, without limitation: deleting a detecting step; shortening the duration of a detecting step; changing the temperature of a detecting step; changing a reagent used in a detecting step; mixing or combining reagents used in a detecting step; changing the detector used in a detecting step; changing the time at which a detecting step is performed; and combinations thereof. Altering a detecting step may include adding an additional detecting step to a baseline detecting step, or combining two or more (previously separate) detecting steps. Different types of detection steps may be included in a revised assay, that were either separate in the baseline assay, or that comprise adding an additional step or steps to the baseline assay; for example, a revised assay may include both kinetic measurements and end-point measurements to obtain more data than was obtained in a baseline assay that included only one of these measurements. Including kinetic measurements before the end timepoint of an end-point measurement does not add to the duration of the assay, yet may provide further information or more precise information useful to the assay.

FIG. 1 illustrates an embodiment of the methods disclosed herein, in which a step of a baseline assay is altered, and the results of the performance of the revised assay (including the alteration) are compared to the results of the performance of the baseline assay (not including the alteration in the step). In this figure, and all subsequent figures, arrows indicate the sequence of steps in the embodiments illustrated, with the step at the base end of the arrow preceding the step at the arrow-head end of the arrow. Rectangular and square shapes indicate steps to be performed. Diamond shapes indicate decision, or branch, points, the text within such diamonds indicating the criteria determining which of two or more possible subsequent steps is to be performed. As shown in FIG. 1, if the results of the performance of the revised assay are as good as, or better than, the results of the performance of the baseline assay, then the revised assay is considered improved. If the results of the results of the performance of the assay including the altered step are not as good as, or are worse than, the results of the performance of the baseline assay, then the revised assay is not considered improved.

Iterative Steps for Improving Assays

In embodiments of the methods to improve an assay disclosed herein, a baseline assay is selected for improvement; an aspect of the baseline assay is altered to provide a first revised assay, and the results of the first revised assay are compared to the results of the baseline assay. If the results of the first revised assay are similar to, are substantially the same as, or are better than, the results of the baseline assay, then the first revised assay may be considered an improved assay: e.g., and improved version of the baseline assay. In embodiments, the alteration of the baseline assay comprises an alteration that is considered to be an improvement; for example, the alteration may include a change that may reduce the duration of an assay step, or may reduce the number of steps required to perform the assay, or may reduce the cost of a step, or may reduce the number of reagents required for a step, or may alter the detection of results of the assay, or may improve the compatibility of the assay with other assays, or may improve the assay in other ways. For example, the alteration may include a change that may improve the sensitivity of the assay, or may improve the accuracy of the assay, or may improve the speed of the assay, or may improve the reliability of the assay, or may improve other aspects of the assay.

If the results of the first revised assay are not similar to, or not substantially the same as, or are worse than, the results of the baseline assay, then the first revised assay is not considered an improved assay. In this situation, a different alteration of the aspect of the baseline assay may be made in order to provide a further revised assay, and the results of such a further revised assay compared to the results of the baseline assay; or a different aspect of the baseline assay may be altered to provide a further revised assay, and the results of such a further revised assay compared to the results of the baseline assay. If the results of such a further revised assay are similar to, are substantially the same as, or are better than, the results of the baseline assay, then the further revised assay may be considered to be an improved assay. If the results of the further revised assay are not similar to, or not substantially the same as, or are worse than, the results of the baseline assay, then the further revised assay is not considered an improved assay. In this situation, additional alterations may be made to the altered aspect of the baseline assay, or additional aspects of the baseline assay may be altered, or both, in further applications of the methods to improve the baseline assay.

Accordingly, if the results of the first revised assay are an improvement as compared to the results of the baseline assay, the first revised assay may itself be used as a baseline assay in further iterations of methods for the improvement of an assay. That is, following an initial performance of a method to improve an assay, the initial baseline assay may be replaced, in subsequent iterations, by an improved assay identified by the initial performance of the method. If an initial performance of a method to improve an assay fails to provide improved results (as compared to the baseline assay results) then the method may be repeated; in this case, the same, unchanged baseline assay is again used for comparison. However, in this repetition, a different revision than was applied previously is applied to that baseline assay. In any case, if improved methods are identified, whether in the first or in subsequent iterations, then these improved methods may be used as the baseline assay for subsequent iterations of a method to improve an assay performed after their identification. In this way, subsequent iterations of these methods for assay improvement include and build upon the results of prior performances of these methods.

For example an iterative process of altering a baseline assay, where such alterations are with respect to the conditions and requirements of the baseline assay, may include some or all of the following:

- Defining the kinetics of the assay (e.g., whether to use kinetic assays, end-point assays, or both);
- Identifying the expected range of assay results that may be obtained from the assay when applied to samples obtained from a wide range of subjects;
- Identifying, and preferably demonstrating, a reasonable assay response across this range of expected assay results:
- Selecting an appropriate and suitable calibrator (to serve as a control), with a preference for simple and readily available calibration reagents;
- Selecting a suitable sample type (e.g., untreated, or filtered, or pre-treated in other ways) with a preference for no or minimal pre-treatment of the sample;
- Selecting a suitable sample volume for use in the assay, with a preference for small volumes (e.g., <1 uL of plasma or other liquid sample);
- Selecting a suitable diluent compatible with the sample, the analyte, and the reagents used in the assay;
- Selecting a suitable target sample dilution factor for at least a first step in the assay, in order that the assay results will be expected to all fall within a detectable range (as expected from the possible range of samples from a wide range of subjects), thereby providing an altered sample dilution if required;
- Selecting a suitable second and subsequent target sample dilution factor(s) for one or more subsequent steps in the assay, if the assay may require a second or subsequent dilution(s) in order that the assay results will be expected to all fall within a detectable range, thereby providing a further altered sample dilution if required;
- Selecting a suitable assay temperature, for one, some, or all steps;
- Selecting a suitable active ingredient concentration for a first ingredient of a reagent to be used with samples diluted by the selected sample dilution factor, thereby providing an altered reagent composition if required;
- Repeating the selection of a suitable active ingredient concentration for a second and other ingredients of a reagent or reagents to be used with samples diluted by the selected diluent;
- Where necessary, adapting all active ingredient concentrations in concert with each other so that all ingredients may be used at the dilution factor (or factors if the sample may be diluted a first time and a second or more times during the performance of the assay) used in the assay;
- Combining two or more steps where possible (e.g., where the baseline assay includes two steps, each of which comprises addition of a reagent, and where the two reagents are mutually compatible, the two steps may be performed together as one step);
- Deleting any step which may be omitted without significantly compromising the integrity of the results of the assay;
- Adding any additional steps as may be required in order to provide suitable assay results;
- Selecting suitable step durations, and a suitable assay duration (the total time taken to perform all assay steps) compatible with the assay temperature, sample volume, sample dilution, and reagent concentrations obtained from the preceding steps, with a preference for shorter duration steps, and a shorter assay duration, whenever possible; and
- Selecting or altering other assay parameters so as to be suitable for use in the revised assay based on the range of assay results expected from samples obtained from a wide range of subjects.

It will be understood that, in the practice of the iterative methods disclosed herein that not all of the steps discussed above need be applied in every instance, but that instead, some baseline assays may be improved by application of only some of the above-mentioned iterative steps for improving assays, and that one baseline assay may require a different subset, or combination, of the above-mentioned steps than does another baseline assay. In embodiments, some baseline assays may be improved by application of all of the above-mentioned iterative steps for improving assays, and some baseline assays may be improved only by application of all of the above-mentioned iterative steps for improving assays. However, in embodiments, some baseline assays may be improved by application fewer than all of the above-mentioned iterative steps for improving assays.

Figure 2:
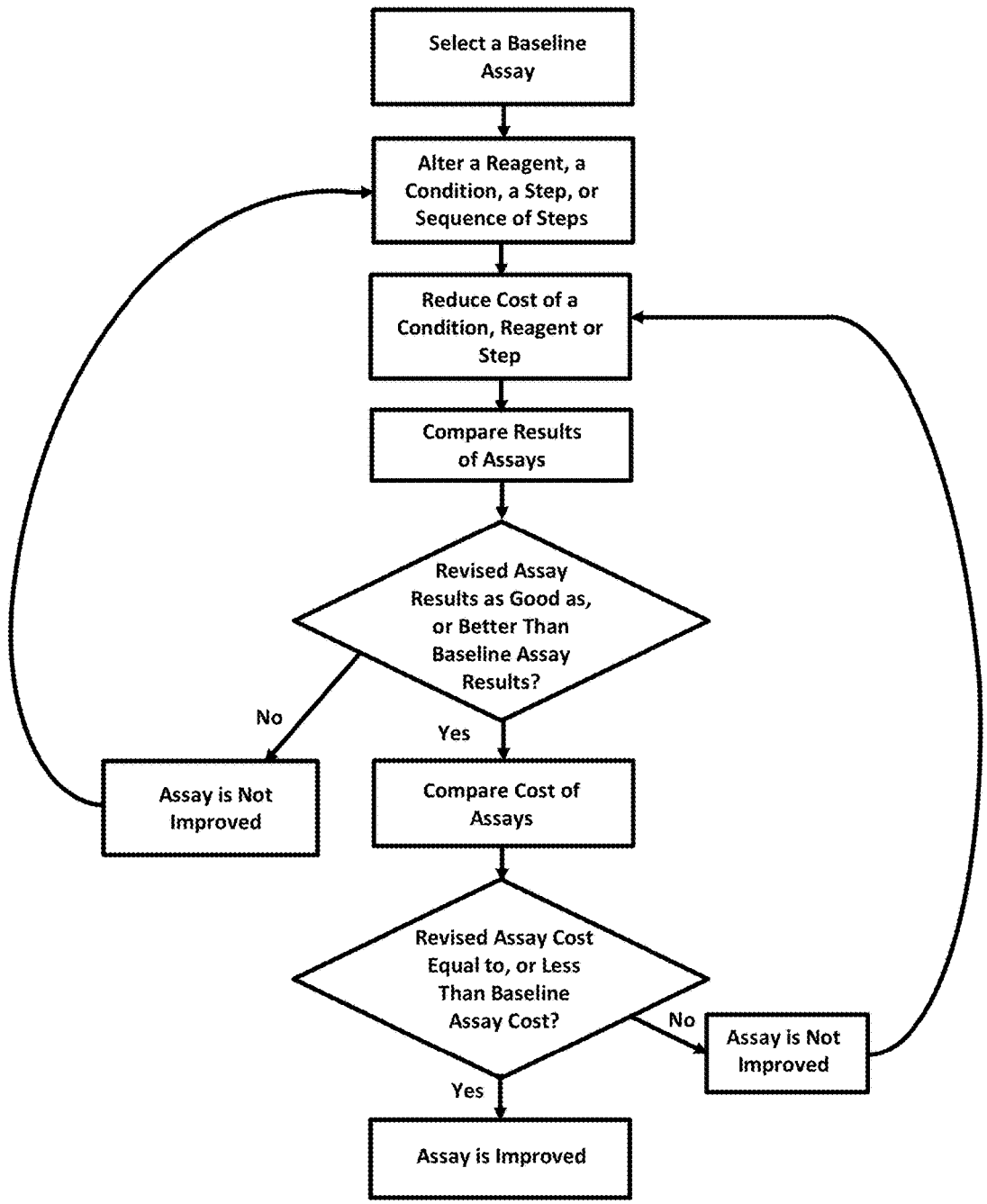
FIG. 2 illustrates an embodiment of the methods disclosed herein, in which a step of a baseline assay is altered thereby providing a revised assay, and the results of the performance of the revised assay are compared to the results of the performance of the baseline assay. An alteration of a baseline assay may include any change to the assay, such as a change to a step (e.g., a change to a reagent used in the step, or the timing or conditions of the step), or the sequence of steps, including combining or eliminating steps.

FIG. 2 illustrates an embodiment of the methods disclosed herein, in which a step of a baseline assay is altered, and the results of the performance of the revised assay (including the alteration) are compared to the results of the performance of the baseline assay (not including the alteration in the step). Alterations of a step, or steps, of a baseline assay may include alteration of a reagent used in a step, or of the order of performing steps, or any alteration which may affect a condition or aspect of an assay. As discussed herein, such alterations include alteration of a pre-treatment step, or a dilution step, or an aliquotting step, or a separating step, or a transporting step, or a mixing step, or an incubating step, or a reacting step, or a labeling step, or a detecting step, or any other step or combination of steps. A further step of reducing the cost of a condition, reagent, or assay step is also included in the method illustrated in this figure; in embodiments, the alteration of a reagent, condition, step, or sequence of steps may include the reduction of cost of a condition, reagent, or step. The results of the revised assay is compared to the results of the baseline assay, and the cost of performing the revised assay is compared to the cost of performing the baseline assay, in order to determine whether or not such alterations lead to improving the assay or not. It will be understood that these considerations are applicable to the methods illustrated in any and all of the figures herein, and to any and all embodiments of the methods disclosed in the application.

Embodiments of the methods to improve an assay disclosed herein include iterative methods for improving an assay. Iterative methods for improving an assay include methods in which a baseline assay is selected for improvement; an aspect of the baseline assay is altered to provide a first revised assay; the results of the first revised assay are compared to the results of the baseline assay; if the results of the first revised assay are similar to, substantially the same as, or better than, the results of the baseline assay, then the first revised assay may be termed an improved assay. Accordingly, a method for improving an assay may be used to provide an improved assay.

For example, in an iterative method comprising a first iteration and a second iteration, the method may include a first iteration of the method, where the first iteration comprises selecting a baseline assay, which may be termed a first baseline assay; altering an aspect of the first baseline assay to provide a first revised assay; comparing the results of the first revised assay to the results of the first baseline assay; and, if the results of the first revised assay are similar to, substantially the same as, or better than, the results of the first baseline assay, then the first revised assay may be termed the second baseline assay, and is selected as a baseline assay for a second iteration of the iterative method. The second iteration comprises altering an aspect of the second baseline assay to provide a second revised assay; comparing the results of the second revised assay to the results of the second baseline assay; and, if the results of the second revised assay are similar to, substantially the same as, or better than, the results of the first baseline assay, then the second revised assay is termed an improved assay. In embodiments, the results of the second revised assay may be similar to, substantially the same as, or better than, the results of the second baseline assay. Accordingly, an iterative method for improving an assay may comprise a first and a second iteration, and may be used to identify an improved assay.

Figure 3:
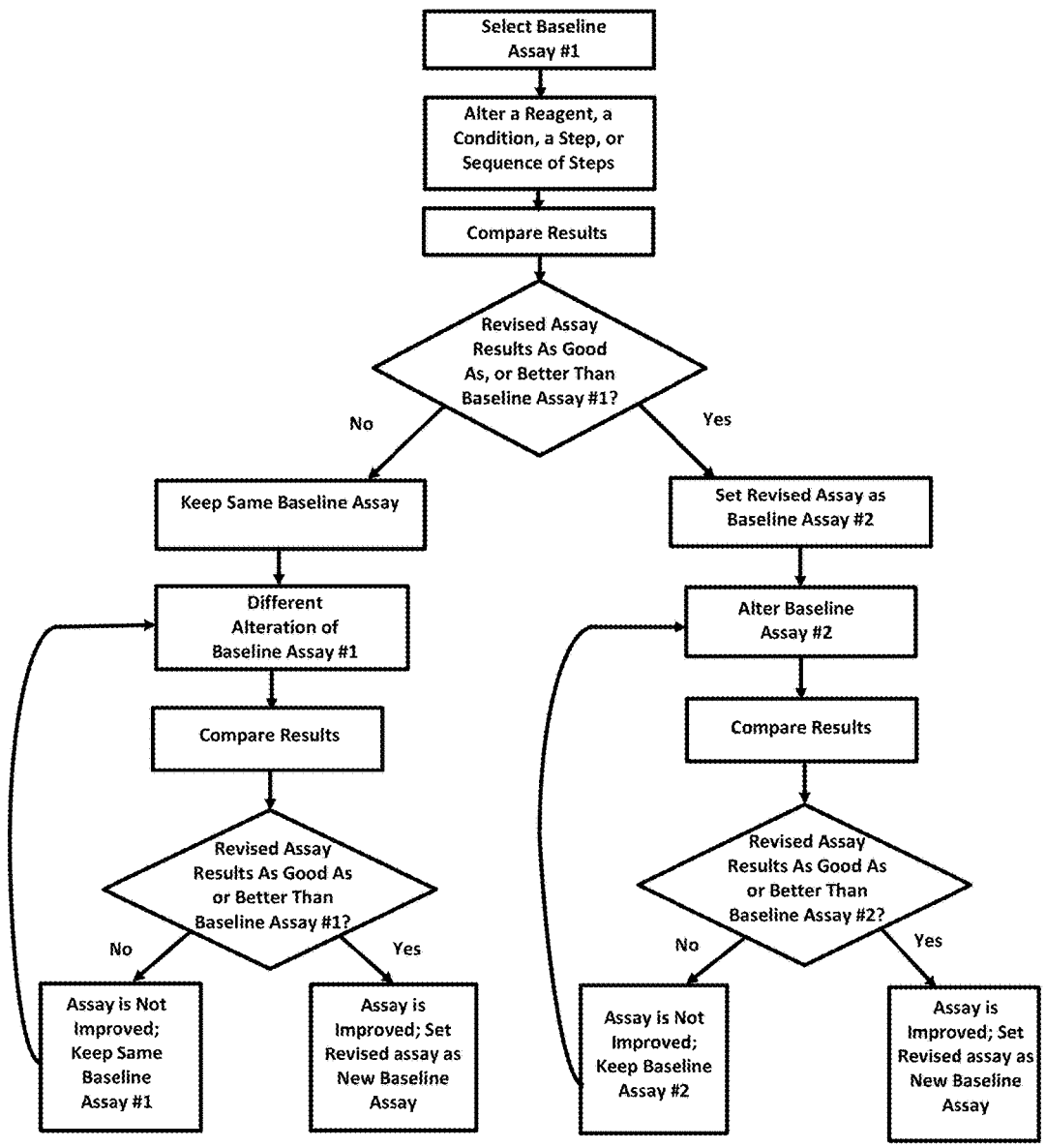
FIG. 3 illustrates an embodiment in which a step of a first baseline assay is altered, and the results of the performance of the revised assay are compared to the results of the performance of baseline assay #1. If the results of the results of the revised assay are as good as, or better than those of baseline assay #1, then the revised assay may be set as a baseline assay #2. The process may be repeated. If these subsequent results are as good as, or better than, the results of baseline assay #1, then the further revised assay may be considered improved, or may be used as a new baseline assay in further iterations of the methods.

FIG. 3 illustrates an embodiment of the methods disclosed herein, in which a step of a first baseline assay is altered, and the results of the performance of the assay (including the alteration) are compared to the results of the performance of the first baseline assay (not including the alteration in the step). If the results of the results of the performance of the revised assay (including the altered step) are as good as, or better than the results of the performance of the first baseline assay (baseline assay #1), then the revised assay is used as a second baseline assay (baseline assay #2), and the process is repeated. The repetition of the process comprises altering a step of baseline assay #2 to provide a second revised assay, performing the second revised assay, and comparing those results with the results of baseline #1. That comparison is used to determine whether or not the second revised assay provides results that are as good as, or better than, the results of baseline assay #1. If the second revised assay provides results that are as good as, or better than the results of baseline assay #1, then the second revised assay may be considered improved, or may be used as a new baseline assay in further repetitions of the methods.

In embodiments of the methods illustrated in FIG. 3, the repetition of the process comprises altering a step of baseline assay #2 to provide a second revised assay, performing the second revised assay, and comparing those results with the results of baseline #2 to determine whether or not the second revised assay provides results that are as good as, or better than, the results of baseline assay #2. Alternatively, as illustrated in the lower left in FIG. 2, where the results of the first revised assay are not as good as the results of baseline assay #1, then a further alteration in baseline assay #1 is provided, and is performed, and the results of that further revised assay are compared with the results of baseline assay #1. If the results of that further revised assay are as good as, or better than the results of baseline assay #1, then the further revised assay may be considered improved, or may be used as a new baseline assay in further iterations of the methods.

Thus, in embodiments, if the results of the first revised assay are similar to, substantially the same as, or better than, the results of the baseline assay, then the first revised assay may be selected as a baseline assay for a subsequent improvement step in the practice of the iterative method. In the following discussion of iterative methods for improving an assay, the terms "first revised assay", "second revised assay", "third revised assay", "fourth revised assay", and so on are to be taken to include a "further revised assay" as discussed in the preceding paragraph.

Figure 4:
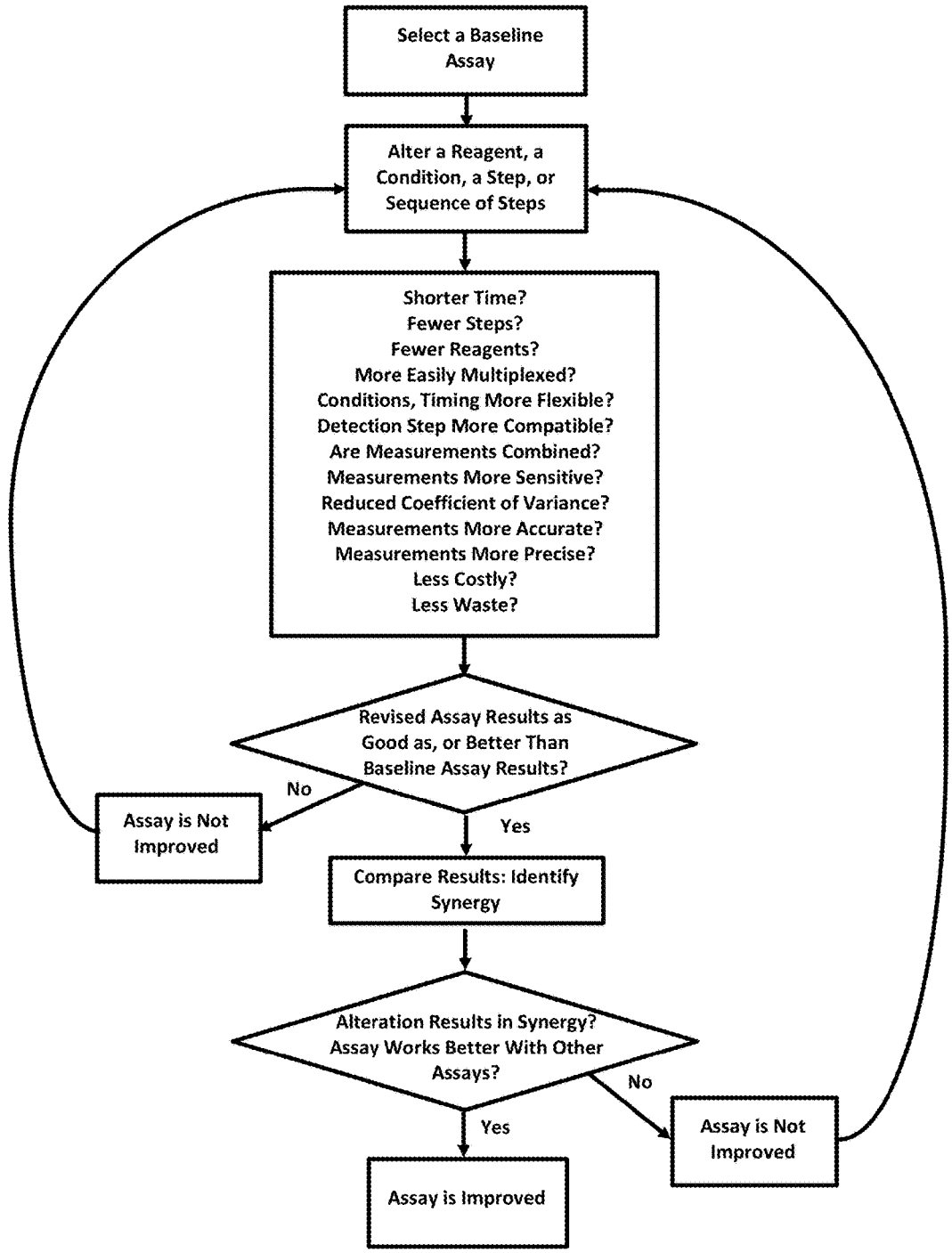
FIG. 4 illustrates an embodiment of methods for improving assays, in which an assay is altered as compared to a baseline assay. The results of performing the revised assay are compared to the results of performing the baseline assay, and are reviewed in order to identify any synergistic effects of these assay alterations.

FIG. 4 illustrates an embodiment of methods for improving assays, in which a reagent, a condition, a step, or the sequence of steps is altered as compared to a baseline assay. The results of performing the revised assay are compared to the results of performing the baseline assay; in addition, whether or not these alterations lead to synergistic effects on the results or ease of performance of the assay is determined. For example, the elimination of a step (by not performing the step, or by combining its performance with that of another step), or the increase in the temperature of a reaction step, or the shortening of the duration of an incubation step, may additionally provide the synergistic effect of shortening the total duration of the assay. These methods for improving an assay include identifying assay alterations which lead to synergistic effects on the performance and results of the assay. Thus, methods for improving an assay include providing assay alterations which lead to synergistic effects which improve the performance and results of the assay.

As shown in FIG. 4, examples of criteria which may be used to determine whether or not results of a revised assay are as good as, or better than, a baseline assay include determining whether or not the revised assay may be performed in a shorter time than the baseline assay; whether or not the revised assay may be performed with fewer steps than the baseline assay; whether or not the revised assay may be performed with fewer reagents than the baseline assay; whether or not the revised assay is more easily multiplexed with other assays than the baseline assay; whether or not the conditions required, or the timing required, for performing the revised assay are more flexible than those of the baseline assay; whether or not the detection steps used by the revised assay are more compatible with other assays than are the detection steps of the baseline assay; whether or not measurements are combined in the performance of the revised assay that may not be (or are not as readily) combined in the performance of the baseline assay; whether or not measurements for the revised assay may be combined with those of other assays, which cannot be (or may not as readily be) combined with the baseline assay; whether or not the measurements used in the revised assay are more sensitive than those used in the baseline assay; whether or not the revised assay provides a reduced coefficient of variance as compared with the coefficient of variance provided by the baseline assay; whether or not the revised assay measurements are more precise than the measurements of the baseline assay; whether or not the revised assay measurements are more accurate than the measurements of the baseline assay; whether or not the performance of revised assay is less costly than the performance of the baseline assay; and whether or not the performance of the revised assay produces less waste than does the performance of the baseline assay. These, and other questions and criteria, may be used to identify revised assays which are improved assays as compared to a baseline assay.

Accordingly, methods for improving assays as disclosed herein provide revised assays which are improvements upon baseline assays. Such improvements include, for example, revised assays which require smaller volumes of sample for the performance of the assay than do baseline assays. Such improvements include, for example, revised assays which are simpler to perform than are baseline assays. Such improvements include, for example, revised assays which require lesser, or no, pretreatment of a sample than baseline assays. Such improvements include, for example, revised assays which require shorter amounts of time to perform than baseline assays (e.g., may be performed more rapidly than baseline assays). Such improvements include, for example, revised assays which require fewer reagents, or smaller volume of reagents, than baseline assays. Such improvements include, for example, revised assays which require fewer steps to perform than baseline assays. Such improvements include, for example, revised assays which are less costly to perform than baseline assays.

Figure 5:
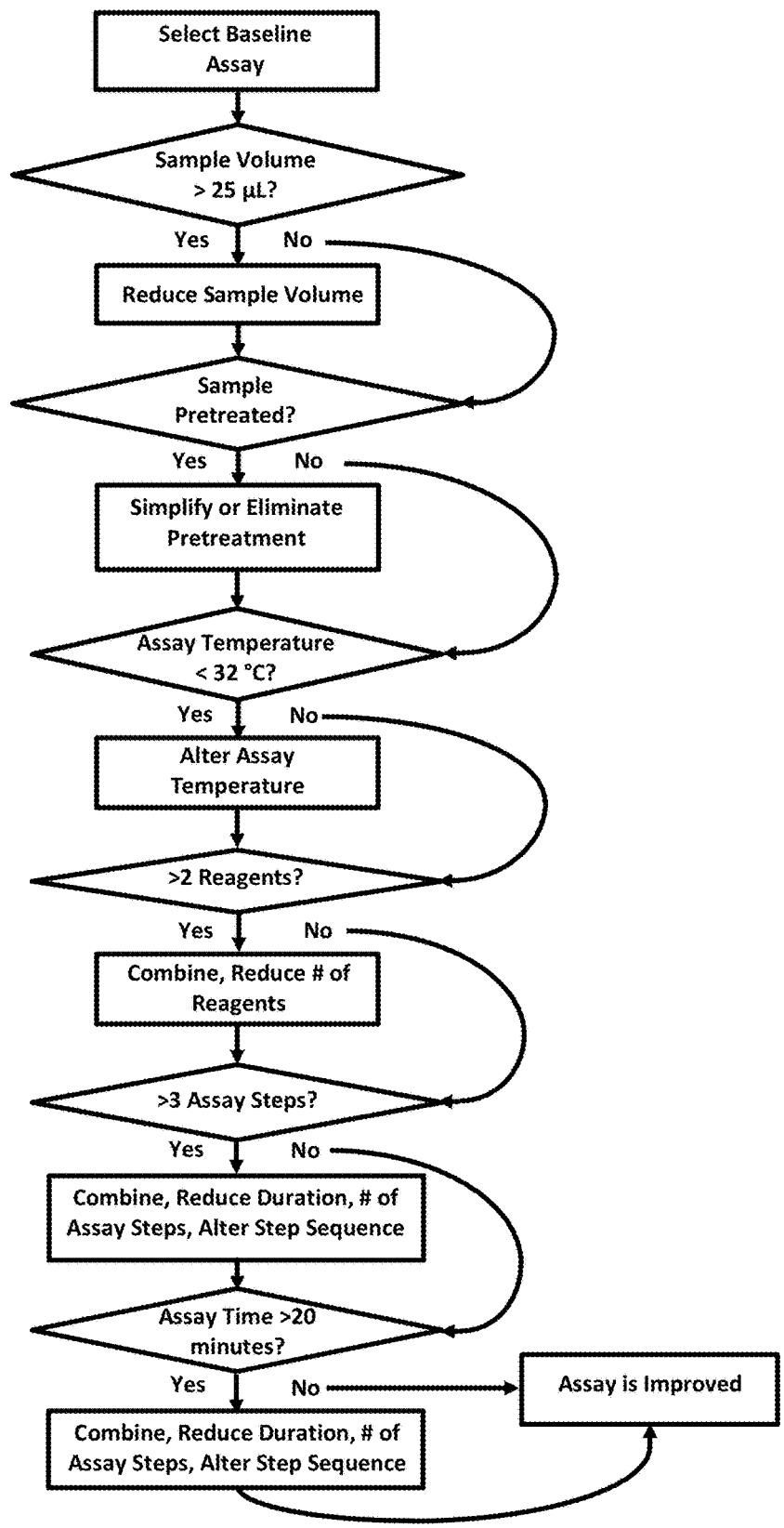
FIG. 5 illustrates an embodiment of the methods disclosed herein, in which a baseline assay is selected for improvement, and a series of steps are taken in which several aspects of the baseline assay are altered. Several exemplary modifications are shown.

FIG. 5 illustrates an embodiment of the methods disclosed herein, in which a baseline assay is selected for improvement, and a series of steps are taken in which several aspects of the baseline assay are altered. As shown, the sample volume may be reduced; a sample pretreatment step may be simplified or eliminated; the temperature of one or more steps of the assay may be altered (e.g., when the baseline assay temperature is less than 32° C. as shown in the figure, or when the baseline assay temperature is less than 30° C., or other threshold value); the number of reagents used in the assay may be reduced; the number of steps in the assay may be reduced; and the total assay time may be reduced as a result of alterations in the assay, as illustrated in this example of methods for improving an assay.

In embodiments, the sample volume collected from a subject may be reduced, or the volume of an aliquot of sample used in the assay may be reduced. In embodiments, the sample may be diluted, to provide a larger volume of working fluid while requiring only a small amount of sample. For example, reducing the volume of sample required for an assay, e.g., by dilution, may provide the advantage of allowing multiple assays to be performed with a single collection of sample from a subject, without undue discomfort or anxiety on the part of the subject. Performing multiple assays on a single sample, or on portions of a single sample, not only simplifies the collection of the sample from a subject, but reduces possible variability in assay results, and improves the ability to compare results from different assays with confidence that the assays are all based on the same sample.

Providing a single dilution prior to further steps in an assay, and prior to parceling out aliquots to multiple assays, provides a standard, initial sample for subsequent use in an automated device or system. Dilution of a sample may, in some instances, lead to a reduction in the amplitude of an assay signal obtained from the (diluted) sample, possibly leading to less accurate measurements or an increase in the variability (e.g., coefficient of variance) of measurements; however, where this may be an issue, compensatory steps may be taken. For example, reagents, physical treatments, and other assay and detection steps may be altered to compensate. For example, more sensitive detectors may be used; the sample or aliquot may be concentrated or centrifuged; reactant concentrations in a reagent may be increased, e.g., to increase signal intensity, or to reduce reagent volume (reducing further dilution of the sample); assay temperature may be altered to increase signal or speed a reaction; the number of reagents may be reduced, thereby reducing possible compounding of possible volume or other errors; more precise measurements of sample or aliquot volume may be made; and other adjustments may be made). In this way, more efficient use of the sample is made, with less waste. In addition, the number of assay steps and assay duration may be reduced, providing more rapid analysis and more flexibility for performing multiple assays from a single sample collection, and on a single device or system.

In embodiments, a sample pretreatment step may be simplified or eliminated; for example, where a baseline assay includes multiple sample pretreatment steps, a revised assay may combine some or all these pretreatment steps, e.g., into a single pretreatment step where all pretreatment steps may be combined. In embodiments where a first reagent is added in a pretreatment step, and that first reagent is compatible with the other reagents used in a subsequent step, and the timing is acceptable, the pretreatment step may be eliminated by addition of that first reagent in a subsequent step. In embodiments, where a pretreatment step requires an incubation period, increasing the concentration of a reagent may allow shortening of the duration of the pretreatment step.

In embodiments, the concentration of a single reactant in a reagent, or of multiple reactants in a reagent, may be increased in order to speed a reaction, or drive a reaction to completion in a shorter time as compared to the time required with a lower reactant concentration, or more fully complete a reaction, or for other reasons which improve an assay. Thus, increasing the concentration of a reactant in a reagent may reduce the time required for an assay step. In embodiments, increasing the concentration of a dye may reduce the time required to reach acceptable levels of staining. In embodiments, increasing the concentration of a quencher may reduce the time required to stop a reaction, or to reduce fluorescence, as compared to the time required with a lower quencher concentration.

In embodiments, altering the concentration of ingredients other than reactants in a reagent may speed a reaction, or improve the efficiency, or improve the reliability of an assay. For example, altering the salt concentrations used in a nucleic acid assay may affect the melting temperature of nucleic acid hybridization, so that changing the salt concentration may improve such an assay. Other ingredients, including surfactants, osmoticants, solvents, and other ingredients may affect the rate, completion, and specificity of an assay, and alterations in the amounts of such ingredients may improve an assay. Selecting a different ingredient to use, or a different mixture of ingredients, out of a selection of suitable ingredients, may improve an assay.

In embodiments, an alteration of an assay temperature will raise the temperature if the temperature is, e.g., room temperature, or other temperature lower than about 30° C., or lower than about 32° C. It will be understood that, in embodiments of the methods disclosed herein, the temperature of one or more steps of the assay may be altered when the temperature is less than about 34° C., or when the temperature is less than about 35° C., or when the temperature is less than about 36° C., or when the temperature is less than about 37° C., or other temperature. In embodiments of the methods disclosed herein, an alteration in a step may include setting the temperature of the step to be about 31° C., or about 32° C., or about 33° C., or about 34° C., or about 35° C., or about 36° C., or about 37° C., or about 38° C., or about 39° C., or about 40° C., or other temperature. In preferred embodiments, an alteration of a temperature will raise the temperature to become nearer to about 37° C. Increasing the temperature of a step, or of multiple steps, will typically also increase the rate of reactions occurring in that step, and so will typically shorten the duration of a step, and of an assay, providing an improvement as compared to the baseline assay.

In embodiments, the number of reagents used in the assay may be reduced by including the ingredients of a first reagent with those of a second reagent to provide a single reagent where two reagents were used in the baseline assay. Reducing the number of reagents reduces the complexity of an assay, and typically will increase the reliability and repeatability of the assay as compared to a baseline assay, providing an improvement as compared to the baseline assay.

In embodiments, the number of steps may be reduced where a baseline assay includes steps which may be combined in a revised assay. For example where multiple reagents are each added, with an addition step for each reagent, and where two or more reagents may be combined into one reagent, or may be added in the same addition step, the number of assay steps may be reduced. Reducing the number of steps in an assay reduces the complexity of the assay, and typically shortens the total time required to perform an assay. Reducing complexity typically increases the reliability and repeatability of the assay, providing an improvement as compared to the baseline assay. Shortening the time required to perform an assay also provides an improvement over the baseline assay.

Accordingly, the methods disclosed in FIG. 5 provide multiple strategies for improving assays. Some or all of these strategies may be applied in improving a baseline assay. It will be understood that other strategies may be suitable for some assays, and may also be applied in methods of improving assays as disclosed herein.

Figure 6:
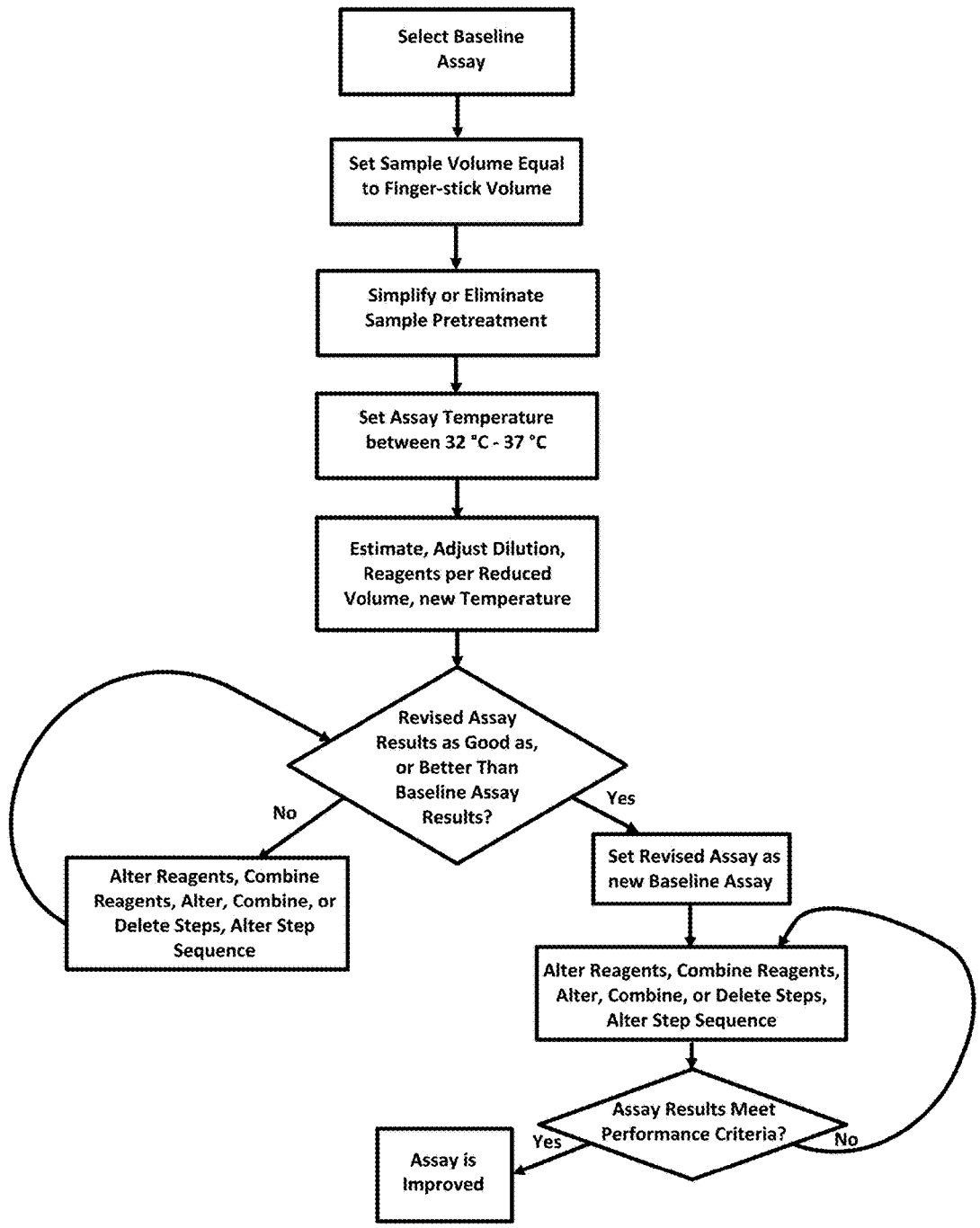
FIG. 6 illustrates further embodiments of methods for improving an assay which requires a biological sample. For example, the assay illustrated in this figure may be a general chemistry assay. Several exemplary modifications are shown (e.g., the volume of the biological sample is reduced to the volume of a fingerstick, e.g., a few drops of about 40 µL each, for a total volume of about 100 µL to about 150 µL). The results of the performance of the revised assay are compared to the results of the performance of the baseline assay.

FIG. 6 illustrates embodiments of methods for improving an assay, in which a baseline assay is selected for improvement or improvement, where the baseline assay requires a biological sample; the baseline assay is altered so that the volume of the biological sample is reduced to the volume of a finger-stick (e.g., the volume of a drop, or of a few drops, of blood resulting from a small puncture of the skin of a subject); the baseline assay is altered so as to eliminate, or to reduce any pretreatment step or steps; the baseline assay is altered so that the assay temperature is set to between about 32° C. to about 37° C.; the dilution of the sample, if any, and the volumes and concentrations of reagents used in the assay are adjusted in view of the altered sample volume and revised assay temperature; and other alterations. In other embodiments, another temperature range may be selected; for example, the assay temperature may be set to between about 30° C. and about 40° C.; or to between about 32° C. and about 38° C.; or to between about 34° C. and about 37° C.; or other temperatures. Other alterations may include, for example, altering the dilution of the sample, altering a reagent (e.g., ingredients, ingredient concentrations, pH, temperature, osmolarity, or other reagent characteristic), combining reagents, combining steps, altering the sequence of steps, and other alterations. The results of the performance of the revised assay are compared to the results of the performance of the baseline assay.

Figure 7:
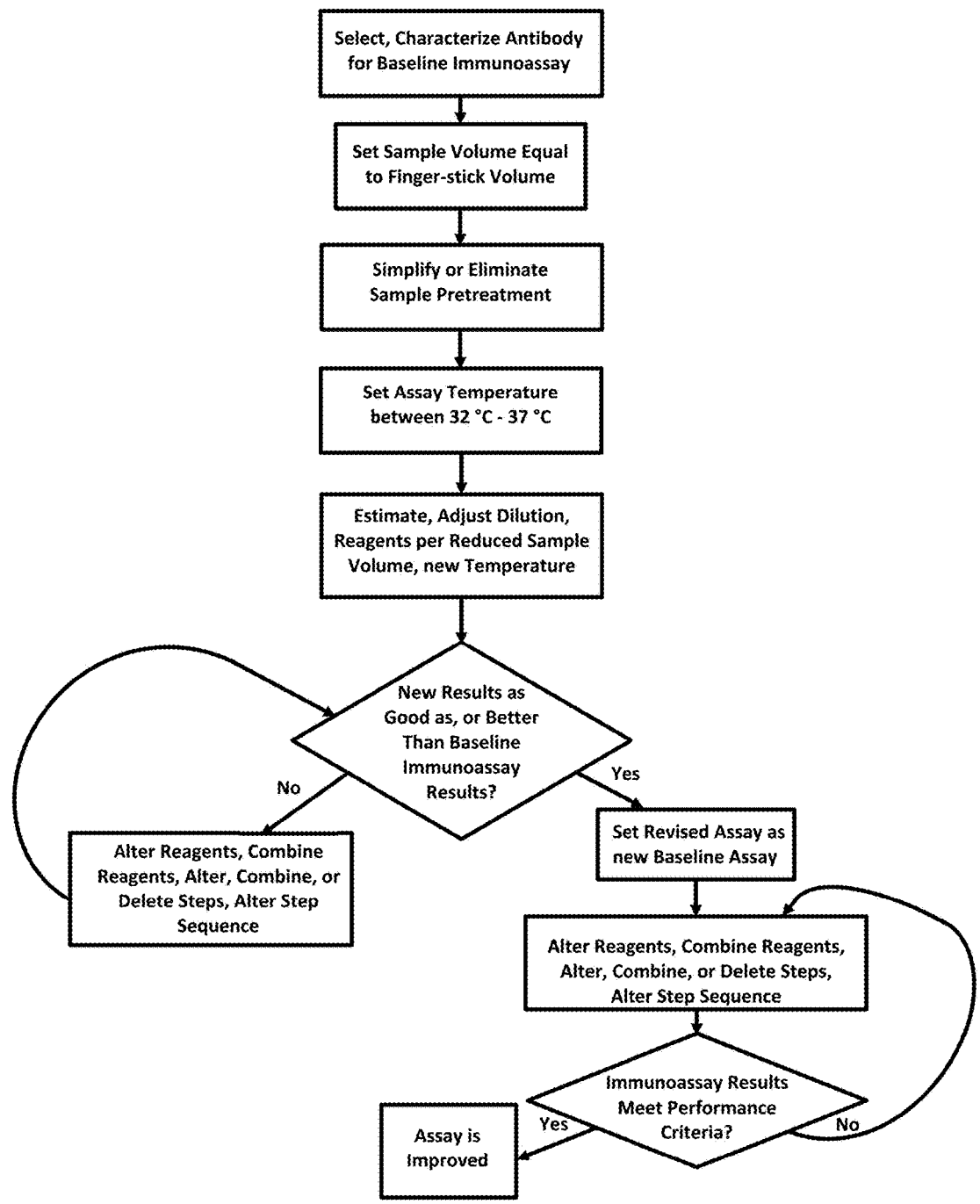
FIG. 7 illustrates embodiments of methods for improving an immunoassay. The baseline immunoassay may be altered by any or all of the exemplary assay modifications shown in the figure. As shown, proper selection of an antibody used in an immunoassay may improve the immunoassay. The results of the performance of the altered immunoassay are compared to the results of the performance of the baseline immunoassay.

FIG. 7 illustrates embodiments of methods for improving an immunoassay, in which a baseline immunoassay is selected for improvement or improvement, where the baseline immunoassay requires a biological sample; the baseline immunoassay is altered so that the volume of the biological sample is reduced to the volume of a fingerstick (e.g., the volume of a drop of blood resulting from a small puncture of the skin of a subject); the baseline immunoassay is altered so as to eliminate, or to reduce any pretreatment step or steps; the baseline immunoassay is altered so that the assay temperature is set to between about 32° C. to about 37° C.; the dilution of the sample, if any, and the volumes and concentrations of reagents used in the immunoassay are adjusted in view of the altered sample volume and revised assay temperature; and other alterations. In embodiments, another temperature range may be selected, e.g., between about 30° C. and about 40° C.; or to between about 32° C. and about 38° C.; or to between about 34° C. and about 37° C.; or other temperatures. Other alterations may include, for example, altering the dilution of the sample, altering a reagent (e.g., ingredients, ingredient concentrations, pH, temperature, osmolarity, or other reagent characteristic), combining reagents, combining steps, altering the sequence of steps, and other alterations. The results of the performance of the altered immunoassay are compared to the results of the performance of the baseline immunoassay.

Figure 8:
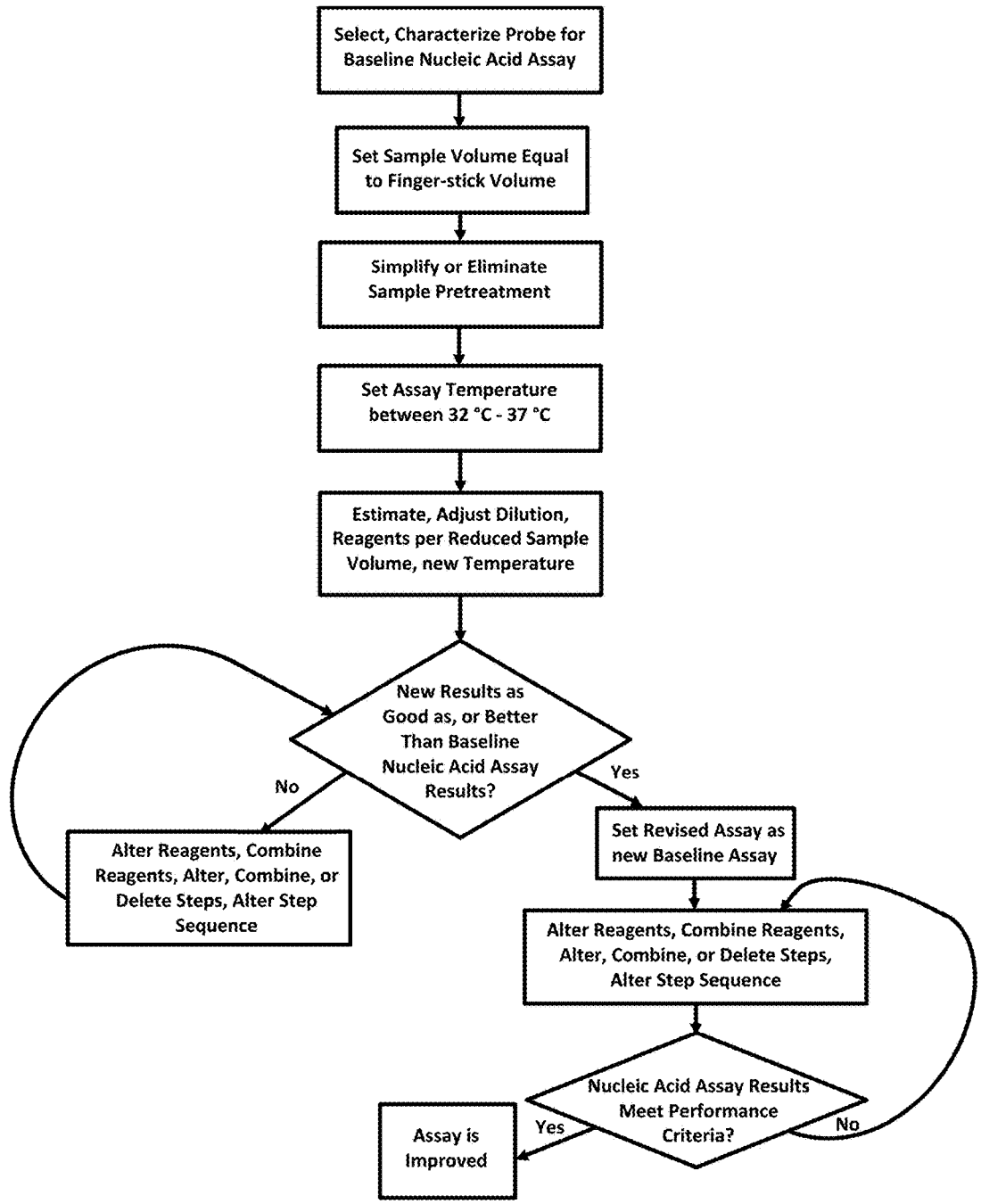
FIG. 8 illustrates embodiments of methods for improving a nucleic acid assay. The baseline nucleic acid assay may be altered by any or all of the exemplary assay modifications shown in the figure. As shown, proper selection of a nucleic acid probe used in a nucleic acid assay may improve the assay. The results of the performance of the altered nucleic acid assay are compared to the results of the performance of the baseline nucleic acid assay.

FIG. 8 illustrates embodiments of methods for improving a nucleic acid assay, in which a baseline nucleic acid assay is selected for improvement or improvement, where the baseline nucleic acid assay requires a biological sample; the baseline nucleic acid assay is altered so that the volume of the biological sample is reduced to the volume of a finger-stick (e.g., the volume of a drop of blood resulting from a small puncture of the skin of a subject); the baseline nucleic acid assay is altered so as to eliminate, or to reduce any pretreatment step or steps; the baseline nucleic acid assay is altered so that the assay temperature is set to between about 32° C. to about 37° C.; the dilution of the sample, if any, and the volumes and concentrations of reagents used in the nucleic acid assay are adjusted in view of the altered sample volume and revised assay temperature; and other alterations. In embodiments, another temperature range may be selected, e.g., between about 30° C. and about 40° C.; or to between about 32° C. and about 38° C.; or to between about 34° C. and about 37° C.; or other temperatures. Other alterations may include, for example, altering the dilution of the sample, altering a reagent (e.g., ingredients, ingredient concentrations, pH, temperature, osmolarity, or other reagent characteristic), combining reagents, combining steps, altering the sequence of steps, and other alterations. The results of the performance of the altered nucleic acid assay are compared to the results of the performance of the baseline nucleic acid assay.

Figure 9:
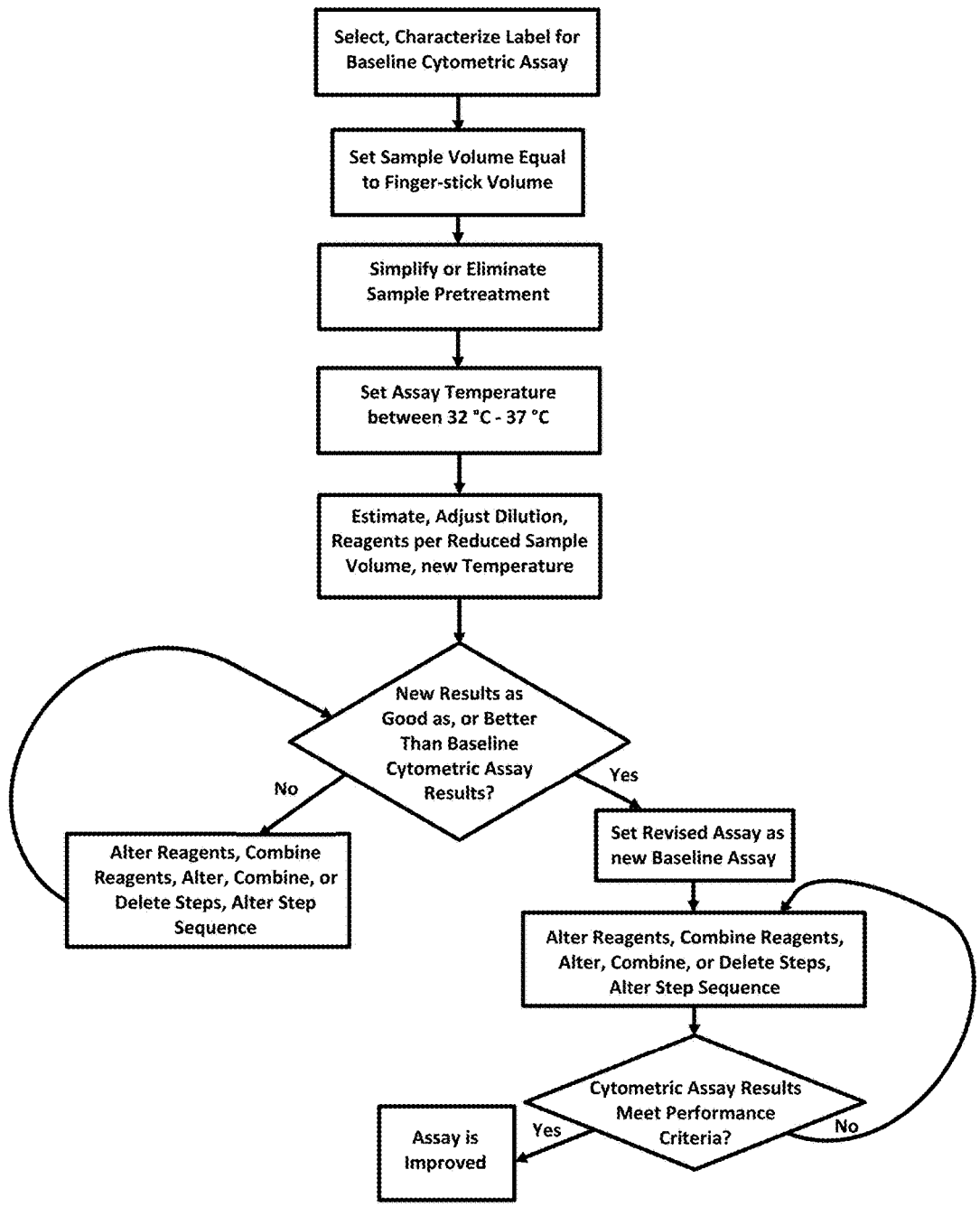
FIG. 9 illustrates embodiments of methods for improving a cytometric assay. The baseline cytometric assay may be altered by any or all of the exemplary assay modifications shown in the figure. As shown, proper selection of a label (e.g., a dye) used in a cytometric assay may improve the assay. The results of the performance of the altered cytometric assay are compared to the results of the performance of the baseline cytometric assay.

FIG. 9 illustrates embodiments of methods for improving a cytometric assay, in which a baseline cytometric assay is selected for improvement or improvement, where the baseline cytometric assay requires a biological sample; the baseline cytometric assay is altered so that the volume of the biological sample is reduced to the volume of a fingerstick (e.g., the volume of a drop of blood resulting from a small puncture of the skin of a subject); the baseline cytometric assay is altered so as to eliminate, or to reduce any pretreatment step or steps; the baseline cytometric assay is altered so that the assay temperature is set to between about 32° C. to about 37° C.; the dilution of the sample, if any, and the volumes and concentrations of reagents used in the cytometric assay are adjusted in view of the altered sample volume and revised assay temperature; and other alterations. In embodiments, another temperature range may be selected, e.g., between about 30° C. and about 40° C.; or to between about 32° C. and about 38° C.; or to between about 34° C. and about 37° C.; or other temperatures. Other alterations may include, for example, altering the dilution of the sample, altering a reagent (e.g., ingredients, ingredient concentrations, pH, temperature, osmolarity, or other reagent characteristic), combining reagents, combining steps, altering the sequence of steps, and other alterations. The results of the performance of the altered cytometric assay are compared to the results of the performance of the baseline cytometric assay.

Further Iterative Methods

For example, in an iterative method comprising a first iteration, a second iteration, and a third iteration, the method may include a first iteration of the method, where the first iteration comprises selecting a baseline assay, which may be termed a first baseline assay; altering an aspect of the first baseline assay to provide a first revised assay; comparing the results of the first revised assay to the results of the first baseline assay; and, if the results of the first revised assay are similar to, substantially the same as, or better than, the results of the first baseline assay, then the first revised assay is termed the second baseline assay and is selected as a baseline assay for a second iteration of the iterative method. The second iteration comprises altering an aspect of the second baseline assay to provide a second revised assay; comparing the results of the second revised assay to the results of the second baseline assay; and, if the results of the second revised assay are similar to, substantially the same as, or better than, the results of the second baseline assay, then the second revised assay is termed a third baseline assay and is selected as a baseline assay for a third iteration of the iterative method. The third iteration comprises altering an aspect of the third baseline assay to provide a third revised assay; comparing the results of the third revised assay to the results of the third baseline assay; and, if the results of the third revised assay are similar to, substantially the same as, or better than, the results of the first baseline assay, then the third revised assay is termed an improved assay. In embodiments, the results of the third revised assay may be similar to, substantially the same as, or better than, the results of the second baseline assay or the third baseline assay. Accordingly, an iterative method for improving an assay may comprise a first, a second, and a third iteration, and may be used to identify an improved assay.

In embodiments, an iterative method for improving an assay may comprise selecting a first baseline assay and may include four iterations: a first iteration, a second iteration, a third iteration, and a fourth iteration. Similar to the methods disclosed above comprising two and three iterations, a method comprising four iterations includes the following: a first iteration, in which the results of the first baseline assay are compared to the results of a first revised assay; a second iteration, in which the results of the second baseline assay are compared to the results of a second revised assay; a third iteration, in which the results of the third baseline assay are compared to the results of a third revised assay; and a fourth iteration, in which the results of the fourth baseline assay are compared to the results of a fourth revised assay. If the results of the fourth revised assay are similar to, substantially the same as, or better than, the results of the first baseline assay, then the fourth revised assay is termed an improved assay. In embodiments, the results of the fourth revised assay may be similar to, substantially the same as, or better than, the results of the second baseline assay, the third baseline assay, or the fourth baseline assay.

In further embodiments, an iterative method for improving an assay may comprise selecting a first baseline assay and may include multiple iterations, where the number of iterations may be, e.g., five iterations, or more than five iterations. For example, iterative methods for improving an assay comprising multiple iterations may include selecting a first baseline assay and the following: a first iteration, in which the results of the first baseline assay are compared to the results of a first revised assay; a second iteration, in which the results of the second baseline assay are compared to the results of a second revised assay; a third iteration, in which the results of the third baseline assay are compared to the results of a third revised assay; a fourth iteration, in which the results of the fourth baseline assay are compared to the results of a fourth revised assay; a fifth iteration, in which the results of the fifth baseline assay are compared to the results of a fifth revised assay; and, if there are more than five iterations, and a sixth iteration and optionally subsequent iterations, in which the results of the fifth baseline assay are compared to the results of a fifth revised assay, and optionally in which the results of a subsequent baseline assay or assays are compared to the results of a subsequent revised assay or assays. In iterative assays comprising a fifth or subsequent assay(s), the highest number iteration is termed the final iteration, the highest number baseline assay is termed the final baseline assay, and the highest number revised assay is termed the final revised assay. If the results of the final revised assay are similar to, substantially the same as, or better than, the results of the first baseline assay, then the final revised assay is termed an improved assay. In embodiments, the results of the final revised assay may be similar to, substantially the same as, or better than, the results of the second baseline assay, the third baseline assay, the fourth baseline assay, the fifth baseline assay, or any subsequent baseline assay.

Further Embodiments of Improvement Methods

Methods of improving assays include altering (e.g., improving) a step or steps of a baseline assay in order to alter (e.g., improve) the assay as a whole while providing good quality assay results. Such improvement may include altering (e.g., improving) the reagent configuration of a baseline assay; altering (e.g., improving) the protocol of a baseline assay; altering (e.g., improving) the detection method of a baseline assay; altering (e.g., improving) the timing of steps of, or the total time required to perform, a baseline assay; altering (e.g., reducing) the number of steps required to perform a baseline assay; altering (e.g., reducing) the cost required to perform a baseline assay; altering (e.g., reducing) the variability in results obtained from the performance of a baseline assay; altering (e.g., increasing) the accuracy of a baseline assay; altering (e.g., increasing) the precision of a baseline assay; and other alterations and adaptations.

Some goals of such improvements include shortening the time required to perform an assay; reducing the amount of sample required to perform the assay; reducing the complexity of the assay; reducing the cost of the assay; enhancing the ease of co-ordinating the performance of the assay with other assays performed on the same sample or with the same equipment; insuring that the assay uses detection methods compatible with other assays to be performed on the sample or with the same equipment; and other goals.

A further goal of such improvements is to demonstrate a reasonable response to the analyte over a wide range of clinical parameters. Careful choice of the sample and calibrator type may aid in achieving such a goal. Careful choices in selecting a target sample dilution factor; or in selecting concentrations of active ingredients in a reagent or reagents used in the assays; or of a step duration, or a total duration for the performance of the assay; or in selecting values or ranges for other parameters may aid in achieving such a goal.

In the course of improving an assay it may be found that altering the assay in one way affects or necessitates other alterations. For example, shortening the duration or, or eliminating, a step would require changing the timing of all subsequent steps in an assay. For example, combining two steps into a single step may allow, or may require, changes in the timing or duration of other steps in the assay. For example, increasing the assay temperature may speed the progress of chemical reactions in an assay, and so may require changing (e.g., shortening) the duration or timing of assay steps which involve temperature-sensitive chemical reactions. For example, eliminating a pretreatment step may require changes in reagents used in other assay steps. In addition, as noted above, methods disclosed herein comprise iterative methods; such iterative methods allow for multiple changes in step parameters. Such multiple changes may include successive changes, may include simultaneous changes, and may include instances of simultaneous and successive changes to step parameters.

As disclosed herein, methods for improving assays, including iterative methods for altering a baseline assay, will preferably provide assays which, as compared to the baseline assay: are of shorter total duration; are simpler to perform; contain fewer steps; require less sample volume; require less, or no, pretreatment of the sample; require fewer reagents, or lesser volumes of reagent; are less costly to perform; require only a single detection step, which is preferably an optical detection step; use more stable reagents; and differ from the baseline assay in other ways.

Accordingly, in embodiments, an improved method, developed according to the methods for improving assays disclosed herein, including iterative methods for altering a baseline assay, will preferably provide assays using a sample volume of less than or equal to about 1 µL in volume that provide usable responses across a wide range of samples and subjects and which, as compared to the baseline assay, differ from the baseline assays in lacking sample pretreatment; requiring only about 2 or fewer assay reagents; requiring only about 3 or fewer assay steps; requiring a total assay time of about 10 min or less; providing a flexible time period during which the sample is incubated with the reagents; providing assays utilizing inexpensive reagents (e.g., where the cost of reagents used in running an assay is about 1¢ or less); providing a flexible time period during which calibration steps may be performed; and other assay attributes. Preferably, the methods disclosed herein allow for, and may provide means to, define the assay kinetics and the method of reading an assay (e.g., whether the results are obtained by either end-point methods or kinetic methods).

In practice, the methods for improving an assay may be performed over a narrow range (typically four-fold) of sample volume or analyte concentration. Important parameters include the assay accuracy, assay precision, and the correlation of the assay with calibration results. Clinical correlation of the assay and assay results is also an important parameter. If design goals are not met during an initial round applying these methods, then further iterations of these methods may be performed, altering the baseline method in order to develop improved methods from those baseline methods. The new assay conditions and procedures followed in a second, and any further rounds, may be documented at once upon identification of improved methods, as compared to the baseline assay.

Calibrators and Calibration Methods

Assay development, including improving an assay, requires attention to calibration of the assay, and to calibration reagents, as well as to the steps and chemistry required to detect an analyte in an unknown sample. In embodiments, a baseline assay may include satisfactory calibration methods, and satisfactory calibration reagents. However, where calibration methods or reagents are not satisfactory, or where such calibration methods and calibration reagents may be improved, the present methods may be used to improve calibration steps and calibration reagents as well as other assay steps and reagents.

Methods for improving calibration steps and calibration agents include, for example: selecting calibration materials and appropriate calibration points;

Selecting a reportable range (for the results obtained by the methods);

Selecting a calibrator matrix;

Determining whether to use a single analyte or multiplexed analytes in the calibration solution (preferably, several lots of calibrators will be made for comparison);

Selecting storage conditions for long term stability of the calibrators and calibration reagents; and Conducting stability studies at several temperatures (e.g., at 4° C., at room temperature (RT); at 37° C.; and other temperatures).

In preferred situations, the results of such improvement of calibration reagents provides reagents that are stable for three months or longer when stored under refrigeration, at about 4° C.

Upon identification of an improved assay, the assay and calibration steps and reagents may be documented. If the assays and calibration steps and reagents were identified using a particular machine or machines, and the assays may be performed on other equipment as well, then these improved assays may also be verified using the other equipment and any adjustments required for their performance on the other equipment documented.

Validation of Improved Assays on Alternate Systems or Equipment

Different pieces of laboratory equipment, including different sensors or detectors (e.g., spectrophotometers, luminometers, absorbance meters, fluorimeters, charge-coupled device (CCD) sensors and cameras, photodiodes, and other detectors) often have different operating requirements and sensitivities. Upon identification of an improved assay according to the methods disclosed herein using particular equipment, termed the "first equipment system", it may be desired to validate (and alter if necessary) the improved assay for use on different equipment (termed a "second equipment system").

Methods for such further alteration of improved assays for use on different equipment may include one or more of the following:

Reagents may be made according to documented manufacturing procedures (MPAs) and subject to functional quality control using standard operating procedures;

If needed, reagents may be re-formulated for stability when used with the different equipment;

If needed, reagents may be re-formulated for compatibility for use with the different equipment;

Improved assays may be run on the different equipment and the results compared with the previously obtained results of improved assays;

Performance of the assays on the second equipment system may be compared to the performance of the assays on the first equipment system; if the performance on the second equipment system does not match that on the first equipment system, then the reagents, assays steps, and other parameters may be adjusted according to the methods disclosed herein, and the improved assays adapted for use on the second equipment system using the improved assays developed on the first equipment system as a baseline assay.

Improvement of Two or More Assays for Use Together

Improvement of a single assay provides benefits, including a better assay, and often a faster, or simpler, or cheaper, assay than the baseline assay.

Further advantages may be obtained by improving two or more assays, particularly where the improvement of at least one of the assays allows better co-ordination of the performance of both assays. Such better co-ordination of the performance of two or more assays may include the ability to perform the improved two (or more) assays with a single biological sample, or with a smaller amount of biological sample, or both, as compared to the number of samples, or amount of sample, or both, required to perform the two (or more) baseline assays. Such better co-ordination of the performance of two or more assays may include the more rapid performance of the improved two (or more) assays as compared to the time required to perform the two (or more) baseline assays. Such better co-ordination of the performance of two or more assays may include the more accurate performance of the improved two (or more) assays as compared to the accuracy of the two (or more) baseline assays. Such better co-ordination of the performance of two or more assays may include the more reliable (e.g., more repeatable, with less assay-to-assay variation) performance of the improved two (or more) assays as compared to the reliability (e.g., repeatability) of the two (or more) baseline assays. Such better co-ordination of the performance of two or more assays may include the ability to use the same, or to use compatible, detection apparatus (or detection steps) in the performance of the improved two (or more) assays. Such better co-ordination of the performance of two or more assays may include the less costly performance of the improved two (or more) assays as compared to the cost of performing the two (or more) baseline assays. Such better co-ordination of the performance of two or more assays may include the combination of steps, or the use of similar reagents, diluents, or treatments for the improved two (or more) assays, which could not be, or was not, done in the performance of the two (or more) baseline assays. Such better co-ordination of the performance of two or more assays may include synergies in the performance of assay steps of, or synergistic improvements in the results obtained by, the improved two (or more) assays as compared to the two (or more) baseline assays.

Figure 10:
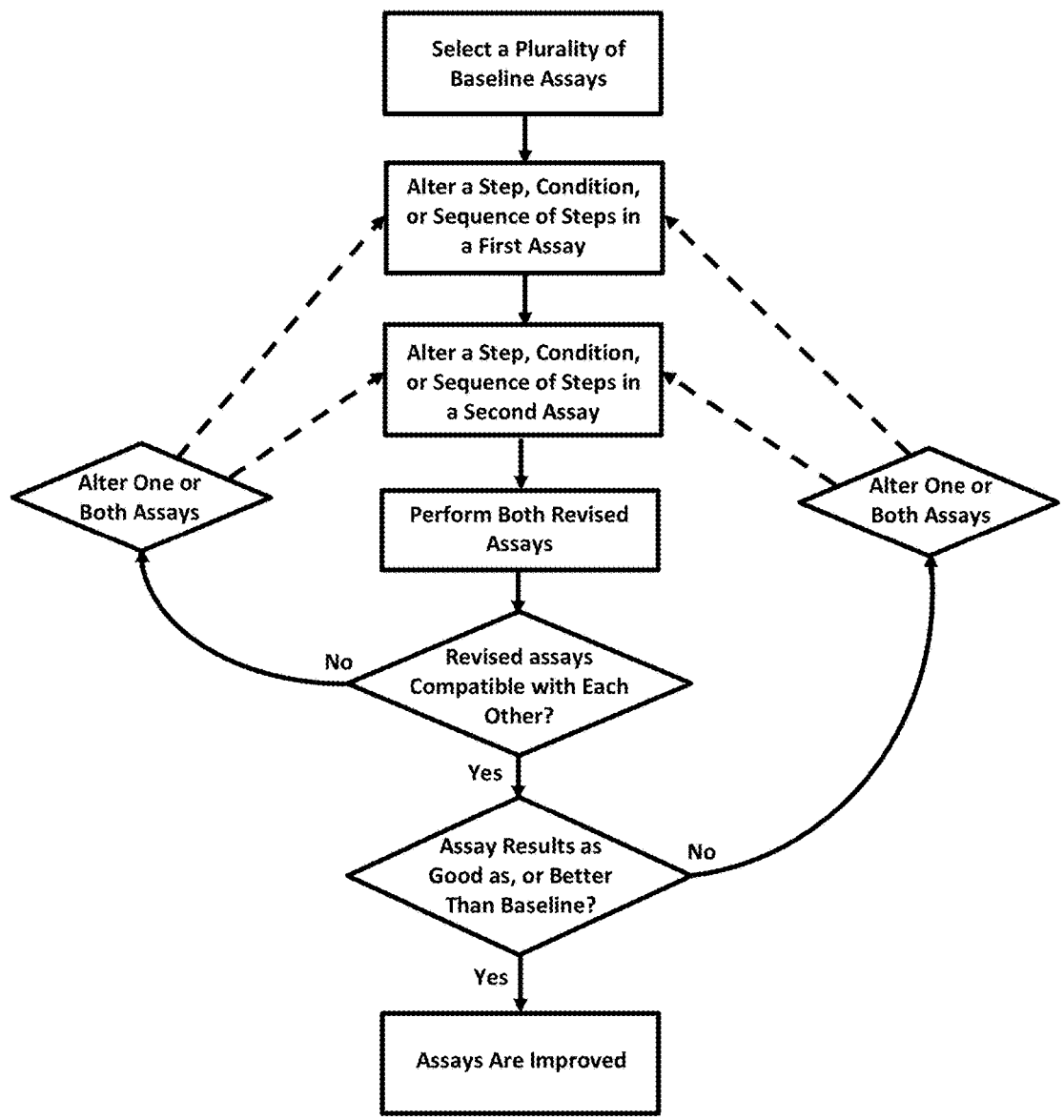
FIG. 10 illustrates an embodiment of methods for improving a plurality of assays so that multiple assays work better together, e.g., so that the performance of pairs or multiples of assays using the same biological sample, or aliquots of the same biological sample or dilutions thereof, is improved. Embodiments of these methods include altering a reagent, a treatment, a step, a sequence of steps, or any other element in one or more of the assays. Embodiments of the methods include determining whether or not the revised assays are compatible (e.g., may be performed together using portions of a single biological sample).

FIG. 10 illustrates an embodiment of methods for improving a plurality of assays so that multiple assays work better together, e.g., so that the performance of pairs or multiples of assays using the same initial sample, or aliquots of the same initial sample, is improved. As shown, embodiments of these methods include altering a step, a condition, or the sequence of steps in a first assay; altering a step, a condition, or the sequence of steps in a first assay; determining whether or not the revised assays are compatible (e.g., may be performed together using portions of a single biological sample). Dotted arrows indicate optional or alternative steps (e.g., although in embodiments, both the first and second assay may be altered following determination that the revised assays are not compatible with each other, or that the revised assays are not as good as, or better than, a baseline assay, in some embodiments, only one of, but not both, the first and the second assay may be altered following determination that the revised assays are not compatible with each other, or that the revised assays are not as good as, or better than, a baseline assay). Assay improvements include, for example, multiplexing of assays so that pairs or multiples of assays need not be performed sequentially (i.e., performance of a second assay may be begun prior to the completion of a first assay). Such improvements may include performance of the assays under the same, or compatible conditions, or using the same detector(s), or adjusting assay conditions so that dilutions and aliquots of a single sample may be used for all assays without requiring additional sample collection from the subject. Iterative procedures as shown in the figure provide improved assays compatible for use together, e.g., in the same instrument or the same system, using a single biological sample. In preferred embodiments, the single biological sample is a small biological sample, such as a single drop of blood or of urine. The assays are considered improved, and may be considered improved, if the results of the revised assays are as good as, or better than, the results of the baseline assays (e.g., the assays as performed without the alterations).

Figure 11:
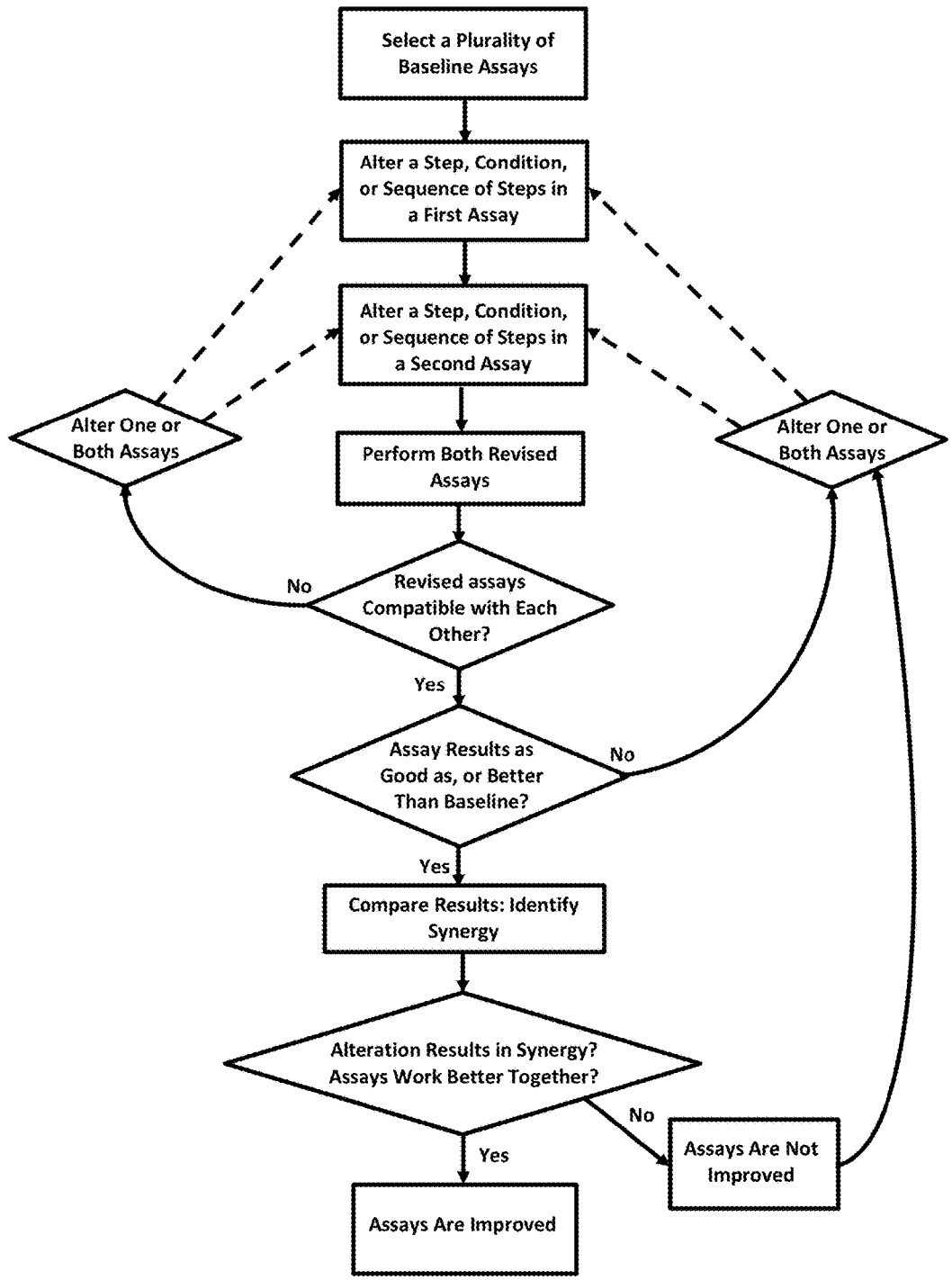
FIG. 11 illustrates further embodiments of methods for improving assays so that multiple assays work better together. Iterative procedures as shown in the figure provide improved assays compatible for use together, e.g., in the same instrument or the same system, using a single biological sample. In preferred embodiments, the single biological sample is a small biological sample, such as a single drop of blood or of urine. These methods for improving an assay include identifying assay alterations which lead to synergistic effects on the performance and results of the assay.

FIG. 11 illustrates an embodiment of methods for improving assays so that multiple assays work better together, e.g., the performance of pairs or multiples of assays using the same initial sample, or aliquots of the same initial sample, is improved. As shown, embodiments of these methods include altering a step, a condition, or the sequence of steps in a first assay; altering a step, a condition, or the sequence of steps in a first assay; determining whether or not the revised assays are compatible (e.g., may be performed together using portions of a single biological sample). Dotted arrows indicate optional or alternative steps (e.g., although in embodiments, both the first and second assay may be altered following determination that the revised assays are not compatible with each other, or that the revised assays are not as good as, or better than, a baseline assay, in some embodiments, only one of, but not both, the first and the second assay may be altered following determination that the revised assays are not compatible with each other, or that the revised assays are not as good as, or better than, a baseline assay). Such improvements include, for example, multiplexing of assays so that pairs or multiples of assays need not be performed sequentially (i.e., performance of a second assay may be begun prior to the completion of a first assay). Such improvements may include performance of the assays under the same, or compatible conditions, or using the same detector(s), or adjusting assay conditions so that dilutions and aliquots of a single sample may be used for all assays without requiring additional sample collection from the subject. Iterative procedures as shown in the figure provide improved assays compatible for use together, e.g., in the same instrument or the same system, using a single biological sample. In preferred embodiments, the single biological sample is a small biological sample, such as a single drop of blood or of urine. These methods for improving an assay include identifying assay alterations which lead to synergistic effects on the performance and results of the assay. Thus, methods for improving an assay include providing assay alterations which lead to synergistic effects which improve the performance and results of the assay.

EXAMPLES

The assays discussed in the following all make use of optical detectors to detect photons emitted during an assay, indicating the presence of, or amount of, a target analyte of interest. The photons may be emitted, for example, from a fluorescent, luminescent or chemiluminescent moiety. Such photons may be detected by any of several means known in the art: e.g., by photomulitiplier tubes, photodiodes, charge-coupled devices, film exposure, or any other suitable means. Cameras, microscopes, light-meters, spectrophotometers, and other commercially available equipment can be used to make such measurements. For example, a commercial instrument (e.g., a Molecular Devices SpectraMax® M5 micro-titer plate reader (Molecular Devices, Sunnyvale, Calif.); a Beckman-Coulter DU® 700 spectrophotometer (Beckman-Coulter, Brea, Calif., USA); or a Zeiss multi-channel MCS UV-NIR spectrometer module (Carl Zeiss, Thornwood, N.Y., USA)) may be used; or proprietary or lab-built equipment may be used.

Example 1

Vitamin B12 Assay—A Specific Binding Assay

Vitamin B12 (B12) is a water-soluble complex organic molecule including a single cobalt ion (Co(III)) bound to four nitrogen atoms within a central, asymmetric corrin ring structure; B12 also includes a phosphate group and several amine groups. The cobalt can also bind to a cyanide group, a hydroxyl group, an adenosyl group, or a methyl group. Alternative forms of B12, such as cyanocobalamin (in which the cobalt binds cyanide, and which is the form most commonly supplied as a dietary supplement) are converted in the human body to the physiologically useful forms methylcobalamin and 5-deoxyadenosyl cobalamin.

Animals obtain B12 from the diet. Individual subjects may suffer from B12 deficiency when too little is absorbed in the digestive tract, as may occur in malnutrition, chronic alcoholism, starvation, pernicious anemia (an autoimmune disorder) or for other reasons. B12 deficiency may lead to fatigue, depression, or memory loss; more severe levels of B12 deficiency can cause permanent neurological defects, and other medical problems; the low B12 levels found in pernicious anemia are treated with B12 supplements or injections. Thus, the maintenance of sufficient B12 is believed to be critical to the health of human subjects, and the restoration of normal B12 levels is a therapeutic goal for individuals suffering from a variety of disorders.

Determination of B12 levels in blood may be useful in assessing the clinical status of the subject from whom the blood was obtained. Commercial vitamin B12 assays are available. However, present methods for determining the levels of these and other molecules, whether naturally present in the blood or otherwise, are often inaccurate, difficult, expensive, and time-consuming. Accordingly, improved methods for the determination of vitamin B12 levels in clinical samples are desired.

An improved assay was developed, and is described in the following according to the methods disclosed herein. This improved assay is designed to detect vitamin B12 (with a reportable range of between 250 pg/mL and 4000 pg/mL) in human serum and plasma samples. The assay is calibrated using Cyanocobalamin (Sigma, Cat#C3607-500MG). (This reagent meets USP specifications for a clinical reference.) The Siemens Immulite® 2000 (Siemens AG, Erlangen, Germany) was used to perform a reference Vitamin B12 assay for comparison.

The Baseline Assay

Commercially available tests were used to provide the baseline assay to be altered and improved according to the methods disclosed herein. A typical vitamin B12 assay includes the following steps:
 (i) denaturation using a high pH buffer (this step aims to release B12 bound to binding proteins in the sample by denaturing them);
 (ii) treatment with a reducing agent to further breakdown binding proteins as well as intrinsic factor autoantibodies;
 (iii) neutralization of sample following the high pH and reducing agent steps;
 (iv) binding sample B12 and a known amount of added, labeled B12-conjugate to a binding protein or anti-B12 antibody; and
 (v) detecting bound B12.

In addition, commercial tests take steps to reduce confounding signals by B12 analogs and to reduce non-specific binding by any residual contamination by "R protein" (non-intrinsic factor), which binds vitamin B12 and many B12 analogs. Thus, tests typically provide KCN to convert all forms of vitamin B12 to the cyanocobalamin form (which is bound by IF), and also provide dicyanocobinamide (not bound by IF) in order to saturate any R protein binding sites that escaped denaturation, to insure that any residual R protein does not bind B12.

The AccuLite CLIA Microwells Vitamin B-12 Test System (Monobind Inc., Lake Forest CA, USA; Catalog #7675-300) served as a baseline assay for comparison and for improvement. Thus, the assay alterations discussed below are discussed in comparison with the assay strategy and steps of the Monobind Vitamin B-12 Test.

The baseline assay (e.g., Monobind Vitamin B-12 Test) uses avidin bound to a surface or solid phase to capture biotinylated anti-B12 antibodies. The unknown amount of B12 from the sample competes with added B12-horse radish peroxidase conjugate (B12-HRP) for binding to the anti-B12 antibodies. These anti-B12 antibodies, with bound B12 or B12-HRP, are immobilized on the surface via a biotin-avidin linkage. Hydrogen peroxide (along with luminol) is added, producing measurable light emission by action of the HRP on its substrate. Measurement of the light emitted provides a measurement of the amount of the B12-HRP conjugate bound. The maximal amount of light emission occurs when all the added B12-HRP remains (i.e., the sample adds no B12); and the minimal amount of light emission occurs when only a minimal amount of B12-HRP remains (i.e., B12 from the sample occupies virtually all of the antibody binding sites). Since the amount of B12-HRP conjugate is known, comparison of the light emission measured with a calibration curve allows determination of the free B12 from the sample.

In particular, the Monobind Vitamin B-12 Test extracts vitamin B12 from 100 µL of sample (taking 50 µL of the resulting 2-fold diluted, pre-treated sample per assay), is run at room temperature (20° C. to 27° C.), uses biotinylated rabbit anti-Vitamin B-12 antibodies to bind sample B12, and uses horse radish peroxidase-labeled B12 (B12-HRP) conjugates to provide a detectable signal. B12 is liberated from its binding proteins by treating the sample with a high pH NaOH reagent that also includes potassium cyanide (KCN) and a stabilizing agent (Tris(2-carboxyethyl)phosphine hydrochloride) (TCEP); these reagents denature the B12 binding proteins, freeing B12 for analysis. Following this step, a neutralization buffer is added to the treated sample to reduce the pH. These extraction steps take 15 minutes and dilute the sample two-fold.

Following the extraction steps, sample and a solution containing the biotinylated anti-vitamin B12 antibodies are mixed together in avidin-coated wells in a 96-well plate, where they incubate for 45 minutes at room temperature. Following this incubation, a known amount of B12-HRP is added to the well, and the mixture incubates at room temperature for 30 minutes. The wells are then washed, and a solution containing hydrogen peroxide and luminol is added; this mixture sits at room temperature for 5 minutes. Following this final incubation period, the light emitted by the HRP in each well acting on the hydrogen peroxide in the presence of the luminol is read in a luminometer. Comparison of these light readings to a calibration curve provides B12 values for the samples. The time required to perform the baseline assay is at least 95 minutes (excluding time taken for pipetting and other activities).

Alteration of Assay Steps: Improvement of the Baseline Assay

Alterations in the strategy as well as in the reagent compositions and timing of the assay were made in order to improve the assay, according to the methods disclosed herein. One goal of some of the alterations was to adapt the baseline assay for use on an automatic sample analysis system. Other goals included reducing sample volume, increasing the assay temperature to above room temperature, simplifying the assay, and reducing the duration of the assay.

Thus, since the baseline assay requires a sample volume of 100 μL (i.e., more than 25 μL), per the methods disclosed herein, the sample used in the assay was altered by reducing the sample volume to 16 μL.

As discussed above, since B12 in blood is bound to IF, R protein, and other proteins in clinical samples, it is necessary to denature the B12 carrier proteins in order to release the vitamin B12. Thus, this pretreatment step was not eliminated. However, the pretreatment step was shortened in the altered assay: the baseline assay requires a 15 minute incubation in the presence of "releasing agent" (high pH and KCN solution); the altered assay requires a shorter (only 10 minutes) incubation period at high pH in the presence of KCN. The altered assay includes dicyanoncobinamide (to saturate R protein) in this solution as well, combining release of vitamin B12 with saturation of R protein in a single step.

The baseline assay was performed at room temperature. Thus, an initial adaptation was to alter the assay temperature to 34° C. As discussed above, this alteration typically speeds reaction kinetics, and so should aid in reducing assay duration; this was found to be the case in the present example (e.g., the pretreatment step was shortened, as were subsequent steps, while maintaining the performance of the assay).

The assay strategy and components were also altered; for example, the altered assay used the native B12 binding protein, intrinsic factor (IF), to bind the target analyte instead of using the anti-vitamin B12 antibodies. Both the baseline assay and the altered assay used biotinylation to aid immobilization of the bound B12. However, the baseline assay used biotinylated anti-vitamin B12 antibodies bound to avidin-coated plates. The improved assay used an Ultra-Avidin™ (Leinco Technologies, St. Louis, Mo., USA; Catalog # A110) coated surface to bind biotinylated IF (the B12 binder) in the altered assay.

Other assay components were altered as well; for example, alkaline phosphatase and its substrate dioxetane are used to produce a chemiluminescent signal instead of horse radish peroxidase, hydrogen peroxide, and luminol. In particular, the B12 conjugate was changed from a B12-HRP conjugate (as used in the baseline assay) to a B12-alkaline phosphatase (B12-AP) conjugate. Further adaptations were then made to improve the performance of the baseline assay and to adapt it for use on an automatic sample analysis system. Thus, following the steps disclosed herein, the baseline vitamin B12 assay was altered and improved, so as to perform a vitamin B12 assay in less time with less sample at higher temperature, using a preferred detection method, on an automatic assay system.

The Improved Assay

Application of the strategies disclosed herein provide an improved assay as compared to the baseline assay. Thus, as compared to the baseline assay, the improved assay uses altered reagents, altered timing, and altered steps as described in the following.

Step 1: 30 μL of sample treatment buffer A and sample treatment buffer B are mixed (1:1) in a container to give a total volume of 60 μL. The combined mixture of these buffers provides a high pH solution that includes 0.2 N NaOH, KCN, dicyanocobinamide, dithiothreitol (DTT), ethylene diamine tetra acetic acid (EDTA), a sugar, sodium phosphate and sodium chloride. A portion (24 μL) of this mixture is taken to a separate container for mixing with a sample aliquot.

Step 2: Sample (16 μL) is added to the 24 μL of the solution prepared in step 1 and mixed. This mixture is incubated for 10 min to accomplish extraction of vitamin B12 from the sample. The sample dilution at this point is 1:2.5.

Step 3: Following the above incubation, 20 μL of neutralization reagent (including 0.1 N HCl) is added, reducing the pH and resulting in a sample dilution of 1:3.75.

Step 4: Immediately after step 3, 10 μL of a solution containing biotinylated intrinsic factor (biotinylated-IF) is added to above mixture, followed by the addition of 10 μL of the B12-AP conjugate; these additions bring the effective sample dilution to 1:5.

Step 5: After steps 1-4, 12 μL of the mixture is moved to a container which has an inner surface coated with Ultra-Avidin™ and is suitable for chemiluminescence measurements. The mixture is allowed to incubate in contact with the coated surface for 10 minutes. After this incubation period in the presence of bound UltraAvidin™, the mixture containing sample is removed from the container.

Step 6: The container is then washed six times (20 μL per wash) with a buffer containing Tween 20 in 50 mM Tris-buffered saline solution with Sodium Azide, pH 8.0; one minute of incubation separates each 20 μL wash from the subsequent wash.

Step 7: Substrate incubation: Following removal of the last wash, 15 μL of dioxetane solution (pH 9.7) (a substrate for the alkaline phosphatase enzyme) is added to the container, and let incubate for 10 minutes.

Step 8: Chemiluminescence is read.

Step 9: The measured luminosity value is compared to a standard curve in order to determine the concentration of vitamin B12 in the sample. A calibration curve is prepared using B12-free serum "spiked" with B12 (e.g., cyanocobalamin from Sigma (Cat#C3607-500MG)).

The total time to perform the improved assay is about 36 minutes.

The improved assay provides a clinically valuable determination of vitamin B12 from blood (plasma or serum) samples, using less sample, less time, and preferred methods as compared to the baseline assay. The results of the improved assay compare well with assays performed on matched samples.

Figure 12:
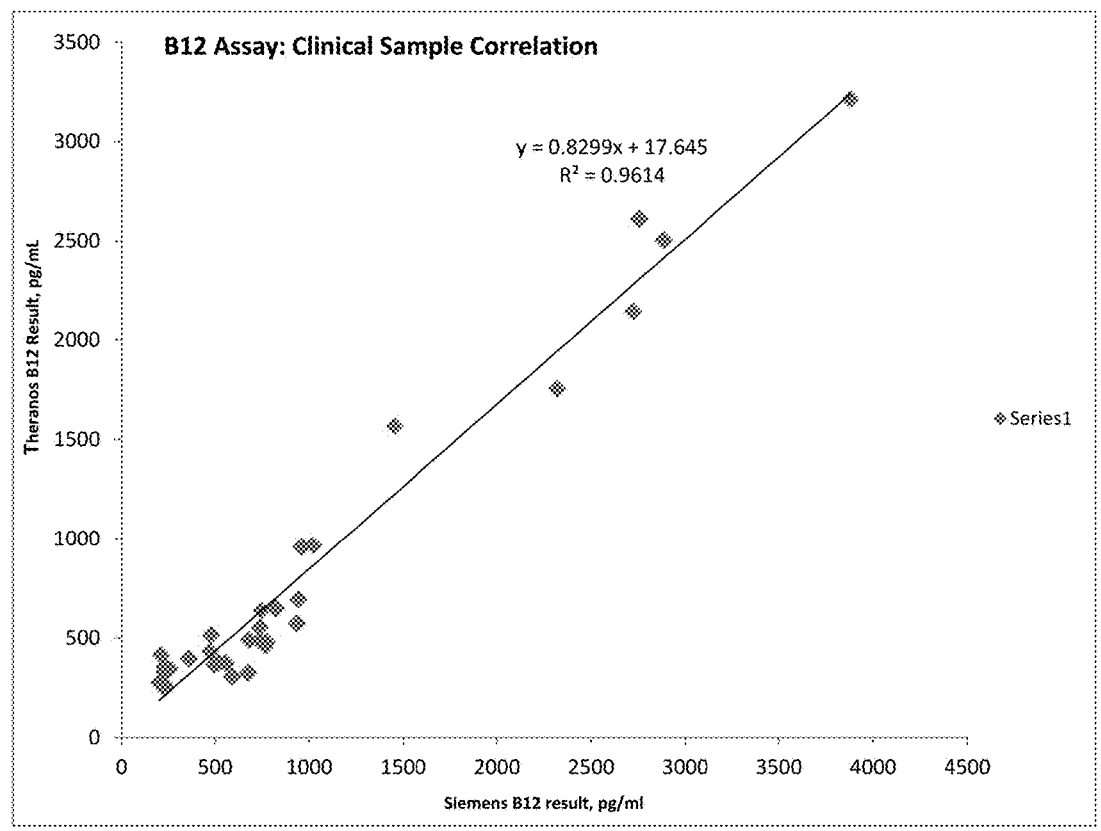
FIG. 12 presents vitamin B12 measurements from 34 serum samples. The results from matched samples were obtained in two ways: using an improved assay as disclosed herein, and using a commercial clinical assay. The results are plotted against each other (the commercial assay results plotted along the horizontal axis, the results of the improved assay plotted along the vertical axis). The results of both assays compare very well, with an $R^2$ value of 0.96.

A comparison of the B12 measurements made on matched samples using the improved assay and the commercially available Siemens Immulite B12 assay are shown in FIG. 12.

The results shown in FIG. 12 were obtained from 34 serum samples (20 from anemic subjects and 14 from clinical subjects; the serum samples were obtained from commercial sources). All samples were run according to the improved vitamin B12 assay disclosed in this example, and were also run in a CLIA-certified lab on a Siemens Immulite machine according to the manufacturer's vitamin B12 assay protocol. The anemic subjects turned out to have high levels of B12. This was confirmed by looking at the patient information sheets obtained from the commercial vendors which cited the patients taking vitamin B12 supplements.

The correlation with the CLIA assay was excellent with an R value of 0.96 and a slope of 0.82.

The following table presents adaptations made to adapt the baseline assay for use on an automatic sample analysis system and to reduce the sample volume required, reduce the time required, and to otherwise improve the performance of the baseline assay.

|  | Baseline Assay | Altered Assay |
| --- | --- | --- |
| Assay Temperature | 20° C.-27° C. | 34° C. |
| Sample Size | 100 μL (50 μL is used) | 16 μL |
| Sample Dilution | 1:2 | 1:5 |
| B12 Binder | Anti-B12 antibody | Intrinsic Factor (IF) |
| B12 Conjugate | B12-HRP | B12-AP |
| Pretreatment Duration | 15 minutes | 10 minutes |
| B12 Binder Incubation Period Duration | 45 minutes (in avidin-coated wells) | IF, B12-AP conjugate are combined in step 4, prior to incubation |
| B12 Conjugate Incubation Period | 30 minutes | 10 minutes (step 5, IF, B12-AP incubate in UltraAvidin ™-coated container) |
| Substrate Incubation Period | 5 minutes (luminol, H$_2$O$_2$) | 10 minutes (dioxetane) |
| Total Assay Duration | 95 minutes | 36 minutes |

Example 2

Cytometry Assay

Assay improvements may be made by improving the speed of the assay, by reducing the complexity of the assay, and by other means, all of which typically improve the accuracy and precision of an assay. For example, reducing the complexity of an assay typically improves reliability and repeatability (which both impact accuracy and precision) since there is less time and fewer opportunities for variation and error. Speeding up an assay may provide similar benefits.

Rapid analysis results may be used to provide real-time information relevant to the treatment, diagnosis, or monitoring of a patient. For example, rapid analysis results may be used to guide a treatment decision of a surgeon operating on a patient. During surgery, a surgeon may obtain a biological sample from a patient for analysis. By receiving rapid analysis of a sample by a method provided herein, a surgeon may be able to make a treatment decision during the course of surgery.

In another example, rapid analysis results may allow a patient to receive information regarding a biological sample provided by the patient at a point of service location during the same visit in which the patient provided the biological sample.

Applicants describe herein an assay which may be used to prepare a sample of whole blood for imaging analysis of white blood cells for the presence of multiple markers and cell types. The example discusses improvements made to the assay. The initial assay which serves as the baseline assay which was improved per the methods disclosed herein included several steps in which dye was added to whole blood, and the sample incubated for a length of time; cells were lysed and fixed; excess dye was washed away; the cells were concentrated by centrifugation; the pellet was resuspended; and the cells were loaded into an imaging cuvette and allowed to settle. Examples of such assays, and of results obtained from such assays, are provided, for example, in U.S. Patent Application 61/802,194, filed Mar. 15, 2013, the entire contents of which are hereby incorporated by reference in their entirety.

Such assays are useful for preparing samples of whole blood for imaging analysis; sample preparation according to the original assay took over 30 minutes; with improvements provided per the methods disclosed herein, the whole blood samples are ready for imaging in less than about 15 minutes. Automated cytometric analysis of such prepared cells may also be done rapidly, so that cytometric WBC analysis can be performed from whole blood in about half an hour or less. In addition, this assay uses only a small volume of the blood sample, so is sparing of resources, and less inconvenient or uncomfortable to a subject than assays which require larger volumes of blood.

Baseline and Improved White Blood Cell Assays

The following presents assays for preparing samples of whole blood for cytometric analysis of white blood cells. Both the baseline assay and the improved assay are performed at 37° C., and require 50 μL of blood; since the assay temperature and sample volume were already near to the desired values for improved assays, improvements to the baseline assay were made by shortening, combining, or eliminating steps in order to provide a more rapid assay than the baseline assay.

Baseline Assay: Reagents

Reagents used in the baseline assay include: phosphate buffer, resuspension buffer, lysis buffer, fixation buffer, and reagent cocktails which contain dyes and dye-conjugated antibodies. The antibodies are directed to specific WBC markers.

Phosphate buffered saline (PBS): 137 mM NaCl, 3 mM KCl, 8 mM, Na$_2$HPO$_4$, 1.5 mM KH$_2$PO$_4$, pH adjusted to pH 7.2 to pH 7.4 (with HCl).

Wash buffer (WB): 0.2% bovine serum albumin (BSA) in PBS.

Ammonium Chloride Lyse buffer: 75 mM KCl, 10 mM HCO$_3$, 0.1 mM EDTA, pH 7.2.

Fixation buffer: 10% paraformaldehyde in PBS.

Antibody Cocktail: anti-CD14 antibody conjugated to Pacific Blue™ dye; anti-CD16 antibody conjugated to phycoerythrin (PE) dye; anti-CD123 antibody conjugated to PE dye; anti-CD3 antibody conjugated to AlexzaFluor® 647 (AF747) dye; anti-CD19 antibody conjugated to AF747 dye; anti-CD20 antibody conjugated to AF747 dye; anti-CD45 antibody conjugated to AF747 dye; anti-CD56 antibody conjugated to Allophycocyanin (APC) dye; and Fc block (mouse IgG), in 25% BSA in PBS.

Nuclear Dye Cocktail: DRAQ5® in 0.2% BSA in PBS.

Baseline Assay: Protocol

Obtain 50 μL of whole blood from a subject.

Mix with approximately 10 μL of the Antibody Cocktail. Incubate for 10 minutes at 37° C.

Add approximately 1 μL of the Nuclear Dye Cocktail. Incubate for 5 minutes at 37° C.

Add 5-fold to 8-fold volume of Lysis Buffer (approximately 300-500 μL); gently pipette 5 times to mix the solution.

Incubate for 2.5 minutes at 37° C. to lyse the red blood cells (RBCs).

Add approximately 20 μL of the Fixation buffer (final paraformaldehyde concentration is about 0.5%).

Incubate for 2.5 minutes at 37° C.

Centrifuge the sample at 1200×g for 3 minutes, and then resuspend in WB (PBS with 0.2% BSA). Add beads (e.g., 10 μm polystyrene beads at 1000 beads per μL).

Centrifuge the sample mixture at 1000×g for 3 minutes.

Remove the supernatant (approximately 350 µL) leaving approximately 50 µL of sample in the tube (pellet and supernatant).

Resuspend with gentle pipetting of the sample up and down in the tube.

Load the final mixture on a pre-warmed imaging cuvette (37° C.).

Allow the cells to settle in the cuvette at 37° C. for 5 minutes before imaging.

Image the sample.

Thus the baseline assay takes whole blood and prepares it for imaging in 7 steps that take about 31 minutes (excluding pipetting and other transfer and processing actions between the steps, which may require some additional time). A schematic diagram of the baseline assay steps is presented in FIG. 13.

This baseline assay was altered and improved by combining steps, deleting steps, and shortening steps, to provide the following improved assay.

Improved Assay: Reagents

Reagents used in this assay include: phosphate buffer, resuspension buffer, and reagent cocktails which contain dyes and dye-conjugated antibodies. The antibodies are directed to specific WBC markers.

Phosphate buffer (PBS): 137 mM NaCl, 3 mM KCl, 8 mM, $Na_2HPO_4$, 1.5 mM $KH_2PO_4$, pH adjusted to pH to 7.2 to pH 7.4 (with HCl).

Lyse fix buffer: 0.0266% saponin in PBS with 0.6% paraformaldehyde (PFA), where "%" indicates grams/100 mL. This buffer typically includes a known concentration of small beads (e.g., 1000 beads/µL; beads are typically 1-10 µm in diameter) which serve as a target for auto-focusing for automatic imaging, and as a standard for use in calculating the concentration of cells in a sample.

Reagent Cocktail 1: DRAQ5®, anti-CD14 antibody conjugated to Pacific Blue™ dye, Fc block (e.g., immunoglobulin), in 0.2% BSA in PBS.

Reagent Cocktail 2: anti-CD16 antibody conjugated to phycoerythrin (PE) dye, anti-CD45 antibody conjugated to AlexzaFluor® 647 dye, anti-CD123 antibody conjugated to PECy5 dye, Fc block (e.g., immunoglobulin), in 15% BSA in PBS.

Improved Assay: Protocol

Obtain whole blood from a subject.

Place 50 µL of whole blood in a tube. If desired, the blood sample may be acquired directly to a tube. Where 50 µL is the total amount of blood taken from the subject, then the entire sample is added or acquired to a tube; where more than 50 µL is acquired from a subject, then the 50 µL is an aliquot of the sample. Note that volume of aliquot may be less than 50 µL; may be, e.g., 20 µL.

Add Cocktail 1 (approximately 5 µL).

Incubate samples at 37° C. for 2 minutes.

Add Lyse Fix buffer (at a 6:1 ratio of (lyse fix buffer) to (stained blood); approximately 300-350 µL). A known concentration of beads may be included in the Lyse Fix buffer to provide targets (reference particles) for focusing and to provide a calibration for the concentration of the sample (e.g., as described above under the heading "Context-based Autofocus").

Incubate in the lyse fix buffer at 37° C. for 3 minutes; at 1.5 minutes after addition of the buffer, mix by pipetting the solution up and down five times.

Centrifuge the sample mixture at 1200×g for 1.5 minutes.

Remove the supernatant (approximately 350 µL). Save the supernatant to adjust the volume, if needed, in later steps.

Add Cocktail 2 (approximately 15 µL) to resuspend the cells, providing the final mixture.

Load the final mixture on a pre-warmed imaging cuvette (37° C.).

Incubate the cuvette at 37° C. for 5 minutes before imaging.

Image the sample.

Thus, the sample is ready for imaging in less than 15 minutes (e.g., 11.5 minutes excluding anytime required for aliquotting, transfer, or other operations). A schematic diagram of the steps of the improved assay is presented in FIG. 13.

Since the methods disclosed above prepare the sample using cocktails which include multiple dyes, analysis of these samples for the presence of several cell-type markers may be performed within a single field of view, providing efficient imaging of the samples with minimal duplication of effort. Light scatter images of these same fields of view provides yet another aspect of analysis which may be applied efficiently without requiring separate samples or separate fields of view for the several modes of image analysis of the samples. Inclusion of reference particles of a known size further aids imaging by allowing use of automatic focusing and, since the concentration of the reference particles is known, provides an independent measure of sample dilution and cell concentration in each image.

The imaging of the prepared sample may also be done rapidly; for example, such imaging may be performed in about 10 minutes (typically between about 2 minutes and about 12 minutes) by automatic devices having features as described, for example, in U.S. patent application Ser. No. 13/244,947, in U.S. patent application Ser. No. 13/769,779, and related applications. Thus, in embodiments, the entire analysis, including preparation of the blood sample and imaging of the prepared sample, may be performed in about 20 or 30 minutes or less.

The images and image analysis obtained from samples prepared according to the methods discussed above are suitable for identifying different populations of WBCs from whole blood. Such identification and quantification is done rapidly on the same sample by illumination of the sample (e.g., sequentially) with different wavelengths of light and recording and analyzing the resulting images and light intensities. Such methods are suitable for providing the images and plots as shown, for example, in FIGS. 9, 10, and 11, which were prepared using the methods discussed above. The comparisons shown in FIG. 12 demonstrate that these methods are accurate and reliable, and correlate well with other methods (e.g., analysis by an Abbott CELL-DYN Ruby System (Abbott Diagnostics, Lake Forest, Ill., USA)) the reference analyzer used for the comparisons shown in FIG. 12.

Steps Taken to Improve the Baseline Assay

Combining and Simplifting Steps: Several steps, and the reagents used in them, were combined and simplified, and the time required for these steps was shortened; thus, the improved assay is easier to perform, and total time to perform the assay was decreased. For example, antibody and nuclear dye reagents were combined so that the initial staining step was simpler, involving only a monocyte marker (anti-CD14 antibody conjugated to Pacific Blue™) and a nuclear stain (DRAQ5®), and that step was shortened to only 2 minutes (the baseline assay took 15 minutes in two steps to apply these two stains, along with other dyes). In addition, the remaining antibody staining step (using a reduced number of antibody dye conjugates) was combined with the 5 minute settling step of the baseline assay, so that cell staining and cell settling occurred simultaneously over 5 minutes. In this way, the 15 minutes required for staining in the baseline assay (10 minutes in two steps to stain cells, plus 5 minutes to allow them to settle) was reduced to only 7 minutes (a 2 minute staining step and a 5 minute combined staining/settling step) in the improved assay. The separate lysis buffer and fixation buffer were combined into a single buffer, simplifying assay preparation as well as the performance of the assay. And, although there are two antibody/dye cocktails in both assays, the antibody/dye cocktails are simpler, containing fewer ingredients, than those of the baseline assay. These improvements are discussed below in greater detail.

Reagents:

For example, the number of antibodies in the antibody cocktail was reduced from 8 to 4 (the baseline assay included antibodies to CD3, CD14, CD16, CD19, CD20, CD45, CD56, and CD123; the improved assay only uses antibodies to CD14, CD16, CD45, and CD123). In particular, the baseline assay was modified as follows.

Incubation Time:

The baseline assay first added the Antibody Cocktail, and incubated for 10 minutes, and then added the Nuclear Stain Cocktail for a further 5 minute incubation (total antibody/dye incubation: 15 minutes). However, following iterative experimentation (in which the initial 10 minute incubation was reduced to a 5 minute incubation; the number of dyes was reduced; and different combinations of dyes were investigated), the initial incubation time was reduced to a total of 2 minutes (incubation with anti-CD14 and DRAQ5® in a single reagent). Incubation with the remaining (reduced number of) antibodies (anti-CD16, anti-CD45, and anti-CD123) was combined with the final step of allowing the cells to settle prior to imaging, for a total incubation time of 7 minutes (a reduction of 8 minutes from the baseline assay). However, since this final incubation is a combination of two steps that were separate in the baseline assay, these modifications shorten the total time of the improved assay by 13 minutes as compared the total time of the baseline assay.

Figure 13:
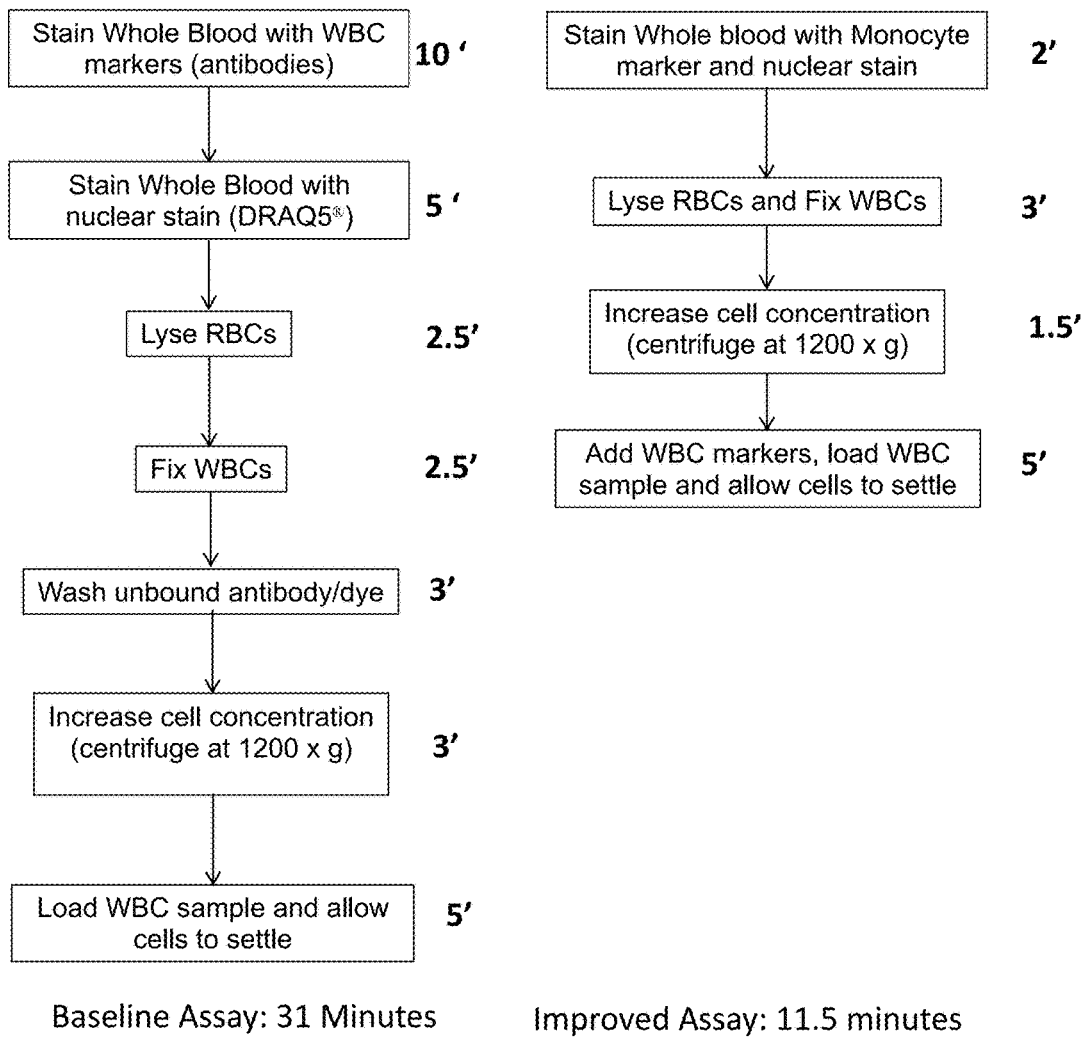
FIG. 13 presents schematic representations of the steps of a baseline assay for preparing white blood cells from blood for cytometric analysis (left-hand column) and the steps of an improved assay (based on the baseline assay; right-hand column). The baseline assay has more and longer steps; the improved assay reduces the number of steps, and reduces the total time taken by the method.

Number of Steps:

As illustrated in FIG. 13, the baseline assay included 7 separate steps, while the improved assay includes only 4 separate steps. The decrease in the number of steps was accomplished by combining the cell lysis and the WBC fixation steps; by combining the step of adding WBC markers with the cell-settling step; and by eliminating a washing step (the unbound dye is not removed in a washing step in the improved assay).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the methods disclosed herein.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a volume range of about 1 µL to about 250 µL should be interpreted to include not only the explicitly recited limits of about 1 µL and about 250 µL, but also to include individual volumes such as 2 µL, 3 µL, 4 µL, and sub-ranges such as 10 µL to 50 µL, 20 µL to 100 µL, and so forth.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference in their entireties, and to disclose and describe the structures and/or methods in connection with which the publications are cited.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the methods described herein may be employed in their practice. Any feature, whether preferred or not, may be combined with any other feature, whether preferred or not. The appended claims are not to be interpreted as including means-plus-function limitations, unless such a limitation is explicitly recited in a given claim using the phrase "means for."

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013 Theranos, Inc.

The invention claimed is:

1. A method for improving an assay performed by an automatic assay device, said method comprising:
   altering a baseline assay to provide a revised assay performed by an automatic assay device, said baseline assay having at least two assay steps and comprising an assay for detecting the presence or amount of an analyte in a biological sample having a sample volume,
   said altering the baseline assay comprises:
   reducing the number of assay steps, wherein said reducing the number of assay steps comprises combining two or more assay steps of said baseline assay by reducing the number of reagents used in the performance of the assay to provide that no more than two reagent mixing steps are required for use in said revised assay, said reducing the number of reagents comprises a) combining reagents of the baseline assay to provide a single combined reagent, or b) eliminating a reagent of the baseline assay or a component thereof; and:
   setting said sample volume to about 250 µL or less; then
   altering the dilution of said biological sample to provide a sample dilution of at least 10-fold in the revised assay; then
   setting the assay temperature of the revised assay to between about 32° C. and about 37° C.; then
   altering an assay step, altering the sequence of performance of assay steps, or both, of the baseline assay;

reducing the duration of an assay step effective that the time required to perform the revised assay is reduced as compared to the time required to perform the baseline assay; then requiring that said detection step comprises detecting an optical signal using an optical detector;

performing said revised assay on at least an aliquot of said diluted biological sample using an automatic assay device; then detecting results of the revised assay, wherein said detecting comprises detecting an optical signal; then comparing the results of said revised assay with the results of said baseline assay, and then determining that the baseline assay is improved when the results of the revised assay are as good as, or better than, the baseline results, wherein the revised assay comprises an improved assay when the baseline assay has been improved.

2. The method of claim 1, wherein detecting an optical signal comprises using an optical detector selected from a photomultiplier tube (PMT), a photodiode, a charge-coupled device (CCD), a photon counting detector, a camera, a microscope, and arrays and combinations thereof.

3. The method of claim 1, wherein the time required to perform said improved assay is less than about 30 minutes.

4. The method of claim 1, wherein performing the improved assay comprises three or fewer assay steps.

5. The method of claim 1, wherein the cost of the reagents required for performing the improved assay is less than the cost of reagents required for performing the baseline assay.

6. The method of claim 1, wherein the cost of the reagents required for performing the improved assay comprises about 1¢ or less per assay.

7. The method of claim 1, further comprising performing a second iteration of the steps of claim 1, wherein said improved assay obtained by the performance of the first iteration of the method is used as the baseline assay for the performance of the second iteration of the method.

8. A method for improving a baseline assay for detecting the presence or amount of a first analyte, said detecting being performed by an automatic assay device concurrently with assays for other analytes performed by said automatic assay device, said method comprising the steps of:

selecting a baseline assay having at least two assay steps; and providing an improved assay based on said baseline assay, wherein said providing said improved assay comprises:

reducing the volume of the biological sample if the baseline assay sample volume is greater than about 250 µL; then eliminating pretreatment of said sample if the baseline assay includes a sample pretreatment step; then increasing the dilution of the biological sample by at least 10-fold to provide a diluted sample for providing an aliquot of diluted sample for use in the performance of said improved assay; then:

eliminating a reagent, or combining two reagents to provide a single combined reagent, or a combination thereof, to provide that no more than two reagent mixing steps are required for the performance of said improved assay; then eliminating an assay step or combining two assay steps, or both, if the baseline assay includes more than three steps; then altering the assay temperature to be greater than or equal to 32° C. if the baseline assay temperature is less than 32° C.;

and then reducing the time required to perform the assay to 30 minutes or less if the time required to perform the baseline assay time is greater than 30 minutes;

comparing the results of said improved assay with the results of said baseline assay, and then determining that the baseline assay is improved when the results of the improved assay are as good as, or better than, the baseline results;

thereby providing an improved assay for said first analyte, said improved assay being for concurrent use in an automatic assay device with other assays for other analytes in the same biological sample.

9. The method of claim 8, wherein said improved assay comprises an assay that works better in conjunction with other assays when said improved assay and said other assays are all performed concurrently using the same device or system to perform each of said assays using portions of the same biological sample.

* * * * *